US012311088B2

(12) United States Patent
Kikumoto et al.

(10) Patent No.: US 12,311,088 B2
(45) Date of Patent: May 27, 2025

(54) ARTIFICIAL LUNG DEVICE

(71) Applicant: NIPRO CORPORATION, Osaka (JP)

(72) Inventors: Shunsuke Kikumoto, Muko (JP); Naoaki Yasumura, Kusatsu (JP); Rui Minohara, Kusatsu (JP)

(73) Assignee: NIPRO CORPORATION, Osaka (JP)

( * ) Notice: Subject to any disclaimer, the term of this patent is extended or adjusted under 35 U.S.C. 154(b) by 805 days.

(21) Appl. No.: 17/426,405

(22) PCT Filed: Jan. 29, 2020

(86) PCT No.: PCT/JP2020/003101
§ 371 (c)(1),
(2) Date: Jul. 28, 2021

(87) PCT Pub. No.: WO2020/158777
PCT Pub. Date: Aug. 6, 2020

(65) Prior Publication Data
US 2022/0096721 A1    Mar. 31, 2022

(30) Foreign Application Priority Data

Jan. 29, 2019  (JP) .................. 2019-013110
Jan. 29, 2019  (JP) .................. 2019-013111
(Continued)

(51) Int. Cl.
*A61M 1/16*  (2006.01)
*A61M 1/36*  (2006.01)
*B01D 63/02*  (2006.01)

(52) U.S. Cl.
CPC ........ *A61M 1/1698* (2013.01); *A61M 1/1623* (2014.02); *A61M 1/3623* (2022.05);
(Continued)

(58) Field of Classification Search
CPC ............ A61M 1/1698; A61M 1/3638; A61M 1/3666; A61M 2205/7536; A61M 1/1625;
(Continued)

(56) References Cited

U.S. PATENT DOCUMENTS 4,400,048 A  * 8/1983  Sacks .................... H01R 43/26
                                                         334/46
4,818,490 A  * 4/1989  Carson ................ A61M 1/1629
                                                         422/46
(Continued)

FOREIGN PATENT DOCUMENTS

EP    2383001 A1   11/2011
EP    2383002 A1   11/2011
(Continued)

*Primary Examiner* — Catharine L Anderson
*Assistant Examiner* — Quynh Dao Le
(74) *Attorney, Agent, or Firm* — Alleman Hall & Tuttle LLP

(57) ABSTRACT

An artificial lung device includes: a housing which is formed in a tubular shape including both end portions closed, includes a blood inflow port and a blood outflow port, and is arranged such that a center axis of the housing is directed in a lateral direction; a hollow fiber body (gas exchanger) which is arranged in the housing and performs gas exchange with respect to blood while the blood flows from the blood inflow port to the blood outflow port; and a straightening frame (gas guide portion) by which a gas having flowed through the gas exchanger by the flow of the blood is guided to the gas exchanger again in the housing.

19 Claims, 29 Drawing Sheets

(30) Foreign Application Priority Data

| | | | |
|---|---|---|---|
| Jan. 29, 2019 | (JP) | ................................ | 2019-013112 |
| May 14, 2019 | (JP) | ................................ | 2019-091559 |
| Jan. 24, 2020 | (JP) | ................................ | 2020-009673 |

(52) U.S. Cl.
CPC ........ *A61M 1/3638* (2014.02); *A61M 1/3666* (2013.01); *A61M 1/369* (2013.01); A61M 2205/7536 (2013.01); B01D 63/02 (2013.01); B01D 2313/041 (2022.08); B01D 2313/201 (2022.08); B01D 2313/205 (2022.08)

(58) Field of Classification Search
CPC ............ A61M 1/1627; A61M 2205/75; A61M 1/3632; B01D 2311/2653; B01D 2313/901; B01D 2313/041; B01D 2311/2649; Y10T 29/49826
See application file for complete search history.

(56) References Cited

U.S. PATENT DOCUMENTS

| | | | | | |
|---|---|---|---|---|---|
| 4,898,393 | A | * | 2/1990 | Rollins | .................. F16J 15/008 |
| | | | | | 277/910 |
| 4,900,308 | A | * | 2/1990 | Verkaart | .................. A61M 5/36 |
| | | | | | 604/126 |
| 5,591,251 | A | * | 1/1997 | Brugger | .............. A61M 1/3627 |
| | | | | | 604/122 |
| 5,817,278 | A | | 10/1998 | Fini et al. | |
| 5,823,987 | A | | 10/1998 | Elgas et al. | |
| 5,858,233 | A | | 1/1999 | Elgas et al. | |
| 5,906,741 | A | | 5/1999 | Elgas et al. | |
| 2003/0175151 | A1 | * | 9/2003 | Ghelli | ................. A61M 1/3632 |
| | | | | | 604/4.01 |
| 2011/0186514 | A1 | * | 8/2011 | Ogihara | ............. A61M 1/3627 |
| | | | | | 210/639 |
| 2011/0268608 | A1 | | 11/2011 | Reggiani et al. | |
| 2011/0268609 | A1 | | 11/2011 | Reggiani et al. | |
| 2012/0294761 | A1 | | 11/2012 | Reggiani et al. | |
| 2012/0321512 | A1 | | 12/2012 | Kawamura et al. | |
| 2013/0142695 | A1 | | 6/2013 | Reggiani et al. | |
| 2014/0030149 | A1 | * | 1/2014 | Takeuchi | ............. A61M 1/3623 |
| | | | | | 422/48 |
| 2016/0045870 | A1 | * | 2/2016 | Mizoguchi | ............ B32B 37/142 |
| | | | | | 156/191 |
| 2016/0325036 | A1 | | 11/2016 | Silvestri et al. | |
| 2019/0275229 | A1 | * | 9/2019 | Muller | .................... A61M 1/30 |
| 2020/0345918 | A1 | * | 11/2020 | Hiraguchi | ........... A61M 1/1629 |

FOREIGN PATENT DOCUMENTS

| | | |
|---|---|---|
| EP | 2524712 A1 | 11/2012 |
| JP | H11508476 A | 7/1999 |
| JP | 2010200884 A | 9/2010 |
| JP | 5418274 B2 | 2/2014 |
| JP | 2015144857 A | 8/2015 |
| JP | 5809438 B2 | 11/2015 |

* cited by examiner

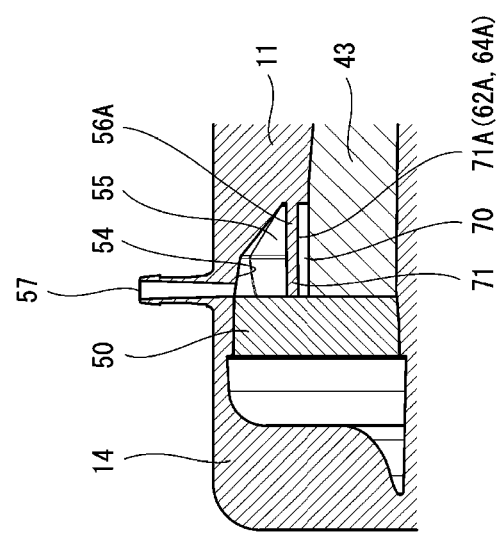
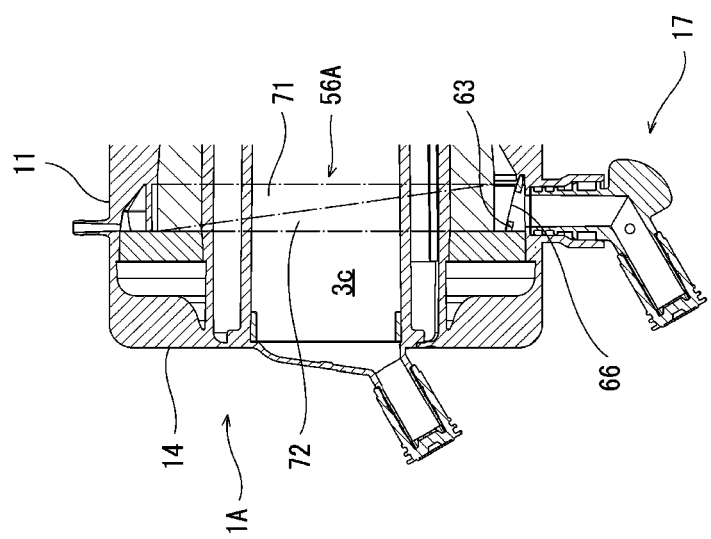
FIG. 4B
FIG. 4A

ARTIFICIAL LUNG DEVICE

TECHNICAL FIELD

The present invention relates to an artificial lung device configured to remove carbon dioxide contained in blood and add oxygen to the blood.

BACKGROUND ART

First, first and second disclosures will be described. In a surgical operation, such as a heart surgical operation, which is performed after the movement of the heart of a patient is stopped, an artificial heart-lung circuit is used as a substitute for the functions of the stopped heart and the lung. An artificial lung device in the artificial heart-lung circuit plays a role of the lung. As such artificial lung device, an artificial lung device disclosed in PTL 1 is known, for example.

The artificial lung device disclosed in PTL 1 includes a housing and a gas exchanger. The housing is formed in a cylindrical shape, and both end portions of the housing are closed by headers. The housing is arranged so as to stand such that the headers are located at upper and lower sides, and the gas exchanger is accommodated in the housing. The gas exchanger is constituted by a bundle and a tubular core and is configured such that the bundle is wound around the tubular core. In such artificial lung device, an annular blood passage is formed between the housing and the tubular core.

Moreover, a diffusing portion is formed at an upper end portion of the tubular core. Blood introduced to the tubular core is diffused to the blood passage by the diffusing portion. The bundle wound around the tubular core is interposed in the blood passage. The bundle is configured such that a plurality of hollow fibers are arranged in a band shape. Gaps are formed among the adjacent hollow fibers, and the diffused blood flows through the gaps toward an outlet port. Moreover, oxygen flows inside the hollow fibers. The hollow fibers remove carbon dioxide from the blood having contacted the hollow fibers, and adds oxygen to the blood.

Next, a third disclosure will be described. In a surgical operation, such as a heart surgical operation, which is performed after the movement of the heart of a patient is stopped, an artificial heart-lung circuit is used as a substitute for the functions of the stopped heart and the lung. An artificial lung in in the artificial heart-lung circuit plays a role of the lung. As such artificial lung, an artificial lung disclosed in PTL 2 is known, for example.

The artificial lung disclosed in PTL 2 includes a housing and a gas exchanger. A blood inlet port is formed at a bottom portion of the housing, and a blood outlet port is formed at an outer peripheral surface of the housing. Moreover, a gas exchanger is accommodated in the housing and adds oxygen to the blood flowing in the housing. Furthermore, a venous blood tube and an artery tube are attached to the corresponding ports such that the blood flows in and out from the artificial lung. In the artificial lung configured as above, the blood is introduced from the vein tube through the blood inlet port into the housing. The introduced blood flows through the gas exchanger in the housing and is discharged from the blood outlet port to the artery tube. When the blood flows through the gas exchanger, oxygen is added to the blood.

Moreover, a fourth disclosure will be described. In a surgical operation, such as a heart surgical operation, which is performed after the movement of the heart of a patient is stopped, an artificial heart-lung circuit is used as a substitute for the functions of the stopped heart and the lung. An artificial lung device in the artificial heart-lung circuit plays a role of the lung. As such artificial lung device, an artificial lung device disclosed in PTL 3 is known, for example.

In the artificial lung device disclosed in PTL 3, a blood inlet is provided in a tubular device casing so as to extend in an axial direction of the device casing. A heating fluid inflow pipe which includes a heating fluid inlet and through which a heating fluid flows toward one side in the axial direction of the device casing and a heating fluid outflow pipe which includes a heating fluid outlet and through which the heating fluid flows toward the other side in the axial direction of the device casing are provided so as to extend in the device casing. Moreover, a blood outlet is provided at an end portion of the device casing which portion is located close to the blood inlet. Furthermore, a gas exchanger including hollow fibers is provided in the device casing. According to this configuration, blood enters into the device casing through the blood inlet, and then, flows around the heating fluid inflow pipe and the heating fluid outflow pipe to be heated by heat exchange. The heated blood flows around the hollow fibers of the gas exchanger to be able to obtain oxygen and discharge carbon dioxide into the hollow fibers.

CITATION LIST

Patent Literature

PTL 1: Published Japanese Translation of PCT Application No. 11-508476
PTL 2: Japanese Patent No. 5418274
PTL 3: Japanese Patent No. 5809438

SUMMARY OF INVENTION

Technical Problem

Regarding the first disclosure, the artificial lung device disclosed in PTL 1 is a so-called vertical artificial lung device. In addition to such artificial lung device, the following artificial lung device has also been developed. To be specific, a horizontal artificial lung device arranged such that a housing thereof is laid in a horizontal direction has also been developed. In the horizontal artificial lung device, a gas exchanger is also directed in the horizontal direction in the housing, and an annular blood passage extends in the horizontal direction. The blood flows through the blood passage, and bubbles are carried together with the blood in some cases.

Basically, such bubbles are absorbed by the hollow fibers when contacting the hollow fibers, and most of the bubbles are removed. However, when a large amount of bubbles are carried together with the blood, the hollow fibers may not adequately absorb the bubbles. In such a case, the bubbles which were not absorbed flow toward a ceiling in the housing and are accumulated in the vicinity of the ceiling. Then, if the bubbles are excessively accumulated, the bubbles may be carried toward the outlet port by the flow of the blood.

An object of the present invention is to provide an artificial lung device capable of removing bubbles carried by blood and preventing the bubbles from being excessively accumulated.

Regarding the second disclosure, in conventional artificial lung devices such as the artificial lung device disclosed in PTL 1, the blood flows through the blood passage of the gaps in the bundle constituting the gas exchanger, and in some cases, the bubbles are carried together with the blood. Basically, such bubbles are absorbed by the hollow fibers of the bundle when contacting the hollow fibers, and most of the bobbles are removed. However, when a large amount of bubbles are carried together with the blood, the bubbles may not be adequately absorbed by the hollow fibers in a period in which the blood flows through the gas exchanger. Then, when the bubbles which were not absorbed by the hollow fibers are excessively accumulated, the bubbles may be carried toward the outlet port by the flow of the blood.

Another object of the present invention is to provide an artificial lung device capable of preventing bubbles, carried by blood, from being excessively accumulated.

Regarding the third disclosure, in the artificial lung described in PTL 2, a suspending portion is formed at an upper portion of the housing, and the artificial lung is used by being suspended in such a manner that the suspending portion is hung on a suspending device or the like. The artificial lung configured as above constitutes part of the artificial heart-lung circuit and is used in such a manner that the vein tube and the artery tube attached to the corresponding ports are connected to corresponding apparatuses. According to the artificial heart-lung circuit, the blood flows in the circuit. Therefore, as a preparation in advance, the blood passage of the circuit is filled with saline. Therefore, the blood of a patient is diluted by the saline. The amount of blood differs person to person depending on the weight, physique, and the like of the patient. When the amount of saline is large relative to the amount of blood, the blood is diluted, and required blood component concentration of the blood cannot be maintained. Therefore, the blood component needs to be compensated by blood transfusion. To reduce the amount of blood used by the blood transfusion, the length of the blood passage in the artificial lung circuit needs to be shortened as much as possible. For example, this can be realized by reducing the lengths of the tubes.

On the other hand, the tubes become long due to the routing of the tubes corresponding to an arrangement relation between the artificial lung and respective devices. For example, when the blood inlet port is not directed to an apparatus to which the blood inlet port is connected, but is directed in an opposite direction, the vein tube needs to be directed to the apparatus by changing the direction of the vein tube, such as by bending the vein tube in a U shape, and therefore, the vein tube increases in length by this bending. Regarding this, in PTL 2, the direction of the blood inlet port is changed by, for example, rotating the suspending portion relative to the suspending device. With this, the vein tube does not have to be bent, and therefore, the vein tube is shortened as much as possible.

Similarly, it is preferable that the artery tube be shortened as much as possible. However, according to the artificial lung of PTL 2, the following matters occur. To be specific, in the artificial lung of PTL 2, the blood inlet port and the blood outlet port extend in respective directions opposite to each other. Therefore, even when the artificial lung is rotated relative to the suspending device, the two ports are never directed in the same direction. On this account, when the device to which the blood inlet port is connected and the device to which the blood outlet port is connected are arranged at the same side of the artificial lung, at least one of the tube connected to the blood inlet port and the tube connected to the blood outlet port needs to be bent, for example, and the bent tube increases in length. Moreover, when the degree of bending of the tube is large, passage resistance becomes large at this bent portion. In this case, the blood pressure in the tube may increase, and the bloodstream in the tube may stop. Therefore, the routing of the two tubes needs to be devised.

Yet another object of the present invention is to provide an artificial lung device capable of facilitating routing of tubes by which a blood inflow port and a blood outflow port are connected to corresponding apparatuses.

Regarding the fourth disclosure, the artificial lung device of PTL 3 is configured such that: the blood outlet is provided at an end portion of the device casing which portion is located close to the blood inlet; and the blood having flowed into the device casing flows radially and spreads concentrically in the casing and flows out from the blood outlet. Therefore, a time period in which the blood and the heat exchanger contact each other is short, and part of the blood having entered into the device casing through the blood inlet is not adequately subjected to the heat exchange and flows out from the blood outlet. On this account, the blood may not be adequately heated or cooled as a whole.

Still another object of the present invention is to provide an artificial lung device capable of adequately heating blood.

Solution to Problem

The first disclosure will be described. An artificial lung device according to the present invention includes: a housing including a blood inflow port and a blood outflow port and arranged such that a center axis of the housing is directed in a lateral direction; a gas exchanger arranged in the housing and configured to perform gas exchange with respect to blood while the blood flows from the blood inflow port to the blood outflow port; a filter structure arranged around the gas exchanger; an opposing wall arranged so as to be opposed to a surface of the gas exchanger; and a space constituted by the opposing wall and/or the filter structure. The opposing wall includes an inclined surface inclined toward the gas exchanger, and/or the filter structure includes an inclined surface inclined toward the gas exchanger.

According to this configuration, the bubbles which flowed through the gas exchanger but were not absorbed flow to the gas exchanger again in the artificial lung device. Therefore, a larger amount of bubbles can be absorbed by the gas exchanger. On this account, the bubbles can be removed in the housing and can be prevented from being excessively accumulated in the housing.

Moreover, in the above artificial lung device, the gas exchanger may be formed in a columnar shape such that a center axis of the gas exchanger is directed in the lateral direction in the housing. The bubble guide portion may include a straightening surface provided so as to cross a passage extending from the gas exchanger to the blood outflow port. The straightening surface may be provided so as to be opposed to an outer peripheral surface of the gas exchanger and surround the gas exchanger. The straightening surface may include a first straightening surface provided at a relatively lower side and inclined such that a downstream portion of the first straightening surface in a flow direction of the blood is located closer to the outer peripheral surface of the gas exchanger than an upstream portion of the first straightening surface in the flow direction of the blood and a second straightening surface provided at a relatively upper side and located closer to the outer peripheral surface of the gas exchanger than the upstream portion of the first straightening surface, the second straightening surface being inclined differently from the first straightening surface.

In this case, the bubbles received by the upstream portion of the first straightening surface located at a lower portion of the bubble guide portion approach the outer peripheral surface of the gas exchanger as the bubbles flow toward the downstream portion along the flow of the blood. Moreover, the bubbles received by the first straightening surface approach the outer peripheral surface of the gas exchanger as the bubbles flows upward in the blood toward the second straightening surface located at the upper side. Therefore, according to the above configuration, the bubbles can flow out from the gas exchanger, reach the bubble guide portion, and be guided to the gas exchanger again.

Moreover, a filter may be provided at the straightening surface.

According to this configuration, foreign matters can be removed from the blood received by the straightening surface.

Moreover, in the above artificial lung device, an opening may be formed at the first straightening surface, and a filter may be provided at the opening.

According to this configuration, foreign matters can be removed from the blood flowing out from the artificial lung device through the blood outflow port. Moreover, since the filter is provided at not the second straightening surface at the upper side where the bubbles tend to be accumulated but the first straightening surface at the lower side, the bubbles can be prevented from passing through the filter.

Moreover, in the above artificial lung device, the second straightening surface may be located so as to be spaced apart from the outer peripheral surface of the gas exchanger by a predetermined distance, and a bubble storing portion may be formed between the second straightening surface and the outer peripheral surface of the gas exchanger.

According to this configuration, the bubbles flowing upward along the straightening surface can be brought into contact with the outer peripheral surface of the gas exchanger before reaching the second straightening surface. In addition, when a large amount of bubbles flow, the bubbles can be temporarily stored in the bubble storing portion that is a space between the second straightening surface and the outer peripheral surface of the gas exchanger. Moreover, when a certain amount of bubbles are accumulated in the bubble storing portion, the bubbles can be drawn into the hollow fiber membrane to be removed.

Moreover, in the above artificial lung device, at least the second straightening surface of the straightening surface may be constituted by an inner wall surface of the housing.

According to this configuration, positioning accuracy between the second straightening surface and the outer peripheral surface of the gas exchanger at the time of assembling can be improved.

Moreover, in the above artificial lung device, a filter may be provided at the blood outflow port.

According to this configuration, foreign matters can be removed from the blood at the blood outflow port.

Moreover, in the above artificial lung device, the filter may be formed in a columnar shape such that a dimension of the filter in a flow direction of the blood in the blood outflow port is larger than an inner diameter of the blood outflow port.

According to this configuration, since the volume of the filter can be increased, foreign matters can be more surely removed from the blood.

Moreover, the above artificial lung device may further include a bubble trap portion provided downstream of the bubble storing portion.

According to this configuration, for example, even when the bubbles have passed through the filter, such bubbles can be trapped by the bubble storing portion again.

Moreover, in the above artificial lung device, the bubble trap portion may include an air vent port.

According to this configuration, the bubbles accumulated in the bubble storing portion can be discharged through the air vent port to the outside.

The artificial lung device according to the present invention includes: a housing formed in a tubular shape including both end portions that are closed, the housing including a blood inflow port and a blood outflow port and arranged such that a center axis of the housing is directed in a lateral direction; a gas exchanger arranged in the housing and configured to perform gas exchange with respect to blood while the blood flows from the blood inflow port to the blood outflow port; a straightening frame including a filter and provided around the gas exchanger; and a bubble storing portion provided between the straightening frame and the gas exchanger. The bubble storing portion is located at an upper side of the housing and faces the gas exchanger.

According to this configuration, the bubble storing portion is located at the upper side of the housing and faces the gas exchanger so as to be adjacent to the gas exchanger. Therefore, when the bubbles are accumulated in the space in the bubble storing portion, the bubbles can be brought into contact with the gas exchanger and can be taken in the gas exchanger. With this, the bubbles can be prevented from being excessively accumulated in the bubble storing portion.

Moreover, in the above artificial lung device, the bubble storing portion may include an inner peripheral surface of the straightening frame and an outer peripheral surface of the gas exchanger.

Moreover, in the above artificial lung device, the straightening frame may include an inclined straightening surface located close to the gas exchanger.

According to this configuration, the bubbles in the bubble storing portion can be smoothly guided to and taken in the gas exchanger by the inclined straightening surface included in the straightening frame.

The second disclosure will be described. An artificial lung device according to the present invention includes: a housing including a blood inflow port and a blood outflow port; a gas exchanger arranged in the housing and configured to perform gas exchange with respect to blood while the blood flows from the blood inflow port to the blood outflow port; and an opposing wall arranged so as to be opposed to a surface of the gas exchanger and forming a space between the opposing wall and the surface of the gas exchanger. The surface of the gas exchanger and the opposing wall constitute a bubble guide portion by which bubbles having flowed through the gas exchanger are guided to the gas exchanger. A separation dimension between the surface of the gas exchanger and the opposing wall gradually decreases to approach zero toward a vertically upper side or toward a downstream side in a flow direction of the blood in the space.

According to this configuration, since the bubbles which flowed through the gas exchanger in the artificial lung device but were not absorbed flows toward the gas exchanger again, a larger amount of bubbles can be absorbed by the gas exchanger. In addition, the surface of the gas exchanger and the opposing wall which constitute the bubble guide portion contact each other at the vertically upper side or the downstream side (the separation dimension becomes zero) or do not contact each other but gradually get close to each other (the separation dimension approaches zero). Therefore, the bubbles having reached the bubble guide portion can be more surely guided to the gas exchanger again, and the bubbles can be prevented from being excessively accumulated in the housing.

Moreover, in the above artificial lung device, the filter configured to remove foreign matters in the blood may be provided so as to cross a passage such that part of the surface of the filter contacts the surface of the gas exchanger, the passage being a passage through which the blood having flowed through the gas exchanger flows toward the blood outflow port. The filter may constitute the opposing wall.

According to this configuration, a dedicated opposing wall does not have to be provided, and the filter configured to remove foreign matters in the blood can serve as the opposing wall. Moreover, since the filter is provided downstream of the gas exchanger in the flow direction of the blood, the bubbles which remain although having flowed through the gas exchanger can be surely collected and guided to the gas exchanger again.

Moreover, in the above artificial lung device, the gas exchanger may be provided such that part of the surface of the gas exchanger contacts an inner wall surface of the housing, and the inner wall surface of the housing may constitute the opposing wall.

According to this configuration, a dedicated opposing wall does not have to be provided, and the housing originally included can serve as the opposing wall.

Moreover, the above artificial lung device may further include a heat exchanger arranged in the housing and configured to adjust a temperature of the blood having flowed into the heat exchanger through the blood inflow port and deliver to the gas exchanger the blood having been adjusted in temperature. The gas exchanger may be formed in a tubular shape surrounding the heat exchanger. A tubular wall may be provided between the heat exchanger and the gas exchanger so as to separate the heat exchanger and the gas exchanger from each other. The bubble guide portion may be formed by an inner peripheral surface of the gas exchanger and a portion of the tubular wall which portion is opposed to the inner peripheral surface of the gas exchanger.

According to this configuration, when the gas exchanger is formed in a tubular shape surrounding the heat exchanger, the bubble guide portion can be provided at the inner peripheral surface side of the gas exchanger.

The third disclosure will be described. An artificial lung device of the present invention includes: a gas exchanger configured to perform gas exchange with respect to blood which has contacted the gas exchanger; and a housing including a hollow housing main body accommodating the gas exchanger, a blood inflow port which is formed at the housing main body and through which the blood flows into the housing main body for the gas exchange with the gas exchanger, a cylindrical blood outflow port through which the blood in the housing main body is discharged, and an attaching portion to which the blood outflow port is attached. A base end-side portion of the blood outflow port is attached to the attaching portion such that the blood outflow port is rotatable about an axis of the base end-side portion. The blood outflow port is bent such that a tip end-side portion of the blood outflow port forms a predetermined angle with respect to the axis of the base end-side portion.

According to the present invention, since the blood outflow port is bent and is provided at the housing main body so as to be rotatable, the direction of the blood outflow port can be changed by rotating the blood outflow port regardless of the directions of the housing main body and the blood inflow port. With this, the arrangement position, direction, and the like of the artificial lung device can be prevented from being restricted, and the routing of the tubes connecting the blood inflow port, the blood outflow port, and apparatuses can be facilitated.

Moreover, in the above artificial lung device, the attaching portion may be formed in a substantially cylindrical shape. An inner peripheral surface of the attaching portion may include an engaging portion. The base end-side portion of the blood outflow port may be attached to the attaching portion. The base end-side portion of the blood outflow port may include an engaged portion which is engaged with the engaging portion when the base end-side portion of the blood outflow port is attached to the attaching portion.

The blood outflow port receives, from the blood flowing in or introduced to the blood outflow port, a load acting in such a direction that the blood outflow port is detached from the attaching portion. However, since the engaging portion and the engaged portion are engaged with each other as in the above configuration, the blood outflow port can be prevented from being easily detached from the attaching portion.

Moreover, in the above artificial lung device, one of the engaging portion and the engaged portion may be constituted by a plurality of engagement pieces arranged so as to be spaced apart from each other in a circumferential direction. Each of the engagement pieces may be formed in a tapered shape that projects inward in a radial direction as the engagement piece extends upward. The other of the engaging portion and the engaged portion may be arranged so as to correspond to the engagement pieces, be formed so as to project outward in the radial direction, and be engaged with the plurality of engagement pieces so as to be located higher than the plurality of engagement pieces.

According to this configuration, when attaching the blood outflow port to the attaching portion, the engaged portion can be guided by a plurality of engagement pieces formed in a tapered shape. With this, the blood inflow port can be easily attached, and the artificial lung device can be easily manufactured.

Moreover, the above artificial lung device may further include first and second sealing members configured to seal between an outer peripheral surface of the base end-side portion and an inner peripheral surface of the attaching portion. The first sealing member may be arranged at a portion of an outer peripheral surface of the base end-side portion of the blood outflow port which portion is closer to a base end of the blood outflow port than the second sealing member. Compressibility of the second sealing member may be higher than compressibility of the first sealing member.

In this case, the compressibility of the second sealing member is higher than that of the first sealing member. Therefore, even if the blood leaks from the first sealing member, the second sealing member can prevent the blood from leaking to the outside. Moreover, by lowering the compressibility of the first sealing member, an increase in sliding resistance generated when rotating the blood outflow port can be suppressed.

Moreover, in the above artificial lung device, the base end-side portion of the blood inflow port may project from the housing main body toward one side in an upper-lower direction. A tip end-side portion of the blood inflow port may be connected to the base end-side portion through a bent portion and be inclined outward in a radial direction so as to be directed toward one side in the upper-lower direction relative to the base end-side portion. The blood outflow port may include a holding portion formed at the bent portion so as to project from the bent portion toward one side in the upper-lower direction.

According to this configuration, the blood inflow port can be easily rotated by the holding portion. Moreover, since the holding portion is formed so as to project, the holding portion serves as a rib and can improve the rigidity of the blood inflow port. Furthermore, when the artificial lung device falls in a state where the blood inflow port is located at the lower side, the holding portion can be made to contact a floor or the like. With this, impact at the time of the falling can be made to act in the axial direction of the base end-side portion. Since the base end-side portion is formed along the axial direction, the base end-side portion has high rigidity. Since the holding portion lands first at the time of the falling, the blood inflow port can be prevented from breaking.

An artificial lung device of the present invention includes: a tubular housing including both ends that are closed; a heat exchanger provided in the housing and configured to perform heat exchange with respect to blood; a gas exchanger arranged around an axial direction of the heat exchanger in the housing and configured to be in fluid communication with the heat exchanger and perform gas exchange with respect to the blood; a heat medium partial chamber which is arranged between the heat exchanger and the gas exchanger and around the axial direction of the heat exchanger and through which a heat medium flowing in and out from the heat exchanger flows; a blood inflow port provided at a first end side of the housing and configured to be in fluid communication with the heat exchanger; a blood outflow port provided at the housing and configured to be in fluid communication with the gas exchanger; a medium inflow port and a medium outflow port which are provided at a second end side of the housing and are in fluid communication with the heat medium partial chamber; and a bridge structure forming a blood passage through which the blood flows in a radial direction from the heat exchanger through a second end side of the heat medium partial chamber to the gas exchanger and a medium passage through which the heat medium flows in the axial direction between the medium inflow port and the heat medium partial chamber and between the medium outflow port and the heat medium partial chamber.

According to the present invention, the blood flows into the blood inflow port provided at the first end side of the housing, flows through the heat exchanger and the second end side of the heat medium partial chamber, and flows through the blood passage to the gas exchanger. With this, the heat exchange with respect to the blood is adequately performed. Moreover, since the blood inflow port is provided at the first end side of the housing, and the medium outflow port is provided at the second end side of the housing, sanitation is improved.

Moreover, an artificial lung device of the present invention includes: a tubular housing including both ends that are closed, the housing including a blood inflow port, a blood outflow port, a medium inflow port, and a medium outflow port; a heat exchanger configured to be in fluid communication with the blood inflow port; and a gas exchanger arranged around the heat exchanger and configured to be in fluid communication with the heat exchanger. The heat exchanger includes: a blood chamber configured to be in fluid communication with the blood inflow port and the blood outflow port and including an end portion; and a heat exchange portion configured to in fluid communication with the medium inflow port and the medium outflow port, a heat medium flowing through the heat exchange portion. The heat exchange portion includes an extending portion arranged so as to extend beyond the end portion of the blood chamber in the axial direction of the housing.

According to the present invention, the housing can be prevented from increasing in size in the radial direction. With this, priming volume can be reduced.

Advantageous Effects of Invention

According to the first disclosure, the present invention can provide an artificial lung device configured to be able to prevent bubbles, carried by blood, form being excessively accumulated. According to the second disclosure, the present invention can provide an artificial lung device configured to be able to prevent bubbles, carried by blood, from being excessively accumulated. According to the third disclosure, the present invention can facilitate routing of tubes connecting a blood inflow port, a blood outflow port, and apparatuses. According to the fourth disclosure, the present invention can provide an artificial lung device capable of adequately heating blood.

BRIEF DESCRIPTION OF DRAWINGS

FIGS. 4A and 4B are partial sectional views showing the straightening frame of the artificial lung device according to Embodiment 2 of the first disclosure.

FIG. 22A is a front view showing that the tip end of the blood outflow port is directed toward a near side. FIG. 22B is a front view showing that the tip end of the blood outflow port is directed toward a deep side.

DESCRIPTION OF EMBODIMENTS

Hereinafter, artificial lung devices according to embodiments of first to fourth disclosures of the present invention will be described with reference to the drawings. It should be noted that each artificial lung device described below is merely one embodiment of the present invention, and the present invention is not limited to the embodiments. Additions, deletions, and modifications may be made within the scope of the present invention.

Embodiment 1 to 3 of the first disclosure will be described.

Embodiment 1 of First Disclosure

Figure 1:
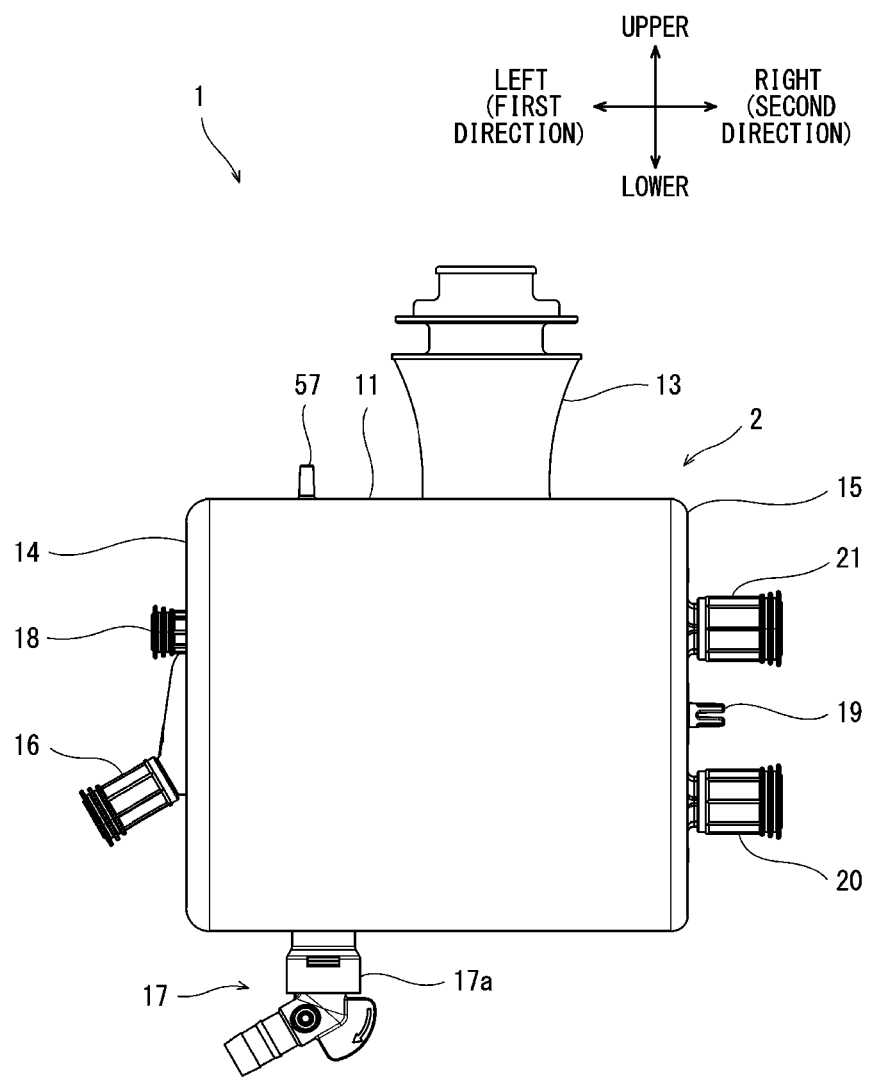
FIG. 1 is a front view showing appearance of an artificial lung device according to the present embodiment of the first disclosure.
Figure 2:
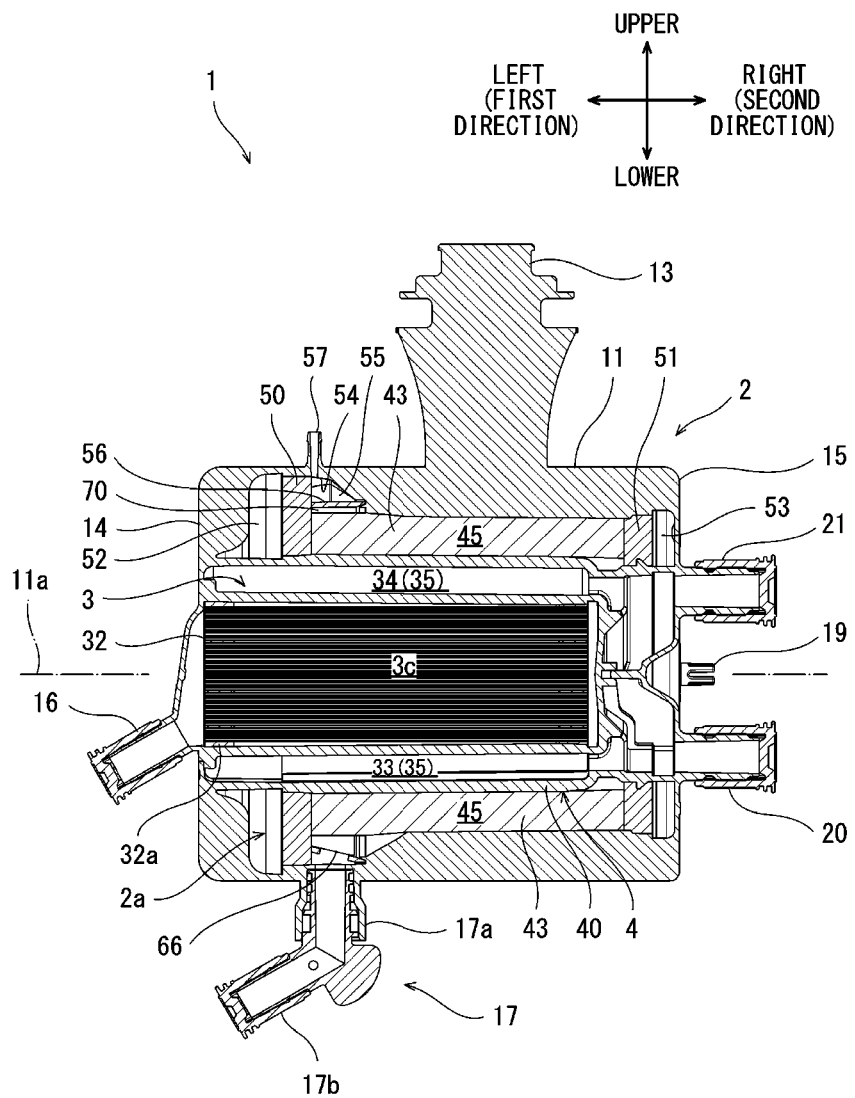
FIG. 2 is a front sectional view showing the artificial lung device of FIG. 1 in the first disclosure.

FIG. 1 is a front view showing appearance of an artificial lung device 1 of the present embodiment. FIG. 2 is a front sectional view showing the artificial lung device 1 of FIG. 1. In a surgical operation performed after the movement of the heart of a patient is stopped, the artificial lung device 1 shown in FIGS. 1 and 2 is used as a substitute for the function of the lung of the patient. Therefore, the artificial lung device 1 has a gas exchange function of removing carbon dioxide contained in blood of the patient and adding oxygen to the blood; and a heat exchange function of adjusting the temperature of the blood. The artificial lung device 1 having such functions is of a so-called horizontal type and includes a housing 2, an inner tube 3, and a middle tube 4.

The housing 2 is formed in a substantially cylindrical shape including both end portions that are closed. The housing 2 includes an internal space 2a (see FIG. 2) accommodating the inner tube 3 and the middle tube 4. Specifically, the housing 2 includes a housing main body 11, a suspending portion 13, and two cap portions 14 and 15.

The housing main body 11 is formed in a substantially cylindrical shape, and the suspending portion 13 is provided at an outer peripheral surface of an upper portion of the housing main body 11. The suspending portion 13 is arranged at a middle portion of the housing main body 11 which portion is located at a middle position in a direction along an axis 11a of the housing main body 11. The suspending portion 13 extends in a radially outward direction from the outer peripheral surface of the upper portion of the housing main body 11. The suspending portion 13 is formed in, for example, a substantially columnar shape and is suspended in such a manner that a tip end-side portion thereof is attached to an external suspending device (not shown). Therefore, the housing main body 11 can be suspended through the suspending portion 13, and the axis 11a of the suspended housing main body 11 extends in a horizontal direction.

The housing main body 11 includes opening end portions at both sides in the direction along the axis 11a. The opening end portion at one side (left side in FIG. 2) is closed by the cap portion 14, and the opening end portion at the other side (right side in FIG. 2) is closed by the cap portion 15. Each of the cap portions 14 and 15 is formed in a substantially circular plate shape. It should be noted that in the following description, for convenience of explanation, regarding the direction along the axis 11a of the housing main body 11, a side where the cap portion 14 is located is referred to as a left side, and a side where the cap portion 15 is located is referred to as a right side.

As shown in FIG. 1, a gas supply port 18 is formed at the cap portion 14. The gas supply port 18 is formed in a substantially cylindrical shape and projects to the left side in the direction along the axis 11a from the vicinity of an outer peripheral edge of the cap portion 14. The gas supply port 18 is connected to an external gas supply device (not shown) through a gas supply tube. Oxygen-containing gas supplied from the gas supply device is introduced through the gas supply port 18 into the housing 2.

A gas discharge port 19 is formed at the cap portion 15. The gas discharge port 19 is formed in a substantially cylindrical shape and projects to the right side in the direction along the axis 11a from the vicinity of an outer peripheral edge of the cap portion 15. The gas discharge port 19 is connected to the external gas supply device through a gas discharge tube. The gas supplied through the gas supply port 18 into the housing 2 is discharged through the gas discharge port 19 and is returned to the gas supply device.

A blood inflow port 16 is formed in the vicinity of a central axis (axis which substantially coincides with the axis 11a of the housing main body 11) of the cap portion 14. The blood inflow port 16 is formed in a substantially cylindrical shape and projects from a lower side of the central axis of the cap portion 14 in a left and obliquely downward direction. A venous blood tube (not shown) is connected to the blood inflow port 16, and venous blood is introduced through the venous blood tube and the blood inflow port 16 into the housing main body 11.

A blood outflow port 17 is formed at a position of a lower portion (portion opposite to the suspending portion 13) of the outer peripheral surface of the housing main body 11 which position is located at the left side of a center of the artificial lung device 1 in the direction along the axis 11a. More specifically, the blood outflow port 17 includes a port attaching portion 17a and a port main body portion 17b. The port attaching portion 17a is formed in a substantially cylindrical shape. The port attaching portion 17a is provided at the lower portion of the outer peripheral surface of the housing main body 11 and projects downward. The port main body portion 17b is inserted into the port attaching portion 17a from a lower side. The port main body portion 17b is formed in a substantially cylindrical shape. The port main body portion 17b projects downward from a lower end of the port attaching portion 17a and is bent in an obliquely downward direction at a tip side of the lower end of the port attaching portion 17a. An arterial blood tube (not shown) is connected to the blood outflow port 17 (port main body portion 17b). The arterial blood generated in the artificial lung device 1 is delivered through the arterial blood tube to an outside.

A medium inflow port 20 and a medium outflow port 21 are provided at the cap portion 15. The medium inflow port 20 and the medium outflow port 21 are arranged so as to sandwich a central axis of the cap portion 15 and be spaced apart from each other in an upper-lower direction. The two ports 20 and 21 do not necessarily have to be spaced apart from each other in the upper-lower direction and may be arranged so as to be spaced apart from each other in a left-right direction. Each of the two ports 20 and 21 is formed in a substantially cylindrical shape and projects from the cap portion 15 toward the right side in the direction along the axis 11a. The medium inflow port 20 is connected to a medium supply tube (not shown), and a heat medium, such as hot water or cold water, from the medium supply tube is introduced through the medium inflow port 20 into the housing 2. The medium outflow port 21 is connected to a medium discharge tube (not shown), and the heat medium in the housing 2 is discharged through the medium outflow port 21 and the medium discharge tube to the outside of the housing 2.

The inner tube 3 and the middle tube 4 are accommodated in the internal space 2a of the housing 2 so as to be coaxial with each other. A heat exchange chamber 3c, a gas exchange chamber 45, and the like are formed by the inner tube 3 and the middle tube 4.

An outer diameter of the middle tube 4 is smaller than an inner diameter of the housing main body 11. The middle tube 4 is arranged at the housing main body 11 such that a center axis of the middle tube 4 and a center axis of the housing main body 11 coincide with each other. With this, a ring-shaped space is formed between an outer peripheral surface of the middle tube 4 and an inner peripheral surface of the housing main body 11, and this ring-shaped space constitutes the gas exchange chamber 45. A hollow fiber body (gas exchanger) 43 is provided in the gas exchange chamber 45.

The hollow fiber body 43 is formed in a substantially cylindrical shape (or a columnar shape including an internal space) and is constituted by a plurality of hollow fibers. Specifically, the hollow fiber body 43 is configured such that a mat-shaped hollow fiber membrane (bundle) formed by making a plurality of hollow fibers intersect with each other and laminating the plurality of hollow fibers on each other is wound around the outer peripheral surface of the middle tube 4. The hollow fiber membrane is wound such that the thickness of the hollow fiber body 43 substantially coincides with an interval between the middle tube 4 and the housing main body 11. To be specific, the hollow fiber body 43 is formed along the inner peripheral surface of the housing main body 11 such that an outer peripheral surface of the hollow fiber body 43 contacts the inner peripheral surface of the housing main body 11 over the substantially entire periphery.

An annular sealing member 50 is provided in a region located at the left side of the gas exchange chamber 45. The sealing member 50 forms a gas inflow space 52 together with an inner peripheral surface of the cap portion 14, and the gas supply port 18 communicates with the gas inflow space 52. Moreover, an annular sealing member 51 is provided in a region located at the right side of the gas exchange chamber 45. The sealing member 51 forms a gas outflow space 53 together with an inner peripheral surface of the cap portion 15, and the gas discharge port 19 communicates with the gas outflow space 53.

The hollow fiber body 43 is provided so as to be sandwiched between the sealing member 50 and the sealing member 51 from the left and right sides. The sealing member 50 seals between the middle tube 4 and the housing 2 at the left side of the gas exchange chamber 45 in an entire circumferential direction. Moreover, the sealing member 51 seals between the middle tube 4 and the housing 2 at the right side of the gas exchange chamber 45 in the entire circumferential direction. According to this configuration, the gas inflow space 52 communicating with the gas supply port 18 and the gas outflow space 53 communicating with the gas discharge port 19 communicate with each other through inner holes of the plurality of hollow fibers constituting the hollow fiber body 43.

In the hollow fiber body 43, gaps are provided among the plurality of hollow fibers constituting the hollow fiber body 43. In the gas exchange chamber 45, blood flows through the gaps. Specifically, the blood introduced to the gas exchange chamber 45 flows through the gaps in the hollow fiber body 43 and flows from the right side to the left side in the direction along the axis 11a while contacting the hollow fibers. Oxygen-rich gas flows from an external gas supply device through the gas supply port 18 and the gas inflow space 52 into the inner holes of the hollow fibers. Therefore, when the blood having high carbon dioxide concentration contacts the hollow fibers, gas exchange is performed between the blood and the gas in the hollow fibers. With this, carbon dioxide is removed from the blood, and oxygen is added to the blood. As above, the blood flows to the left side in the direction along the axis 11a in the gas exchange chamber 45 while being subjected to the gas exchange. On the other hand, the gas flowing through the inner holes of the hollow fibers flows to the right side while being subjected to the gas exchange, and returns to the external gas supply device through the gas outflow space 53 and the gas discharge port 19.

A downstream (left) portion of the gas exchange chamber 45 is larger in diameter in the radially outward direction than the other portion of the gas exchange chamber 45. Specifically, as shown in FIG. 2, a ring-shaped recess 54 that is recessed in the radially outward direction is formed on an inner peripheral surface of a left portion of the housing main body 11. The diameter of a left portion of the recess 54 is substantially constant. On the other hand, a right portion of the recess 54 tapers toward the right side, i.e., the right portion of the recess 54 is formed in a tapered shape. The sealing member 50 is arranged at a middle portion of the recess 54. A portion of the recess 54 which portion is located at the right side of the sealing member 50 is formed in a tapered shape as described above. An outer peripheral space 55 formed between the recess 54 and the hollow fiber body 43 is formed so as to surround the hollow fiber body 43, and a lower portion of the outer peripheral space 55 communicates with the blood outflow port 17. According to this configuration, the blood having been subjected to the gas exchange in the gas exchange chamber 45 is introduced to the outer peripheral space 55 and then flows into the blood outflow port 17.

A filter structure having an annular shape along the outer peripheral space 55 is provided in the outer peripheral space 55. The filter structure includes a straightening frame 56. The straightening frame 56 guides bubbles, carried together with the blood flowing through the gas exchange chamber 45 while being subjected to the gas exchange, toward the hollow fiber body 43 again and makes the bubbles be taken in the hollow fibers. Details will be described later.

An air vent port 57 through which the outer peripheral space 55 communicates with the outside is provided at an upper portion of the housing main body 11. The air vent port 57 discharges, to the outside, the bubbles accumulated in an upper portion (bubble trap portion) of the outer peripheral space 55. The bubble trap portion is provided downstream of a below-described bubble storing portion 70 and is provided so as to be able to store the bubbles. In the present embodiment, such bubble trap portion is constituted by the recess 54 (especially a portion of the recess 54 which portion is located at an upper side of the hollow fiber body 43). An outside opening end of the air vent port 57 is basically covered with a cap member (not shown). Therefore, the bubbles and the blood are not discharged through the air vent port 57 except for when the bubbles are discharged.

The middle tube 4 includes a middle tube main body portion 40 and a bridge portion 41. The middle tube main body portion 40 is formed in a cylindrical shape and forms the gas exchange chamber 45 at the outside of the middle tube main body portion 40. The inner tube 3 forming the heat exchange chamber 3c is accommodated in an inner space of the middle tube main body portion 40. The bridge portion 41 forms heat medium passages and a blood passage which three-dimensionally intersect with each other. The heat medium which flows in and out from the heat exchange chamber 3c flows through the heat medium passage, and the blood which flows from the heat exchange chamber 3c toward the gas exchange chamber 45 flows through the blood passage.

As shown in FIG. 2, a tube bundle 32 is inserted into and arranged in the heat exchange chamber 3c in the inner tube 3 such that an axial direction of the tube bundle 32 coincides with an axial direction of the inner tube 3. The tube bundle 32 is an assembly of a plurality of heat exchange pipes. The heat exchange pipes are long and small-diameter tubes made of a material, such as stainless steel, having high heat conductivity. The blood from the blood inflow port 16 flows into the heat exchange pipes through left openings of the heat exchange pipes.

An outer diameter of the inner tube 3 is smaller than an inner diameter of the middle tube 4. The inner tube 3 is positioned relative to the middle tube 4 such that an axis of the inner tube 3 coincides with the axis of the middle tube 4. With this, an annular heat medium chamber 35 through which the heat medium flows is formed between an outer peripheral surface of the inner tube 3 and an inner peripheral surface of the middle tube 4. The heat medium chamber 35 is divided into a first heat medium partial chamber 33 located at an upper side and a second heat medium partial chamber 34 located at a lower side. The first heat medium partial chamber 33 at the upper side communicates with the medium outflow port 21 through one heat medium passage of the bridge portion 41. The second heat medium partial chamber 34 at the lower side communicates with the medium inflow port 20 through another heat medium passage of the bridge portion 41.

As shown in FIG. 2, a pair of tube supporting bodies 32a each having a circular plate shape are provided in the inner tube 3. An outer diameter of each tube supporting body 32a substantially coincides with an inner diameter of the inner tube 3. The tube supporting body 32a located at the left side is inserted into a left end of the inner tube 3, and the tube supporting body 32a located at the right side is inserted into a right end of the inner tube 3. Left ends of the heat exchange pipes constituting the tube bundle 32 are respectively inserted into a plurality of holes radially provided at the tube supporting body 32a located at the left side, and right ends of the heat exchange pipes constituting the tube bundle 32 are respectively inserted into a plurality of holes radially provided at the tube supporting body 32a located at the right side.

With this, both opening end portions of the inner tube 3 are sealed by the pair of tube supporting bodies 32a, and both ends of each heat exchange pipe of the tube bundle 32 are open at both end sides of the inner tube 3. Left openings of the heat exchange pipes of the tube bundle 32 communicate with the blood inflow port 16, and right openings of the heat exchange pipes of the tube bundle 32 communicate with the gas exchange chamber 45 through the blood passage of the bridge portion 41.

Moreover, a plurality of through holes are formed at each of upper and lower portions of the inner tube 3. The inside of the inner tube 3 and the first heat medium partial chamber 33 located at the upper side communicate with each other through the through holes of the upper portion of the inner tube 3, and the inside of the inner tube 3 and the second heat medium partial chamber 34 located at the lower side communicate with each other through the through holes of the lower portion of the inner tube 3. Therefore, the heat medium having flowed into the medium inflow port 20 enters into the inner tube 3 (heat exchange chamber 3c) through the second heat medium partial chamber 34 located at the lower side, flows through gaps of the heat exchange pipes of the tube bundle 32, and then flows through the first heat medium partial chamber 33 located at the upper side and the medium outflow port 21 to the outside.

According to the above artificial lung device 1, venous blood taken out from a vein enters into the housing 2 through the blood inflow port 16 and enters into the heat exchange chamber 3c through the left openings of the heat exchange pipes of the tube bundle 32. The blood in the heat exchange chamber 3c flows through the right openings of the heat exchange pipe and the bridge portion 41, enters into the gas exchange chamber 45 from the right side of the gas exchange chamber 45, flows through the gas exchange chamber 45 to the left side, and is delivered through the blood outflow port 17 to the outside.

During this, in the heat exchange chamber 3c, heat exchange is performed between the heat medium having flowed through the medium inflow port 20 and the second heat medium partial chamber 34 into the heat exchange chamber 3c and the blood flowing in the heat exchange pipes of the tube bundle 32. Moreover, in the gas exchange chamber 45, the gas exchange is performed between the blood flowing through the gaps of the hollow fiber body 43 and the oxygen-rich gas flowing through the inner holes of the hollow fibers. Thus, the temperature of the blood having flowed into the artificial lung device 1 is adjusted to a predetermined temperature. In addition, carbon dioxide in the blood is reduced, and oxygen is added to the blood. With this, the blood as arterial blood flows out through the blood outflow port 17.

The artificial lung device 1 is of a horizontal type, and the blood flowing through the gas exchange chamber 45 flows in a substantially horizontal direction. In some cases, a small amount of bubbles having entered into the gas exchange chamber 45 from somewhere is mixed with the blood flowing through the gas exchange chamber 45. Such bubbles are basically absorbed when being brought into contact with the hollow fibers of the hollow fiber body 43, and most of the bubbles are removed. However, in some cases, the bubbles are not adequately absorbed in the hollow fibers while the blood flows through the hollow fiber body 43 once. Therefore, the artificial lung device 1 according to the present embodiment includes the straightening frame 56 by which a larger amount of bubbles are absorbed by the hollow fiber body 43.

Figure 3:
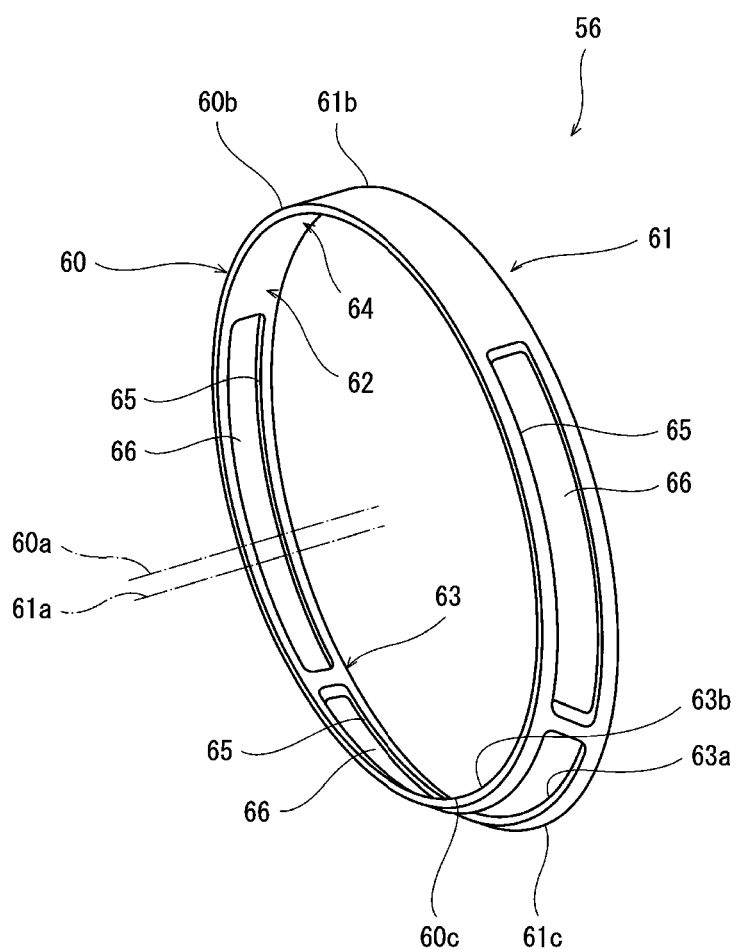
FIG. 3 is a perspective view showing a straightening frame included in the artificial lung device of FIG. 1 in the first disclosure.

FIG. 3 is a perspective view showing the straightening frame 56 included in the artificial lung device 1. The straightening frame 56 constitutes a bubble guide portion configured to guide the bubbles, which have flowed through the hollow fiber body 43 by the flow of the blood without being absorbed, toward the hollow fiber body 43 again. As shown in FIG. 3, the straightening frame 56 has a substantially annular shape and a substantially truncated cone shape.

Specifically, the straightening frame 56 includes a first opening 60 located at the left side and having a relatively small diameter and a second opening 61 located at the right side and having a relatively large diameter. Each of the first opening 60 and the second opening 61 has a circular shape. When the straightening frame 56 is assembled to the artificial lung device 1, the position of an upper end 60*b* of the first opening 60 in the upper-lower direction and the position of an upper end 61*b* of the second opening 61 in the upper-lower direction are substantially the same as each other, but a lower end 60*c* of the first opening 60 is located higher than a lower end 61*c* of the second opening 61. Moreover, the first opening 60 and the second opening 61 are spaced apart from each other in a left-right direction by a predetermined distance and are connected to each other by a straightening surface 62 that is a curved surface. Therefore, the straightening frame 56 has such a truncated cone shape that a center line 60*a* of the first opening 60 is located higher than a center line 61*a* of the second opening 61.

As shown in FIG. 2, the straightening frame 56 is provided in the outer peripheral space 55 such that: the first opening 60 located at the left side is fixed to the sealing member 50; and the second opening 61 located at the right side contacts the inner peripheral surface of the housing main body 11. As a result, the straightening surface 62 is provided in the outer peripheral space 55 so as to cross a passage extending from the gas exchange chamber 45 toward the blood outflow port 17. The straightening surface 62 is provided so as to be opposed to the outer peripheral surface of the hollow fiber body (gas exchanger) 43 and surround the hollow fiber body 43. As shown in FIG. 2, an upper portion of the straightening frame 56 is located substantially right under an opening of the air vent port 57 which opening is located close to the outer peripheral space 55, and a lower portion of the straightening frame 56 is located substantially right above an opening of the blood outflow port 17 which opening is located close to the outer peripheral space 55.

Moreover, the straightening surface 62 includes a first straightening surface 63 and a second straightening surface 64. The first straightening surface 63 is provided at a relatively lower side and is inclined such that a downstream portion (left portion in FIG. 2) 63*b* of the first straightening surface 63 in a flow direction of the blood is located closer to the outer peripheral surface of the hollow fiber body 43 than an upstream portion (right portion in FIG. 2) 63*a* of the first straightening surface 63 in the flow direction of the blood. Moreover, one or a plurality of openings 65 are formed at the first straightening surface 63, and filters 66 are provided at the respective openings 65. The filters 66 provided at the first straightening surface 63 are spaced apart from the outer peripheral surface of the hollow fiber body 43 and face an upstream side in the flow direction of the blood. With this, the blood having flowed through the hollow fiber body 43 flows through the filters 66 toward the blood outflow port 17. The filters 66 remove predetermined foreign matters mixed in the blood flowing through the filters 66, and known blood filters may be used. It should be noted that the filter structure may not include the straightening frame 56 and may be constituted by only the filter 66.

On the other hand, the second straightening surface 64 is provided at a relatively upper side. The second straightening surface 64 is located closer to the outer peripheral surface of the hollow fiber body 43 than the upstream portion 63*a* of the first straightening surface 63 and has a different inclination relative to the outer peripheral surface from the first straightening surface 63. In the present embodiment, in a sectional view, an upper end portion of the second straightening surface 64 forms a surface substantially parallel to the outer peripheral surface of the hollow fiber body 43. It should be noted that the second straightening surface 64 is also located so as to be spaced apart from the outer peripheral surface of the hollow fiber body 43. As shown in FIG. 2, the bubble storing portion 70 is formed between the second straightening surface 64 and the outer peripheral surface of the hollow fiber body 43. It should be noted that a filter is not provided at the second straightening surface 64. Moreover, the second straightening surface 64 is located higher than a portion which is located at the lower side of the straightening surface 62 and provided with one or a plurality of openings 65 (filters 66). According to this configuration, as compared to a case where the straightening frame 56 includes a filter at the upper side of the straightening surface 62, the bubbles can be more surely accumulated at the upper side of the second straightening surface 64 where the bubbles tend to be accumulated, and the bubbles can be more effectively prevented from flowing to the downstream side of the filters.

The straightening frame 56 according to the present embodiment is an example in which when the straightening surface 62 is substantially equally divided into four regions that are upper and lower portions and portions each between the upper and lower portions, the filters 66 are provided at three regions other than the upper portion. However, the positions where the filters 66 are provided are not limited to these. Each filter 66 can be provided at a suitable position and range other than the second straightening surface 64 that is the upper portion.

In the artificial lung device 1 including the straightening frame 56, the blood having flowed through the hollow fiber body 43 of the gas exchange chamber 45 flows through the filters 66 of the straightening frame 56 to the blood outflow port 17. At this time, the bubbles mixed in the blood are received by the straightening surface 62 of the straightening frame 56. The bubbles flow along the first straightening surface 63 from the upstream portion 63*a* to the downstream portion 63*b* or flow upward by buoyancy. As a result, in the process of flowing from the upstream portion 63a of the first straightening surface 63 to the downstream portion 63b of the first straightening surface 63, the bubbles approach the hollow fiber body 43. In addition, in the process of flowing upward from the first straightening surface 63 to the second straightening surface 64 by the buoyancy, the bubbles approach the hollow fiber body 43. Therefore, in the artificial lung device 1, the bubbles contained in the blood having flowed through the hollow fiber body 43 once can be made to flow toward the hollow fiber body 43 again by the straightening frame 56 and can be absorbed by the hollow fiber body 43.

Moreover, the artificial lung device 1 includes the bubble storing portion 70 between the second straightening surface 64 and the outer peripheral surface of the hollow fiber body 43. Therefore, even if a large amount of bubbles flow, the bubbles can be temporarily stored in the bubble storing portion 70. It should be noted that the first straightening surface 63 has a function of mainly guiding the bubbles to the hollow fiber body 43 (making the bubbles flow toward the hollow fiber body 43), and the second straightening surface 64 has a function of temporarily storing the guided bubbles and bringing the bubbles into contact with the hollow fiber body 43. Therefore, the second straightening surface 64 does not have to be accurately parallel to the outer peripheral surface of the hollow fiber body 43.

Embodiment 2 According to First Disclosure

FIGS. 4A and 4B are sectional views each showing a straightening frame 56A of an artificial lung device 1A according to Embodiment 2. More specifically, FIG. 4A is a sectional view showing portions including the entire straightening frame 56A in the artificial lung device 1A, and FIG. 4B is a sectional view showing portions including the upper portion of the straightening frame 56A in the artificial lung device 1A. The straightening frame 56A of the artificial lung device 1A includes a second straightening surface 64A at least a part of which is formed by an inner wall surface of the housing main body 11.

To be specific, Embodiment 1 has described a case where the entire straightening frame 56 is configured as a separate member independently from the housing main body 11. However, the configuration of the straightening frame 56 is not limited to this. More specifically, in the artificial lung device 1A shown in FIG. 4B, a wall portion 71 extends from a right end of an upper portion of the recess 54 of the housing main body 11 to the inside of the outer peripheral space 55 along the outer peripheral surface of the hollow fiber body 43. An inner peripheral surface 71A of the wall portion 71 constitutes (part of) a straightening surface 62A, and especially, an upper portion of the inner peripheral surface 71A constitutes the second straightening surface 64A.

Moreover, as shown in FIG. 4A, a width of the straightening frame 56A in the left-right direction in a front view is substantially constant from its upper portion to its lower portion. A projection amount of the wall portion 71 toward the left side decreases as the wall portion 71 extends from the upper portion to the lower portion. A portion 72 of the straightening frame 56A other than a portion constituted by the wall portion 71 is constituted as a separate member from the housing main body 11. A component corresponding to the first straightening surface 63 of Embodiment 1 is mainly constituted by the portion 72, and the filter 66 is provided at an opening (not shown) formed at the portion 72.

It should be noted that in the straightening frame 56A, a boundary between the portion constituted by the wall portion 71 and the portion 72 other than the above portion is set as a boundary line extending in a circumferential direction in the example of FIG. 4A. However, the boundary is not limited to this and may be set arbitrarily. Moreover, part of the straightening frame 56A is constituted by the wall portion 71, but the entire straightening frame 56A (except for the filter 66) may be constituted by the wall portion 71. It should be noted that in Embodiments 1 and 2 according to the first disclosure, a space is formed by an inside surface of the housing main body 11 (more specifically, an inside surface of the recess 54) as an opposing wall, an inside surface of the filter structure, and an outside surface of the hollow fiber body 43, and constitutes the bubble storing portion 70 or the bubble guide portion. In this case, the opposing wall may be provided at the filter structure.

According to this configuration, the positioning of the second straightening surface 64A and the outer peripheral surface of the hollow fiber body 43 when assembling the artificial lung device 1A can be more easily performed with a high degree of accuracy.

Embodiment 3 According to First Disclosure

Figure 5A:
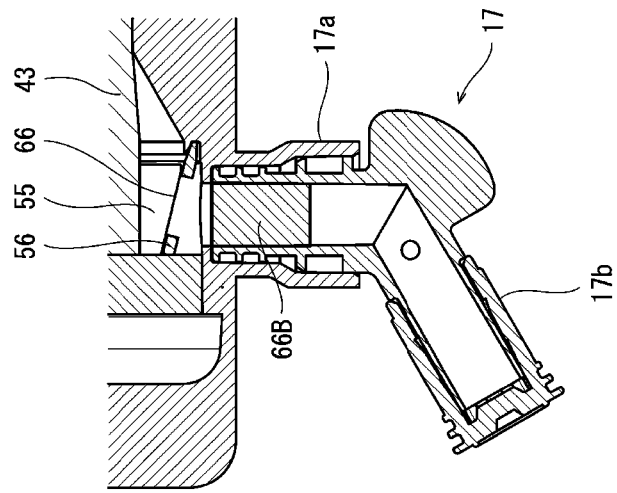
FIGS. 5A and 5B are partial sectional views showing a blood outflow port of the artificial lung device according to Embodiment 3 of the first disclosure.
Figure 5B:
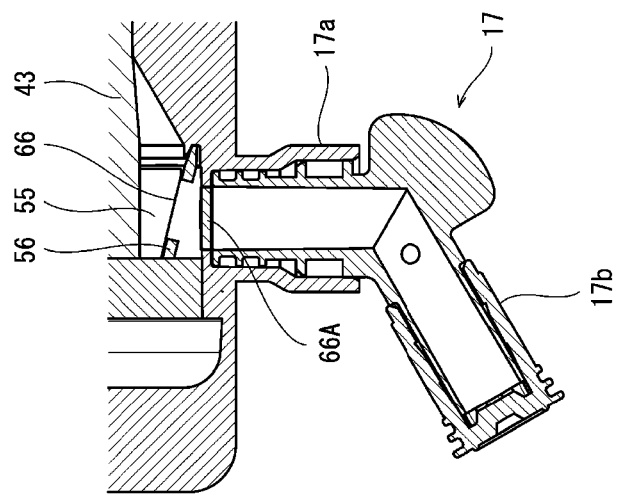

FIGS. 5A and 5B are sectional views showing the blood outflow port 17 of an artificial lung device 1B according to Embodiment 3. The following will describe a case where instead of or in addition to the filters 66 of the straightening frame 56 or 56A of Embodiment 1 or 2, a filter is provided at a different position.

As with Embodiments 1 and 2, the blood outflow port 17 shown in FIG. 5A includes the port attaching portion 17a and the port main body portion 17b. A filter 66A having a flat plate shape is provided at an opening of the port attaching portion 17a so as to cover the opening, the opening being located close to the inside of the housing main body 11. A periphery of the filter 66A may be fixed by a fixing member which is a member different from the filter 66A and fixes the filter 66A to the housing.

Moreover, as with Embodiments 1 and 2, the blood outflow port 17 shown in FIG. 5B includes the port attaching portion 17a and the port main body portion 17b. A filter 66B having a columnar shape is provided inside the port attaching portion 17a. The filter 66B has an outer diameter that is substantially equal to an inner diameter of the port attaching portion 17a and is inserted into the port attaching portion 17a so as to contact an inner peripheral surface of the port attaching portion 17a with almost no gap. Moreover, the size of the filter 66B in the flow direction of the blood in the blood outflow port 17 is larger than an inner diameter of the blood outflow port 17.

According to these filters 66A and 66B, foreign matters can be removed from the blood in the blood outflow port 17. Moreover, since the filter 66B shown in FIG. 5B can easily secure a large volume, a larger amount of foreign matters can be removed from the blood.

The following will describe Embodiments 1 to 8, Modified Examples 1 and 2, and Reference Example 1 according to the second disclosure.

Embodiment 1 According to Second Disclosure

Figure 6:
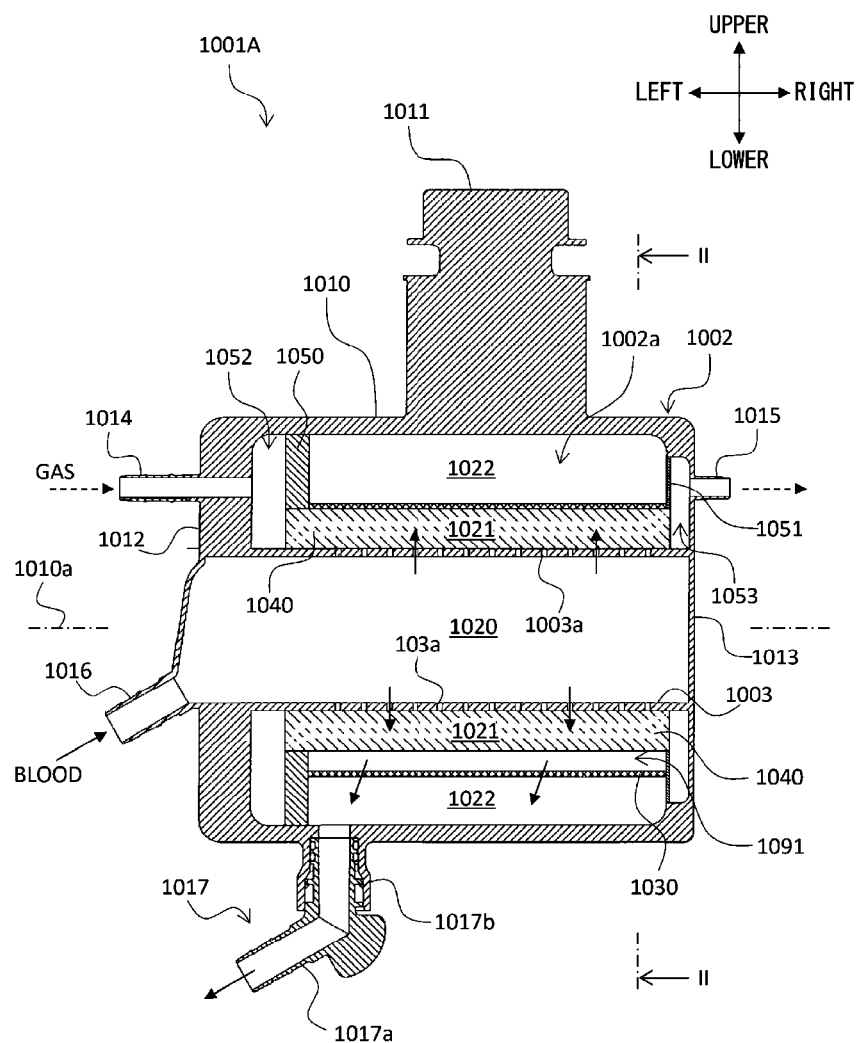
FIG. 6 is a front sectional view showing the artificial lung device according to Embodiment 1 of the second disclosure.
Figure 7:
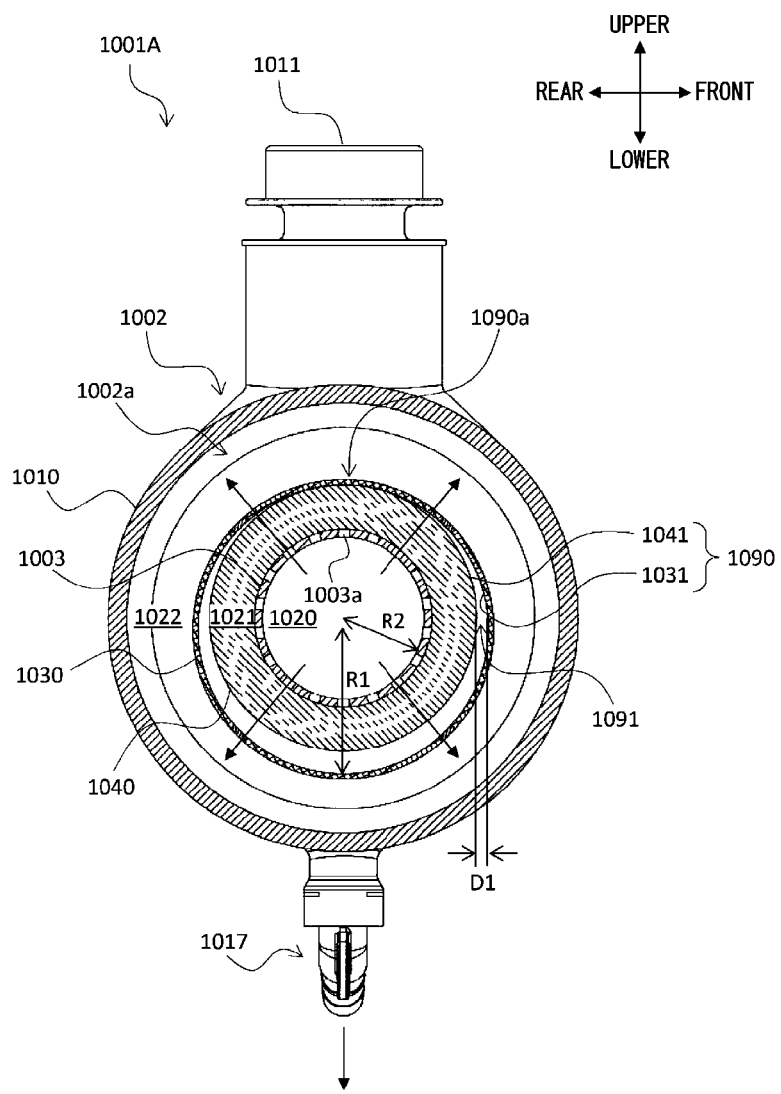
FIG. 7 is a side sectional view taken along line II-II in the artificial lung device of FIG. 6 in the second disclosure.

FIG. 6 is a front sectional view showing the configuration of an artificial lung device 1001A of Embodiment 1. FIG. 7 is a side sectional view taken along line II-II in the artificial lung device 1001A shown in FIG. 6. In a surgical operation performed after the movement of the heart of a patient is stopped, the artificial lung device 1001A shown in FIGS. 6 and 7 is used as a substitute for the function of the lung of the patient. Therefore, the artificial lung device 1001A has a gas exchange function of removing carbon dioxide contained in the blood of the patient and adding oxygen to the blood and a heat exchange function of adjusting the temperature of the blood. The artificial lung device 1001A in Embodiment 1 is of a so-called horizontal type and includes a housing 1002 and an inner tube 1003.

The housing 1002 is formed in a substantially cylindrical shape including both end portions that are closed. The housing 1002 includes an internal space 1002a accommodating the inner tube 1003. Moreover, the housing 1002 includes a housing main body 1010, a suspending portion 1011, and two cap portions 1012 and 1013.

The housing main body 1010 is formed in a substantially cylindrical shape, and the suspending portion 1011 is provided at an outer peripheral surface of an upper portion of the housing main body 1010. The suspending portion 1011 is arranged at a substantially middle portion of the housing main body 1010 which portion is located at a substantially middle position in a direction along an axis 1010a of the housing main body 1010. The suspending portion 1011 extends in the radially outward direction from the outer peripheral surface of the upper portion of the housing main body 1010. The suspending portion 1011 is formed in, for example, a substantially columnar shape and is suspended in such a manner that a tip end-side portion thereof is attached to an external suspending device (not shown). Therefore, the housing main body 1010 can be suspended through the suspending portion 1011, and the axis 1010a of the suspended housing main body 1010 extends in a horizontal direction.

The housing main body 1010 includes opening end portions at both sides in the direction along the axis 1010a. The opening end portion at one side (left side in FIG. 6) is closed by the cap portion 1012, and the opening end portion at the other side (right side in FIG. 6) is closed by the cap portion 1013. Each of the cap portions 1012 and 1013 is formed in a substantially circular plate shape. It should be noted that in the following description, for convenience of explanation, regarding the direction along the axis 1010a of the housing main body 1010, a side where the cap portion 1012 is located is referred to as a left side, and a side where the cap portion 1013 is located is referred to as a right side.

As shown in FIG. 6, a gas supply port 1014 is formed at the cap portion 1012. The gas supply port 1014 is formed in a substantially cylindrical shape and projects to the left side in the direction along the axis 1010a from the vicinity of an outer peripheral edge of the cap portion 1012. The gas supply port 1014 is connected to an external gas supply device (not shown) through a gas supply tube. Oxygen-containing gas supplied from the gas supply device is introduced through the gas supply port 1014 into the housing 1002.

A gas discharge port 1015 is formed at the cap portion 1013. The gas discharge port 1015 is formed in a substantially cylindrical shape and projects to the right side in the direction along the axis 1010a from the vicinity of an outer peripheral edge of the cap portion 1013. The gas discharge port 1015 is connected to the external gas supply device through a gas discharge tube. The gas supplied through the gas supply port 1014 into the housing 1002 is discharged through the gas discharge port 1015 and is returned to the gas supply device.

A blood inflow port 1016 is formed in the vicinity of a central axis (axis which substantially coincides with the axis 1010a of the housing main body 1010) of the cap portion 1012. The blood inflow port 1016 is formed in a substantially cylindrical shape and projects from a lower side of the central axis of the cap portion 1012 in a left and obliquely downward direction. A venous blood tube (not shown) is connected to the blood inflow port 1016, and venous blood is introduced through the venous blood tube and the blood inflow port 1016 into the housing main body 1010.

A blood outflow port 1017 is formed at a position of a lower portion (portion opposite to the suspending portion 1013) of the outer peripheral surface of the housing main body 1010 which position is located at the left side of a center of the artificial lung device 1001A in the direction along the axis 1010a. More specifically, the blood outflow port 1017 includes a port attaching portion 1017a and a port main body portion 1017b. The port attaching portion 1017a is formed in a substantially cylindrical shape. The port attaching portion 1017a is provided at the lower portion of the outer peripheral surface of the housing main body 1011 and projects downward. The port main body portion 1017b is inserted into the port attaching portion 1017a from a lower side. The port main body portion 1017b is formed in a substantially cylindrical shape. The port main body portion 1017b projects downward from a lower end of the port attaching portion 1017a and is bent in an obliquely downward direction at a tip side of the lower end of the port attaching portion 1017a. The port main body portion 1017b is rotatable relative to the port attaching portion 1017a about a center axis of the port attaching portion 1017a. Therefore, an outflow opening of the port main body portion 1017b can be directed in various directions. An arterial blood tube (not shown) is connected to the blood outflow port 1017 (port main body portion 1017b). The arterial blood generated in the artificial lung device 1001A is delivered through the arterial blood tube to an outside.

A medium inflow port and a medium outflow port (both not shown) are provided at the cap portion 1013. The medium inflow port and the medium outflow port are arranged so as to sandwich a central axis of the cap portion 1013 and be spaced apart from each other. The medium inflow port is connected to a medium supply tube (not shown), and a heat medium, such as hot water or cold water, from the medium supply tube is introduced through the medium inflow port into the housing 1002. The medium outflow port is connected to a medium discharge tube (not shown), and the heat medium in the housing 1002 is discharged through the medium outflow port and the medium discharge tube to the outside of the housing 1002.

The inner tube 1003 is accommodated in the internal space 1002a of the housing 1002 so as to be substantially coaxial with the housing main body 1010. The internal space 1002a of the housing 1002 is divided into a heat exchange chamber 1020, a gas exchange chamber 1021, and the like by the inner tube 1003. Specifically, the internal space of the inner tube 1003 constitutes the heat exchange chamber 1020. Moreover, a ring-shaped space between the inner tube 1003 and the housing main body 1010 is further divided into a small-diameter ring-shaped space and a large-diameter ring-shaped space by a below-described tubular filter structure 1030. The small-diameter ring-shaped space constitutes the gas exchange chamber 1021, and the large-diameter ring-shaped space constitutes the blood outflow space 1022. A hollow fiber body (gas exchanger) 1040 is provided in the gas exchange chamber 1021.

The hollow fiber body 1040 is formed in a substantially cylindrical shape (or a columnar shape including an internal space) and is constituted by a plurality of hollow fibers. Specifically, the hollow fiber body 1040 is configured such that a mat-shaped hollow fiber membrane (bundle) formed by making the plurality of hollow fibers intersect with each other and laminating the plurality of hollow fibers on each other is wound around an outer peripheral surface of the inner tube 1003. It should be noted that the bundle does not have to be directly wound around the outer peripheral surface of the inner tube 1003, but a cylindrical core member which is externally fitted to the inner tube 1003 may be prepared, and the bundle may be wound around the core member and then externally fitted to the inner tube 1003 together with the core member.

An annular sealing member 1050 is provided in a region located at the left side of the gas exchange chamber 1021 and the blood outflow space 1022 so as to be externally fitted to a left end portion of the hollow fiber body 1040. The sealing member 1050 forms a gas inflow space 1052 together with an inner peripheral surface of the cap portion 1012 and a left end surface of the hollow fiber body 1040, and the gas supply port 1014 communicates with the gas inflow space 1052. Moreover, an annular sealing member 1051 is provided in a region located at the right side of the gas exchange chamber 1021 and the blood outflow space 1022 so as to be externally fitted to a right end portion of the hollow fiber body 1040. The sealing member 1051 forms a gas outflow space 1053 together with an inner peripheral surface of the cap portion 1013 and a right end surface of the hollow fiber body 1040, and the gas discharge port 1015 communicates with the gas outflow space 1053.

The hollow fiber body 1040 is provided so as to extend between the gas inflow space 1052 and the gas outflow space 1053. The sealing member 1050 seals between the hollow fiber body 1040 and the housing 1002 in the entire circumferential direction at the left side of the blood outflow space 1022, and the sealing member 1051 seals between the hollow fiber body 1040 and the housing 1002 in the entire circumferential direction at the right side of the blood outflow space 1022. According to this configuration, the gas inflow space 1052 communicating with the gas supply port 1014 and the gas outflow space 1053 communicating with the gas discharge port 1015 communicate with each other through the inner holes of the plurality of hollow fibers constituting the hollow fiber body 1040.

In the hollow fiber body 1040, gaps are provided among the plurality of hollow fibers constituting the hollow fiber body 1040. In the gas exchange chamber 1021, blood flows through the gaps. Specifically, the blood introduced to the gas exchange chamber 1021 flows through the gaps in the hollow fiber body 1040 and flows in the radially outward direction about the axis 1010$a$ while contacting the hollow fibers. Oxygen-rich gas flows from an external gas supply device through the gas supply port 1014 and the gas inflow space 1052 into the inner holes of the hollow fibers. Therefore, when the blood having high carbon dioxide concentration contacts the hollow fibers, gas exchange is performed between the blood and the gas in the hollow fibers. With this, carbon dioxide is removed from the blood, and oxygen is added to the blood. As above, the blood flows in the radially outward direction in the gas exchange chamber 1021 while being subjected to the gas exchange. On the other hand, the gas flowing through the inner holes of the hollow fibers flows to the right side while being subjected to the gas exchange, and returns to the external gas supply device through the gas outflow space 1053 and the gas discharge port 1015.

As described above, the internal space of the inner tube 1003 constitutes the heat exchange chamber 1020. Medium pipe passages (not shown) are provided in the heat exchange chamber 1020. The medium inflow port is connected to first ends of the medium pipe passages, and the medium outflow port is connected to second ends of the medium pipe passages. The medium pipe passages are long and small-diameter pipe members made of a material, such as stainless steel, having high heat conductivity. A plurality of through holes 1003$a$ which penetrate the inner tube 1003 from inside to outside are provided at a wall portion of the inner tube 1003 over the entire periphery. The blood having flowed through the blood inflow port 1016 flows through gaps of the medium pipe passages and the through holes 1003$a$ of the inner tube 1003 to the gas exchange chamber 1021. As above, the blood flows radially from the heat exchange chamber 1020 to the gas exchange chamber 1021. While the blood flows through the heat exchange chamber 1020, the medium for temperature adjustment flows through the medium pipe passages from the medium inflow port. Therefore, the temperature of the blood which has contacted the medium pipe passages is adjusted to a suitable temperature. It should be noted that a heat exchanger provided in the heat exchange chamber 1020 is not limited to the medium pipe passages and is only required to be provided such that the blood having flowed through the blood inflow port 1016 is subjected to the heat exchange through the heat exchanger and is then subjected to the gas exchange by the hollow fiber membrane.

According to the above artificial lung device 1001A, venous blood taken out from a vein enters into the housing 1002 through the blood inflow port 1016, flows through the heat exchange chamber 1020 inside the inner tube 1003, the through holes 1003$a$ of the inner tube 1003, the gas exchange chamber 1021 outside the inner tube 1003, the filter structure 1030, and the blood outflow space 1022 in this order, and is delivered through the blood outflow port 1017 to the outside.

During this, in the heat exchange chamber 1020, the blood is subjected to heat exchange with the heat medium flowing through the medium pipe passages as described above, and therefore, the temperature of the blood is adjusted to a suitable temperature. Moreover, in the gas exchange chamber 1021, the gas exchange is performed between the blood flowing through the gaps of the hollow fiber body 1040 and the oxygen-rich gas flowing through the inner holes of the hollow fibers. Thus, temperature of the blood having flowed into the artificial lung device 1001A is adjusted to a predetermined temperature. In addition, carbon dioxide in the blood is reduced, and oxygen is added to the blood. With this, the blood as arterial blood flows out through the blood outflow port 1017.

The artificial lung device 1001A includes a bubble guide portion 1090 as a component which makes the hollow fibers absorb a larger amount of gas, such as bubbles, flowing together with the blood. To be specific, the artificial lung device 1001A includes an opposing wall which is arranged so as to be opposed to a surface 1041 of the hollow fiber body 1040 and forms a space (bubble storing portion) 1091 between the opposing wall and the surface 1041. A separation dimension D1 between the surface 1041 of the hollow fiber body 1040 and the opposing wall gradually decreases to become zero toward a vertically upper side. The surface 1041 of the hollow fiber body 1040 and the opposing wall which are formed such that the separation dimension D1 gradually decreases to zero constitute the bubble guide portion 1090 configured to guide the bubbles, which has flowed through the hollow fiber body 1040, to the hollow fiber body 1040 again. Moreover, in the artificial lung device 1001A, the filter structure 1030 constitutes the above opposing wall. Details will be described below.

The filter structure 1030 of the artificial lung device 1001A has a function of removing foreign matters in the blood. As shown in FIGS. 6 and 7, the filter structure 1030 is provided so as to cross a passage through which the blood having flowed through the hollow fiber body 1040 flows toward the blood outflow port 1017. More specifically, the filter structure 1030 is formed in a cylindrical shape, and an inner diameter R1 of the filter structure 1030 is larger than an outer diameter R2 of the cylindrical hollow fiber body 1040. Then, the filter structure 1030 is arranged eccentrically with respect to the hollow fiber body 1040 similarly formed in a cylindrical shape. Therefore, a portion of an inner peripheral surface 1031 of the filter structure 1030 which portion corresponds to an upper portion of the filter structure 1030 is in contact with a portion of an outer peripheral surface 1041 of the hollow fiber body 1040 which portion corresponds to an upper portion of the hollow fiber body 1040.

As a result, the space 1091 is formed between the outer peripheral surface 1041 of the hollow fiber body 1040 and the inner peripheral surface 1031 of the filter structure 1030 which constitutes the opposing wall opposed to the outer peripheral surface 1041. As shown in FIG. 7, the separation dimension D1 between the outer peripheral surface 1041 of the hollow fiber body 1040 and the inner peripheral surface 1031 of the filter structure 1030 gradually decreases toward the vertically upper side and becomes zero at a contact portion 1090a where the outer peripheral surface 1041 of the hollow fiber body 1040 and the inner peripheral surface 1031 of the filter structure 1030 contact each other. According to the artificial lung device 1001A of Embodiment 1, the bubble guide portion 1090 is constituted by the outer peripheral surface 1041 of the hollow fiber body 1040 and the inner peripheral surface 1031 of the filter structure 1030 which are formed such that the separation dimension D1 gradually decreases to zero. In other words, in Embodiment 1 according to the second disclosure, a space is constituted by the inside surface of the filter structure and the outside surface of the hollow fiber body 1040 and constitutes the bubble storing portion 1091 or the bubble guide portion.

According to the artificial lung device 1001A configured as above, even when there are bubbles which flowed through the hollow fiber body 1040 but were not absorbed, such bubbles flow upward in the bubble guide portion 1090 along the inner peripheral surface 1031 of the filter structure 1030 or the outer peripheral surface 1041 of the hollow fiber body 1040 by buoyancy. Then, since the space 1091 included in the bubble guide portion 1090 gradually decreases in width toward the upper side, the bubbles flowing upward are gradually and strongly pressed against the hollow fiber body 1040. On this account, a larger amount of bubbles can be absorbed by the hollow fiber body 1040, and therefore, the bubbles can be prevented from being excessively accumulated in the housing 1002.

It should be noted that a sectional shape of the filter structure 1030 is not limited to a circular shape shown in FIG. 7 and may be, for example, an oval shape, an elliptical shape, or a droplet shape. Furthermore, as long as the separation dimension D1 between the outer peripheral surface 1041 of the hollow fiber body 1040 and the inner peripheral surface 1031 of the filter structure 1030 gradually decreases to approach zero toward the vertically upper side as described above (i.e., as long as the bubble guide portion 1090 is included), the configuration of the other portion of the filter structure 1030 is not especially limited.

Embodiment 2 According to Second Disclosure

Figure 8:
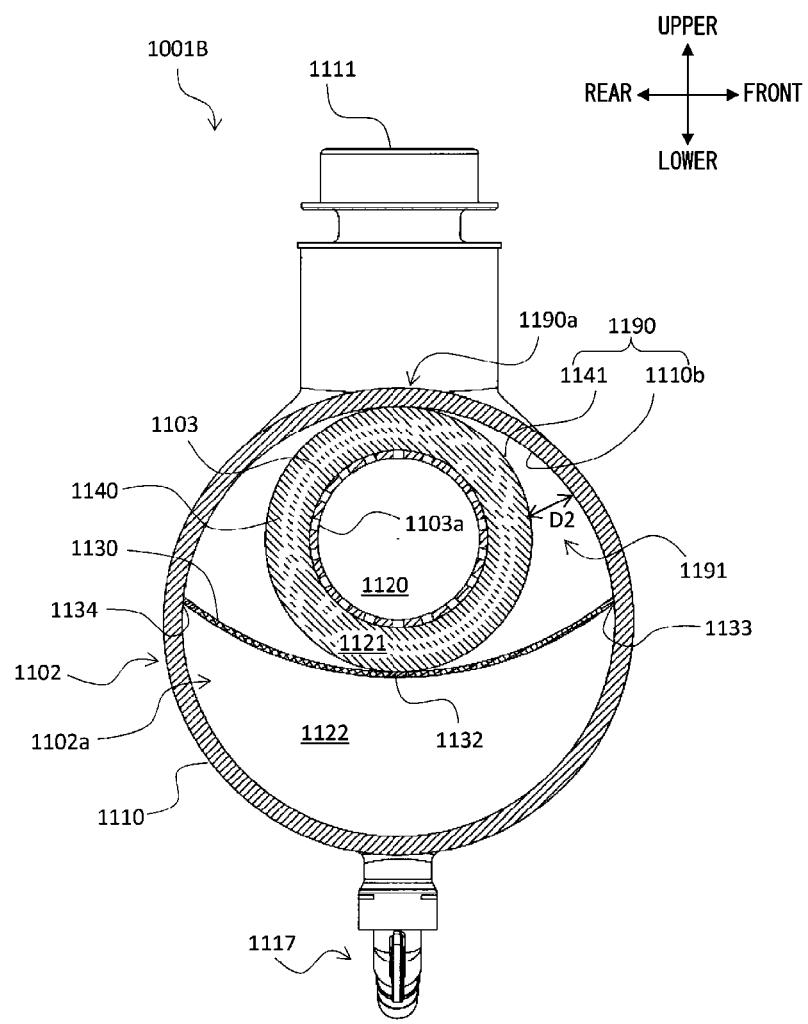
FIG. 8 is a side sectional view showing the artificial lung device according to Embodiment 2 of the second disclosure.

FIG. 8 is a side sectional view showing an artificial lung device 1001B according to Embodiment 2. Hereinafter, portions of the artificial lung device 1001B which portions are different from those of the artificial lung device 1001A will be mainly described. It should be noted that in FIG. 8, reference signs obtained by adding 100 to the reference signs used in the explanation of the artificial lung device 1001A are used for the components of the artificial lung device 1001B which components correspond to the components of the artificial lung device 1001A in terms of at least the functions.

As shown in FIG. 8, the artificial lung device 1001B is of a so-called horizontal type and includes a housing 1102 and an inner tube 1103. The housing 1102 includes a substantially cylindrical housing main body 1110, a suspending portion 1111, and two cap portions (not shown). The suspending portion 1111 is connected to an upper portion of the housing main body 1110, and the two cap portions close both end openings of the housing main body 1110.

The inner tube 1103 is accommodated in an internal space 1102a of the housing 1102 so as to be located at an upper side eccentrically with respect to a center axis of the housing main body 1110. Moreover, a cylindrical hollow fiber body (gas exchanger) 1140 is provided so as to be coaxially and externally fitted to the inner tube 1103. A portion of a surface 1141 of the hollow fiber body 1140 which portion corresponds to an upper portion of the hollow fiber body 1140 is in contact with a portion of an inner wall surface 1110b of the housing main body 1110 which portion corresponds to an upper portion of the housing main body 1110.

As a result, a space (bubble storing portion) 1191 is formed between the outer peripheral surface 1141 of the hollow fiber body 1140 and the inner wall surface 1110b of the housing main body 1110 which constitutes an opposing wall opposed to the outer peripheral surface 1141. As shown in FIG. 8, a separation dimension D2 between the outer peripheral surface 1141 of the hollow fiber body 1140 and the inner wall surface 1110b of the housing main body 1110 gradually decreases toward a vertically upper side and becomes zero at a contact portion 1190a where the outer peripheral surface 1141 of the hollow fiber body 1140 and the inner wall surface 1110b of the housing main body 1110 contact each other. In the artificial lung device 1001B according to Embodiment 2, a bubble guide portion 1190 is constituted by the outer peripheral surface 1141 of the hollow fiber body 1140 and the inner wall surface 1110b of the housing main body 1110 which are formed such that the separation dimension D2 gradually decreases to zero. In other words, in Embodiment 2 according to the second disclosure, a space is constituted by the inner wall of the housing, the inside surface of the filter structure 1130, and the outside surface of the hollow fiber body 1140 and constitutes the bubble guide portion 1190.

The internal space 1102a of the housing 1102 accommodates a filter structure 1130. The filter structure 1130 is formed in a rectangular plate shape in plan view, and a middle portion 1132 of the filter structure 1130 which portion is located at a middle position in a front-rear direction is formed in a curved shape so as to project downward in side view. An upper surface of the middle portion 1132 of the filter structure 1130 is in contact with the surface 1141 of the lower portion of the hollow fiber body 1140. A front end 1133 of the filter structure 1130 is in contact with a portion of the inner wall surface 1110b of the housing main body 1110 which portion is located at a front side and in the vicinity of a middle position in the upper-lower direction. A rear end 1134 of the filter structure 1130 is in contact with a portion of the inner wall surface 1110b of the housing main body 1110 which portion is located at a rear side and in the vicinity of a middle position in the upper-lower direction. It should be noted that the configuration of the filter structure 1130 is not limited to the above configuration, and another configuration may be adopted as long as the filter structure 1130 is provided so as to cross a passage through which the blood having flowed through the hollow fiber body 1140 flows toward the blood outflow port.

According to the artificial lung device 1001B, venous blood taken out from a vein enters into the housing 1102 through the blood inflow port (not shown), flows through a heat exchange chamber 1120 inside the inner tube 1103, through holes 1103a of the inner tube 1103, a gas exchange chamber 1121 outside the inner tube 1103, the filter structure 1130, and a blood outflow space 1122 in this order, and is delivered as arterial blood through the blood outflow port (not shown) to the outside. During this, as with the artificial lung device 1001A, the temperature of the blood is adjusted in the heat exchange chamber 1120, and carbon dioxide is removed from the blood and oxygen is added to the blood in the gas exchange chamber 1121.

Moreover, as described above, the artificial lung device 1001B includes the bubble guide portion 1190. Therefore, even when there are bubbles which flowed through the hollow fiber body 1140 but were not absorbed, such bubbles flow upward in the bubble guide portion 1190 along the inner wall surface 1110b of the housing main body 1110 or the outer peripheral surface 1141 of the hollow fiber body 1140 by buoyancy. Then, since the space 1191 included in the bubble guide portion 1190 gradually decreases in width toward the upper side, the bubbles flowing upward are gradually and strongly pressed against the hollow fiber body 1140. On this account, a larger amount of bubbles can be absorbed by the hollow fiber body 1140, and therefore, the bubbles can be prevented from being excessively accumulated in the housing 1102.

Embodiment 3 According to Second Disclosure

Figure 9:
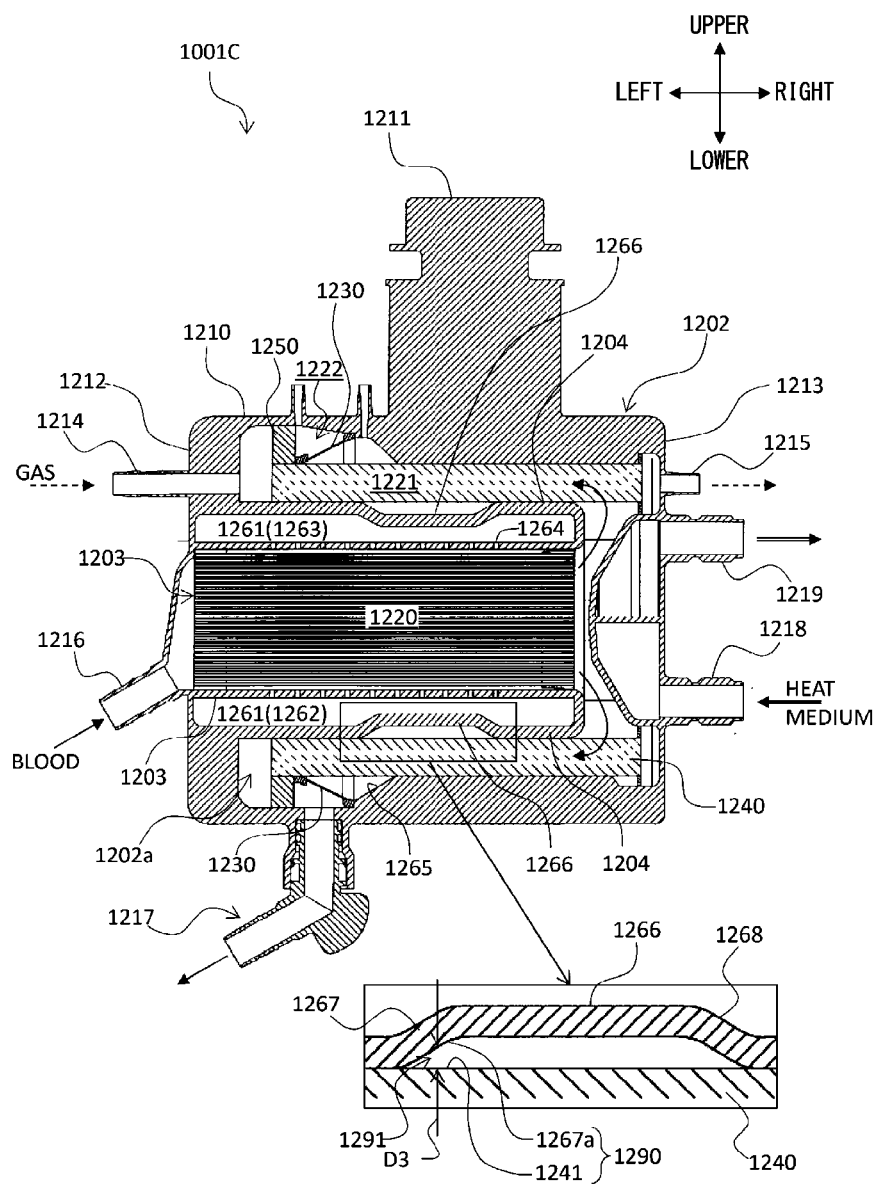
FIG. 9 is a front sectional view showing the artificial lung device according to Embodiment 3 of the second disclosure.

FIG. 9 is a front sectional view showing an artificial lung device 1001C according to Embodiment 3. Hereinafter, portions of the artificial lung device 1001C which portions are different from those of the artificial lung device 1001A will be mainly described. It should be noted that in FIG. 9, reference signs obtained by adding 200 to the reference signs used in the explanation of the artificial lung device 1001A are used for the components of the artificial lung device 1001C which components correspond to the components of the artificial lung device 1001A in terms of at least the functions.

As shown in FIG. 9, the artificial lung device 1001C is of a so-called horizontal type and includes a housing 1202, an inner tube 1203, and a middle tube 1204. The middle tube 1204 is smaller in diameter than the housing 1202 and larger in diameter than the inner tube 1203. The inner tube 1203 and the middle tube 1204 are accommodated in an internal space 1202a of the housing 1202 so as to be arranged substantially coaxially with each other.

The inside of the inner tube 1203 constitutes a heat exchange chamber 1220. A tube bundle 1260 is arranged in the heat exchange chamber 1220 such that an axial direction of the tube bundle 1260 coincides with an axial direction of the inner tube 1203. The tube bundle 1260 is an assembly of a plurality of heat exchange pipes. The pipes are made of a material, such as stainless steel, having high heat conductivity. The blood from a blood inflow port 1216 flows in the pipes through left openings of the pipes.

An annular heat medium chamber 1261 is formed between the inner tube 1203 and the middle tube 1204. The heat medium chamber 1261 is divided into a first heat medium chamber 1262 located at the lower side and a second heat medium chamber 1263 located at the upper side. A medium inflow port 1218 communicates with the first heat medium chamber 1262, and a medium outflow port 1219 communicates with the second heat medium chamber 1263. Moreover, a plurality of through holes 1264 are formed at each of upper and lower portions of the inner tube 1203. Furthermore, the tube bundle 1260 in the inner tube 1203 is supported such that gaps are formed among the heat exchange pipes.

Therefore, the medium having flowed through the medium inflow port 1218 flows through the first heat medium chamber 1262 and the through holes 1264 of the lower portion of the inner tube 1203 to the inside of the inner tube 1203. Then, the medium flows through the gaps of the plurality of heat exchange pipes constituting the tube bundle 1260 and the through holes 1264 of the upper portion of the inner tube 1203 to the second heat medium chamber 1263 and further flows therefrom through the medium outflow port 1219 to the outside. On the other hand, the blood having flowed through the blood inflow port 1216 flows through the inner holes of the heat exchange pipes of the tube bundle 1260. Therefore, during this, the heat exchange between the blood and the medium is performed, and thus, the temperature of the blood is adjusted to a suitable temperature. It should be noted that the present embodiment is not limited to the configuration in which the through holes 1264 are provided at the upper and lower portions of the inner tube 1203. For example, the through holes 1264 may be provided at opposing positions of a side portion of the inner tube 1203 such that the medium flows in a direction from a paper surface near side to a paper surface deep side or in a direction from the paper surface deep side to the paper surface near side.

The blood having been adjusted in temperature in the heat exchange chamber 1220 flows out through right openings of the tube bundle 1260, flows in the radially outward direction in the vicinity of a right end of the inner tube 1203, and reaches a gas exchange chamber 1221 formed outside and around the middle tube 1204. More specifically, the gas exchange chamber 1221 is formed between the middle tube 1204 and a housing main body 1210, and a tubular hollow fiber body (gas exchanger) 1240 is provided in the gas exchange chamber 1221 so as to be externally fitted to the middle tube 1204.

The hollow fiber body 1240 includes a plurality of hollow fibers. Left openings of the inner holes of the hollow fibers communicate with a gas supply port 1214, and right openings of the inner holes of the hollow fibers communicate with a gas discharge port 1215. Moreover, gaps are provided among the hollow fibers, and the blood flows through the gaps. To be specific, the blood having flowed out from the heat exchange chamber 1220 flows into the gas exchange chamber 1221 from the right side of the gas exchange chamber 1221 and flows through the gaps of the hollow fiber to the left side. During this, oxygen-rich gas flows through the inner holes of the hollow fibers, and gas exchange is performed between the blood and the gas. As a result, carbon dioxide is removed from the blood, and oxygen is added to the blood.

A recess 1265 is formed at a left portion of an inner peripheral surface of the housing main body 1210 so as to be larger in diameter than the other portion of the inner peripheral surface of the housing main body 1210. The recess 1265 is located so as to surround a left portion of the hollow fiber body 1240. A filter structure 1230 having an annular shape and a truncated cone shape is arranged between the recess 1265 and the hollow fiber body 1240. The filter structure 1230 is arranged so as to cross a passage through which the blood having flowed through the hollow fiber body 1240 flows toward a blood outflow port 1217. Therefore, a space defined by the recess 1265 and the hollow fiber body 1240 is divided into two spaces by the filter structure 1230, and one of the two spaces which communicates with the blood outflow port 1217 constitutes a blood outflow space 1222.

Therefore, as described above, foreign matters in the blood having been subjected to the gas exchange in the gas exchange chamber 1221 are removed when the blood flows through the filter structure 1230. The blood which has become the arterial blood as above flows through the blood outflow space 1222 and the blood outflow port 1217 to the outside. In other words, in Embodiment 3 according to the second disclosure, a space is constituted by the inner wall (first opposing wall) of the housing main body 1210, the inside surface of the filter structure 1230, and the outside surface of the hollow fiber body 1240 and constitutes a first bubble storing portion or a first bubble guide portion. In this case, the first opposing wall may be provided at the filter structure.

In the artificial lung device 1001C, a space (second bubble guide portion 1290) is constituted by the middle tube 1204 and the hollow fiber body 1240. More specifically, as shown in FIG. 9, a reduced-diameter portion 1266 is formed at a middle portion of the middle tube 1204 which portion is located at a middle position in the left-right direction. The reduced-diameter portion 1266 is reduced in diameter so as to be smaller in diameter than the other portion of the middle tube 1204. The reduced-diameter portion 1266 is provided so as to surround the middle portion of the middle tube 1204. The blood between the reduced-diameter portion 1266 and the hollow fiber body 1240 flows to the left side as with the blood in the hollow fiber body 1240. Moreover, a left portion of the reduced-diameter portion 1266 constitutes a tapered portion 1267 which has a tapered sectional contour so as to increase in diameter toward the left side, and a right portion of the reduced-diameter portion 1266 constitutes a tapered portion 1268 which has a tapered sectional contour so as to increase in diameter toward the right side.

The bubble guide portion 1290 is constituted by the left tapered portion 1267 of the reduced-diameter portion 1266 of the middle tube 1204 and the hollow fiber body 1240. To be specific, the left tapered portion 1267 constitutes a second opposing wall according to the present invention. The tapered portion 1267 is located so as to be opposed to an inner surface 1241 of the hollow fiber body 1240 and forms a space (second bubble storing portion) 1291 between the tapered portion 1267 and the inner surface 1241 of the hollow fiber body 1240. Moreover, a separation dimension D3 between an outer surface 1267a of the tapered portion 1267 and the inner surface 1241 of the hollow fiber body 1240 gradually decreases to become zero toward a downstream side (i.e., the left side) in the flow direction of the blood in the space 1291. In the artificial lung device 1001C, the bubble guide portion 1290 is formed as a ring-shaped groove surrounding the middle tube 1204. In other words, in Embodiment 3 according to the second disclosure, a space is constituted by the inner wall (second opposing wall) of the housing main body 1210 and the inner surface of the hollow fiber body 1240 and constitutes the second bubble storing portion 1290 or the second bubble guide portion 1291.

According to this configuration, even when there are bubbles which flowed through the hollow fiber body 1240 but were not absorbed, such bubbles move in the bubble guide portion 1290 toward the downstream side in the flow direction of the blood along the outer peripheral surface 1267a of the tapered portion 1267 or the inner peripheral surface 1241 of the hollow fiber body 1240. Since the space 1291 included in the bubble guide portion 1290 gradually decreases in width toward the downstream side, the bubbles moving toward the downstream side are gradually pressed against the hollow fiber body 1240. On this account, a larger amount of bubbles can be absorbed by the hollow fiber body 1240, and therefore, the bubbles can be prevented from being excessively accumulated in the housing 1202.

It should be noted that in FIG. 9, the reduced-diameter portion 1266 is formed to have a trapezoidal section but is not limited to this. For example, the reduced-diameter portion 1266 may be formed to have a triangular section including an oblique side which increases in diameter toward the downstream side in the flow direction of the blood or may be formed to have a circular-arc section.

Embodiment 4 According to Second Disclosure

Figure 10:
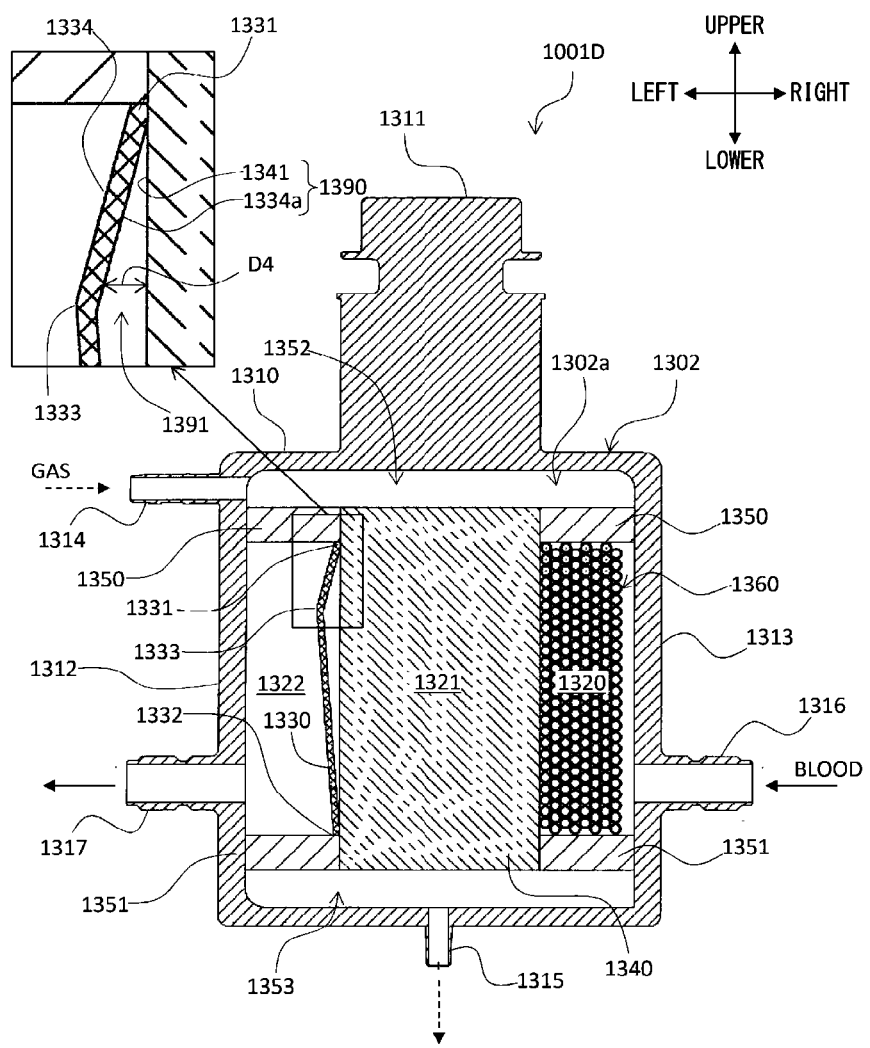
FIG. 10 is a front sectional view showing the artificial lung device according to Embodiment 4 of the second disclosure.

FIG. 10 is a front sectional view showing an artificial lung device 1001D according to Embodiment 4. Hereinafter, portions of the artificial lung device 1001D which portions are different from those of the artificial lung device 1001A will be mainly described. It should be noted that in FIG. 10, reference signs obtained by adding 300 to the reference signs used in the explanation of the artificial lung device 1001A are used for the components of the artificial lung device 1001D which components correspond to the components of the artificial lung device 1001A in terms of at least the functions.

As shown in FIG. 10, the artificial lung device 1001D includes a box-shaped housing 1302. The housing 1302 includes: a rectangular and tubular housing main body 1310 including left and right openings; a suspending portion 1311 connected to an upper portion of the housing main body 1310; and two cap portions 1312 and 1313 which respectively close the left and right openings of the housing main body 1310. The artificial lung device 1001D is configured such that in an internal space 1302a of the housing 1302, the blood flows in the left-right direction, the heat medium flows in the front-rear direction, and the gas flows in the upper-lower direction. Hereinafter, details of such configuration will be described.

The artificial lung device 1001D includes: a blood inflow port 1316 into which the venous blood flows; and a blood outflow port 1317 from which the blood having been adjusted in temperature and subjected to the gas exchange in the artificial lung device 1001D flows out as the arterial blood. The blood inflow port 1316 is provided at a position of the right cap portion 1313 which position is located lower than a middle position in the upper-lower direction. The blood outflow port 1317 is provided at a position of the left cap portion 1314 which position is located lower than a middle position in the upper-lower direction. It should be noted that in FIG. 10, the position of the blood inflow port 1316 and the position of the blood outflow port 1317 coincide with each other in the upper-lower direction. However, the present embodiment is not limited to this. The positions of the blood inflow port 1316 and the blood outflow port 1317 in the upper-lower direction or the front-rear direction may be made different from each other.

Moreover, the artificial lung device 1001D includes: a gas supply port 1314 into which oxygen-rich gas used for the gas exchange with the blood flows; and a gas discharge port 1315 from which the gas having been subjected to the gas exchange flows out. The gas supply port 1314 is provided at an upper portion of the left cap portion 1312, and the gas discharge port 1315 is provided in the vicinity of a middle position of a bottom wall of the housing main body 1310. An upper portion of the internal space 1302a of the housing 1302 constitutes a gas inflow space 1352 communicating with the gas supply port 1314, and a lower portion of the internal space 1302a constitutes a gas outflow space 1353 communicating with the gas discharge port 1315. Each of the gas inflow space 1352 and the gas outflow space 1353 forms a space shape that is flat in the upper-lower direction. A heat exchange chamber 1320, a gas exchange chamber 1321, and a blood outflow space 1322 are formed between the gas inflow space 1352 and the gas outflow space 1353.

A hollow fiber body (gas exchanger) 1340 having a rectangular solid shape is provided between the gas inflow space 1352 and the gas outflow space 1353. A dimension of the hollow fiber body 1340 in the front-rear direction is equal to an inside dimension of the housing main body 1310 in the front-rear direction, and a dimension of the hollow fiber body 1340 in the left-right direction is smaller than a distance between inner surfaces of the cap portions 1312 and 1313. Therefore, front and rear surfaces of the hollow fiber body 1340 are respectively in contact with front and rear inner surfaces of the housing main body 1310. On the other hand, the hollow fiber body 1340 is provided in the vicinity of a middle position in the left-right direction so as to be separated from the cap portions 1312 and 1313 in the left-right direction.

Then, a sealing member 1350 is provided so as to connect between an upper end portion of the hollow fiber body 1340 and inner surfaces of the cap portions 1312 and 1313, and a sealing member 1351 is provided so as to connect between a lower end portion of the hollow fiber body 1340 and the inner surfaces of the cap portions 1312 and 1313. Therefore, a lower portion of the gas inflow space 1352 is defined by an upper end portion of the hollow fiber body 1340 and an upper end portion of the sealing member 1350, and an upper portion of the gas outflow space 1353 is defined by a lower end portion of the hollow fiber body 1340 and a lower end portion of the sealing member 1351.

Moreover, a plurality of hollow fibers constituting the hollow fiber body 1340 extend substantially in the upper-lower direction. Upper end portions of the plurality of hollow fibers are open at the gas inflow space 1352, and lower end portions of the plurality of hollow fibers are open at the gas outflow space 1353. Therefore, the gas having flowed into the gas supply port 1314 enters from the gas inflow space 1352 through upper end openings of the hollow fibers of the hollow fiber body 1340 into the inner holes of the hollow fibers of the hollow fiber body 1340, flows through lower end openings of the hollow fibers of the hollow fiber body 1340 to the gas outflow space 1353, and is discharged through the gas discharge port 1315 to the outside. Moreover, gaps exist among the hollow fibers, and the blood flows through the gaps. Then, the gas exchange is performed between the blood flowing through the gaps and the gas flowing through the inner holes of the hollow fibers. Therefore, a space in which the hollow fiber body 1340 is provided constitutes the gas exchange chamber 1321.

The heat exchange chamber 1320 is formed in a space located at the right side of the hollow fiber body 1340, i.e., a space defined by a right side surface of the hollow fiber body 1340, an inner surface of the right cap portion 1313, a lower surface of the sealing member 1350, and an upper surface of the sealing member 1351.

A tube bundle 1360 constituted by an assembly of a plurality of heat exchange pipes is arranged in the heat exchange chamber 1320 such that axes of the pipes extend in the front-rear direction. The tube bundle 1360 is provided so as to block between the blood inflow port 1316 and the hollow fiber body 1340. A medium inflow port (not shown) is provided at one of front and rear walls of the housing main body 1310 and communicates with openings of a first end of the tube bundle 1360. A medium outflow port (not shown) is provided at the other of the front and rear walls of the housing main body 1310 and communicates with openings of a second end of the tube bundle 1360.

Therefore, the heat medium having flowed into the medium inflow port enters into the pipes from the openings of the first end of the tube bundle 1360 and flows inside the pipes. The heat medium flows out from the openings of the second end of the tube bundle 1360 and then flows out through the medium outflow port to the outside. Moreover, gaps are provided among the heat exchange pipes, and the blood flows through the gaps. Then, the heat exchange is performed between the blood flowing through the gaps and the medium flowing through the pipes. Therefore, a space in which the tube bundle 1360 is provided constitutes the heat exchange chamber 1320.

Moreover, a filter structure 1330 and the blood outflow space 1322 are provided in a space located at the left side of the hollow fiber body 1340, i.e., a space defined by a left side surface of the hollow fiber body 1340, an inner surface of the left cap portion 1312, the lower surface of the sealing member 1350, and the upper surface of the sealing member 1351.

To be specific, the filter structure 1330 having a rectangular sheet shape is provided along the left side surface of the hollow fiber body 1340. It should be noted that the filter structure 1330 is bent such that an upper portion thereof projects toward the left side. In other words, an upper end 1331 of the filter structure 1330 is in contact with the left side surface of an upper portion of the hollow fiber body 1340, and a lower end 1332 of the filter structure 1330 is in contact with the left side surface of a lower portion of the hollow fiber body 1340. Moreover, a bent portion 1333 of the filter structure 1330 is provided at a predetermined position located higher than a middle position in the upper-lower direction, and the bent portion 1333 is located away from the left side surface of the hollow fiber body 1340 toward the left side. Therefore, as shown in FIG. 10, a space defined by the hollow fiber body 1340 and the filter structure 1330 has a triangular shape having apexes that are the upper end 1331, the lower end 1332, and the bent portion 1333. It should be noted that the shape of the filter structure 1330 is not limited to the triangular shape and may be a dome shape that projects in a circular-arc shape toward the left side. Moreover, as shown in FIG. 10, a lower portion of the filter structure 1330 may be provided close to the left side surface of the hollow fiber body 1340. However, the present embodiment is not limited to this. The lower portion of the filter structure 1330 may have such a shape as to extend in the lower direction without contacting the left side surface of the hollow fiber body 1340 or may have such a shape as to spread toward the left side away from the left side surface of the hollow fiber body 1340.

Moreover, a space located at the left side of the filter structure 1330 in the space located at the left side of the hollow fiber body 1340 constitutes the blood outflow space 1322, and the blood outflow space 1322 communicates with the blood outflow port 1317. Therefore, after foreign matters in the blood having flowed through the gas exchange chamber 1321 are removed by the filter structure 1330, the blood flows through the blood outflow space 1322 and is discharged through the blood outflow port 1317 to the outside.

In the artificial lung device 1001D, a bubble guide portion 1390 is constituted by the filter structure 1330 and the hollow fiber body 1340. Specifically, as shown in FIG. 10, the filter structure 1330 includes an inclined surface 1334 at a portion connecting the upper end 1331 and the bent portion 1333. The inclined surface 1334 constitutes the opposing wall according to the present invention. To be specific, the inclined surface 1334 is located so as to be opposed to a left side surface 1341 of the hollow fiber body 1340 and forms a space (bubble storing portion) 1391 between the inclined surface 1334 and the left side surface 1341 of the hollow fiber body 1340. Moreover, a separation dimension D4 between a right side surface 1334a of the inclined surface 1334 and the left side surface 1341 of the hollow fiber body 1340 gradually decreases to become zero toward the vertically upper side.

According to this configuration, even when there are bubbles which flowed through the hollow fiber body 1340 but were not absorbed, such bubbles flow upward in the bubble guide portion 1390 along the right side surface 1334a of the inclined surface 1334 of the filter structure 1330 or the left side surface 1341 of the hollow fiber body 1340 by buoyancy of the bubbles. Since the space 1391 included in the bubble guide portion 1390 gradually decreases in width toward the upper side, the bubbles flowing upward gradually approach the hollow fiber body 1340. On this account, a larger amount of bubbles can be absorbed by the hollow fiber body 1340, and therefore, the bubbles can be prevented from being excessively accumulated in the housing 1302.

In other words, in Embodiment 4 according to the second disclosure, a space is constituted by the inside surface of the filter structure 1330 and the outer surface of the hollow fiber body 1340 and constitutes the bubble guide portion 1390 or the bubble storing portion 1391.

Embodiment 5 According to Second Disclosure

Figure 11:
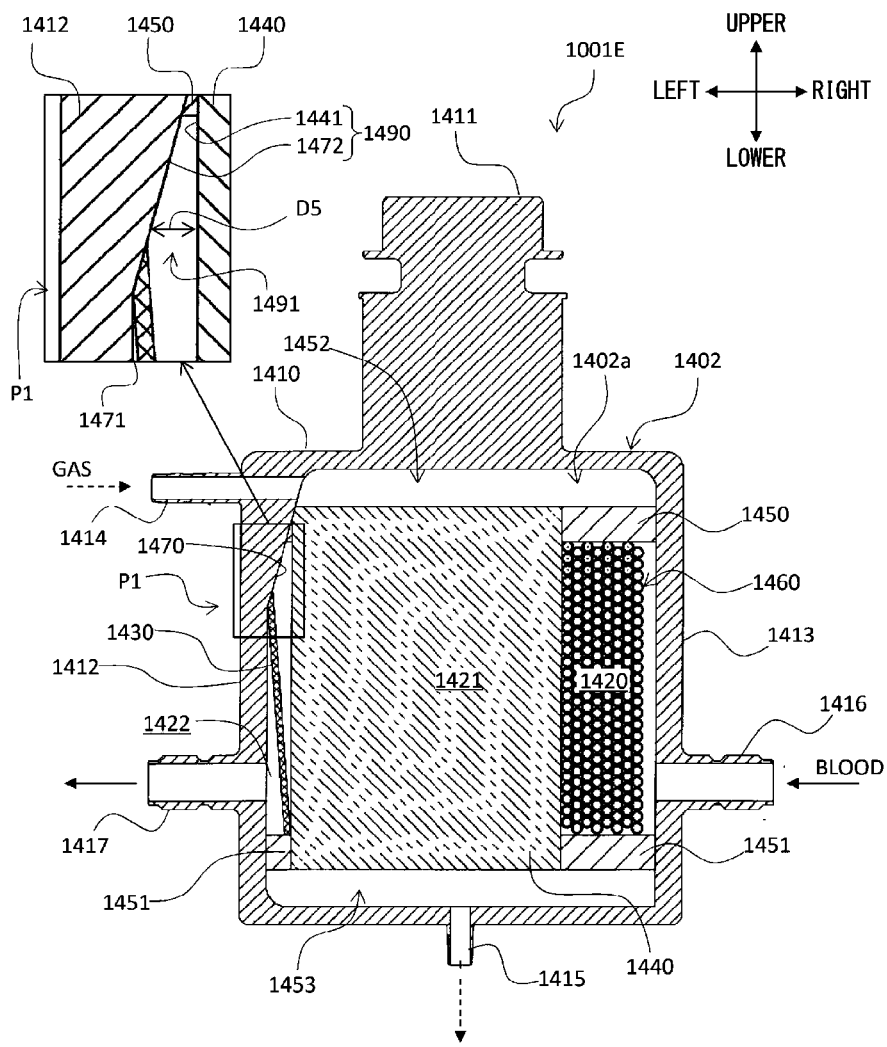
FIG. 11 is a front sectional view showing the artificial lung device according to Embodiment 5 of the second disclosure.

FIG. 11 is a front sectional view showing an artificial lung device 1001E according to Embodiment 5. Hereinafter, portions of the artificial lung device 1001E which portions are different from those of the artificial lung device 1001D will be mainly described. It should be noted that in FIG. 11, reference signs each obtained by replacing "3" that is the third digit (except for the alphabetical letter) in the reference signs used in the explanation of the artificial lung device 1001D with "4" are used for the components of the artificial lung device 1001E which components correspond to the components of the artificial lung device 1001E in terms of at least the functions.

As shown in FIG. 11, the artificial lung device 1001E includes a box-shaped housing 1402. The housing 1402 includes: a rectangular and tubular housing main body 1410 including left and right openings; a suspending portion 1411 connected to an upper portion of the housing main body 1410; and two cap portions 1412 and 1413 which respectively close the left and right openings of the housing main body 1410.

As with the artificial lung device 1001D, the artificial lung device 1001E is configured such that in an internal space 1402a of the housing 1402, the blood flows in the left-right direction, the heat medium flows in the front-rear direction, and the gas flows in the upper-lower direction. To be specific, the blood flows into a blood inflow port 1416 connected to the right cap portion 1413, flows in the left direction, flows through a heat exchange chamber 1420, a gas exchange chamber 1421, a filter structure 1430, and a blood outflow space 1422 in this order, and flows to the outside through a blood outflow port 1417 connected to the left cap portion 1412. The heat medium enters into openings of a first end of a tube bundle 1460 through a medium inflow port (not shown), flows inside the pipes in the front-rear direction, flows out through openings of a second end of the tube bundle 1460, and flows through a medium outflow port (not shown) to the outside. The gas for the gas exchange flows into a gas inflow space 1452 through a gas supply port 1414 located at the upper side, enters into inner holes of hollow fibers of a hollow fiber body 1440 through upper end openings of the inner holes of the hollow fibers, flows through lower end openings of the inner holes of the hollow fibers into a gas outflow space 1453, and is discharged through a gas discharge port 1415 to the outside.

It should be noted that: the blood flows through gaps of the pipes of the tube bundle 1460 in the heat exchange chamber 1420, and while flowing through the gaps of the pipes, the temperature of the blood is adjusted; and the blood flows through the gaps of the hollow fibers of the hollow fiber body 1440 in the gas exchange chamber 1421, and while flowing through the gaps of the hollow fibers, the blood is subjected to the gas exchange. Moreover, the blood having flowed through the hollow fiber body 1440 further passes through the filter structure 1430 arranged at the left side of the hollow fiber body 1440 (i.e., at the downstream side of the hollow fiber body 1440 in the flow direction of the blood) and then flows through the blood outflow space 1422 to the blood outflow port 1417.

An inner surface 1470 of the left cap portion 1412 is located so as to be opposed to a left side surface 1441 of the hollow fiber body 1440. It should be noted that a portion of the inner surface 1470 which portion extends from a lower end to a predetermined position P1 located higher than a middle position in the upper-lower direction constitutes a vertical surface 1471 extending substantially along the vertical direction. On the other hand, an upper portion of the inner surface 1470 which portion is located higher than the position P1 constitutes an inclined surface 1472 which extends toward the right side as it extends upward. Therefore, a separation dimension between the vertical surface 1471 located at the lower side in the inner surface 1470 of the cap portion 1412 and the hollow fiber body 1440 is substantially constant at any position in the upper-lower direction. On the other hand, a separation dimension D5 between the inclined surface 1472 located at the upper side of the position P1 and the hollow fiber body 1440 gradually decreases to become zero toward the vertically upper side. A space (bubble storing portion) 1491 is formed between the inclined surface 1472 and the hollow fiber body 1440. Therefore, the inclined surface 1472 constitutes the opposing wall according to the present invention, and a bubble guide portion 1490 is constituted by the inclined surface 1472 and the left side surface 1441 of the hollow fiber body 1440.

The filter structure 1430 is formed in a rectangular flat sheet shape. The filter structure 1430 is provided such that: an upper end thereof is located at a portion (connection portion where the vertical surface 1471 and the inclined surface 1472 are connected to each other) of the inner surface 1470 of the cap portion 1412 which portion corresponds to the position P1; and a lower end thereof is located at a connection portion where a lower portion of the hollow fiber body 1440 and a sealing member 1451 are connected to each other. To be specific, the filter structure 1430 is provided so as to cross a passage through which the blood having flowed through the hollow fiber body 1440 flows toward the blood outflow port 1417, and foreign matters are removed from the blood passing through the filter structure 1430. It should be noted that the shape of the filter structure 1430 is not limited to the shape shown in FIG. 11 and may be an arch shape projecting to the left side. Moreover, as shown in FIG. 11, a lower portion of the filter structure 1430 may be provided close to the left side surface of the hollow fiber body 1440. However, the present embodiment is not limited to this. The lower portion of the filter structure 1430 may have such a shape as to extend in the lower direction without contacting the left side surface of the hollow fiber body 1440.

According to this configuration, even when there are bubbles which flowed through the hollow fiber body 1440 but were not absorbed, such bubbles flow upward in the bubble guide portion 1490 along the inclined surface 1472 of the cap portion 1412 or the left side surface 1441 of the hollow fiber body 1440 by buoyancy of the bubbles. Since the space 1491 included in the bubble guide portion 1490 gradually decreases in width toward the upper side, the bubbles flowing upward gradually approach the hollow fiber body 1440. On this account, a larger amount of bubbles can be absorbed by the hollow fiber body 1440, and therefore, the bubbles can be prevented from being excessively accumulated in the housing 1402. In other words, in Embodiment 5 according to the second disclosure, a space is constituted by the inner wall surface of the housing 1402, the inside surface of the filter structure 1430, and the outer surface of the hollow fiber body 1440 and constitutes the bubble guide portion 1490 or the bubble storing portion 1491.

Embodiment 6 According to Second Disclosure

Figure 12:
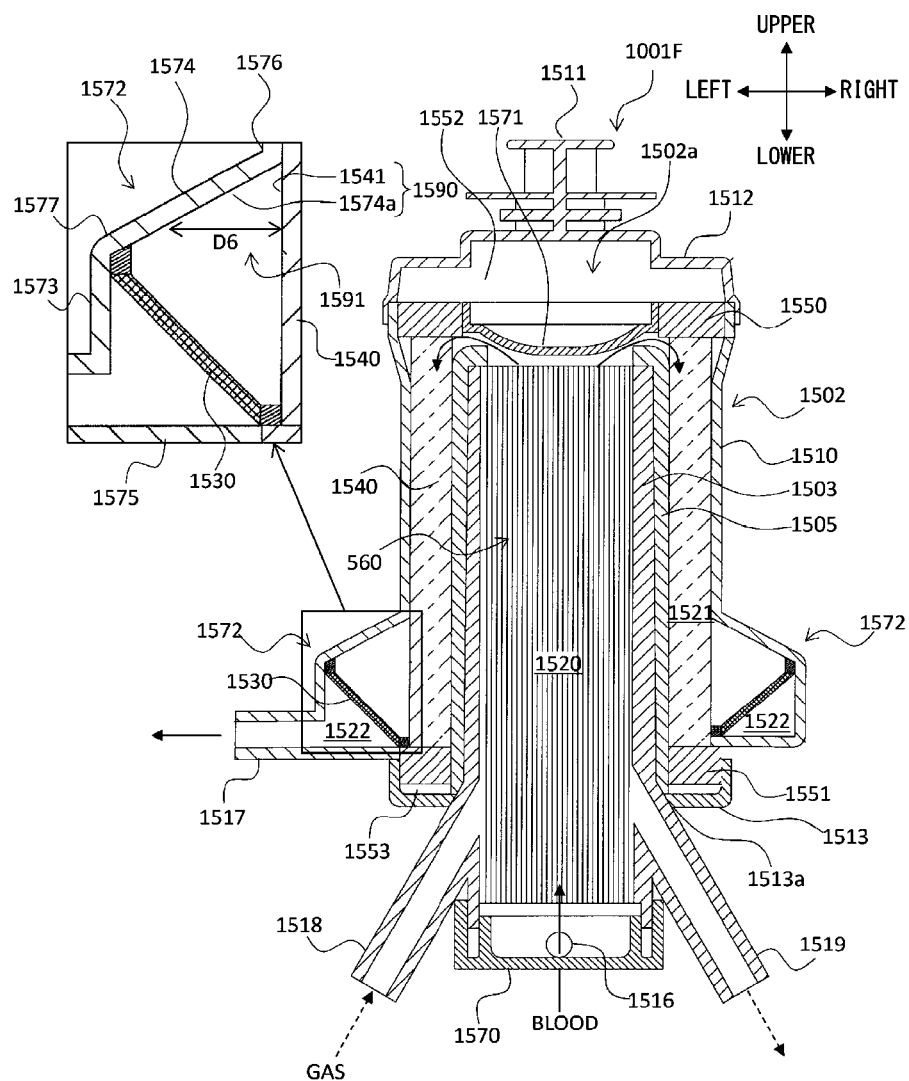
FIG. 12 is a front sectional view showing the artificial lung device according to Embodiment 6 of the second disclosure.

FIG. 12 is a front sectional view showing an artificial lung device 1001F according to Embodiment 6. The artificial lung device 1001F is of a so-called vertical type and includes a housing 1502 and an inner tube 1503. It should be noted that in FIG. 12, reference signs obtained by adding 500 to the reference signs used in the explanation of the artificial lung device 1001A are used for the components of the artificial lung device 1001F which components correspond to the components of the artificial lung device 1001A in terms of at least the functions.

As shown in FIG. 12, according to the artificial lung device 1001F, a heat exchange chamber 1520 and a gas exchange chamber 1521 are formed in the housing 1502. The temperature of the venous blood having flowed into the housing 1502 is adjusted. In addition, carbon dioxide is removed from the blood, and oxygen is added to the blood. Then, the blood as the arterial blood flows to the outside. The housing 1502 includes a cylindrical housing main body 1510, a first header 1512 provided at an upper opening of the housing main body 1510, and a second header 1513 provided at a lower opening of the housing main body 1510.

The cylindrical housing main body 1510 is arranged such that an axis thereof extends in the vertical direction. The upper opening of the housing main body 1510 is closed by the first header 1512. The first header 1512 is formed in a cup shape including an opening directed downward. A suspending tool 1511 is connected to an upper portion of the first header 1512. Moreover, a gas supply port (not shown) is connected to a peripheral portion of the first header 1512, and oxygen-rich gas is introduced into the housing 1502.

The second header 1513 provided at the lower opening of the housing main body 1510 is formed in a cup shape including an opening directed upward. An opening 1513a is formed at a middle position of the second header 1513. Moreover, a gas discharge port (not shown) is connected to a peripheral portion of the second header 1513, and the gas is discharged from the housing 1502 to the outside.

A tubular hollow fiber body 1540 is accommodated in an internal space 1502a of the housing 1502 so as to be externally fitted to a tubular core 1505. To be specific, the hollow fiber body 1540 is constituted by a sheet-shaped hollow fiber membrane formed by a plurality of hollow fibers. The hollow fiber membrane is wound around an outer periphery of the tubular core 1505 and is accommodated in the housing 1502 together with the tubular core 1505. Moreover, instead of directly winding the hollow fiber membrane around the tubular core 1505, a hollow fiber membrane bundle formed in a cylindrical shape in advance may cover the tubular core 1505 and be accommodated in the housing 1502. The tubular core 1505 is located coaxially with the housing main body 1510. A ring-shaped space between the tubular core 1505 and the housing main body 1510 constitutes the gas exchange chamber 1521 and is filled with the hollow fiber body 1540.

A first sealing member 1550 having an annular shape is provided at the upper side of the hollow fiber body 1540, and a second sealing member 1551 having an annular shape is provided at the lower side of the hollow fiber body 1540. A gas inflow space 1552 communicating with the gas supply port is formed at the upper side of the first sealing member 1550 by the first sealing member 1550. A gas outflow space 1553 communicating with the gas discharge port is formed at the lower side of the second sealing member 1551 by the second sealing member 1551. Therefore, the gas supplied from the gas supply port at the upper portion flows from the gas inflow space 1552 through the inner holes of the hollow fibers of the hollow fiber body 1540 toward the lower side, flows through the gas outflow space 1553, and is discharged through the gas discharge port at the lower portion to the outside. It should be noted that the second sealing member 1551 is provided so as to be externally fitted to a lower portion of the tubular core 1505.

A cylindrical heat exchanger casing 1503 is provided so as to be internally fitted in the tubular core 1505 except for a lower portion of the heat exchanger casing 1503. The lower portion of the heat exchanger casing 1503 projects downward from a lower opening of the tubular core 1505 and further projects downward from the opening 1513a of the second header 1513 to be exposed to the outside. A lower end opening of the heat exchanger casing 1503 is closed by a bottom cap 1570. A medium inflow port 1518 and a medium outflow port 1519 are connected to a lower side surface of the heat exchanger casing 1503.

The bottom cap 1570 is formed in a cup shape including an opening directed upward. A blood inflow port 1516 is connected to a peripheral portion of the bottom cap 1570. The medium inflow port 1518 extends in an obliquely downward direction from a predetermined position of the lower side surface of the heat exchanger casing 1503. The medium outflow port 1519 extends in an obliquely downward direction from a predetermined position of the lower side surface of the heat exchanger casing 1503, the predetermined position being different from the position to which the medium inflow port 1518 is connected.

The inside of the heat exchanger casing 1503 constitutes the heat exchange chamber 1520. A tube bundle 1560 is accommodated in the heat exchange chamber 1520 such that an axial direction of the tube bundle 1560 coincides with an axial direction of the heat exchanger casing 1503. The tube bundle 1560 is an assembly of a plurality of heat exchange pipes. The pipes are made of a material, such as stainless steel, having high heat conductivity. An outer periphery of an upper end portion of the tube bundle 1560 is sealed by a sealing member (not shown) such that the heat exchange medium and the blood having flowed out from the tube bundle 1560 are prevented from being mixed with each other.

In the heat exchange chamber 1520, when the blood flows into the blood inflow port 1516 located at the lower side, the blood enters into the pipes of the tube bundle 1560 from lower end openings of the pipes, flows upward, and flows out from the tube bundle 1560 through upper end openings of the pipes. On the other hand, the heat medium which is maintained at a predetermined temperature flows into the medium inflow port 1518, flows through the gaps of the pipes of the tube bundle 1560, and flows out from the medium outflow port 1519.

A diffusing portion 1571 is provided above the heat exchanger casing 1503 so as to be fitted to an opening portion of the first sealing member 1550 having an annular shape. As shown in FIG. 12, a lower surface of the diffusing portion 1571 projects downward in a circular-arc shape in a front view. Therefore, the flow direction of the blood having flowed out from the upper portion of the tube bundle 1560 is changed to a radially outward direction by the diffusing portion 1571, and the blood flows into the gas exchange chamber 1521 from an upper portion of the gas exchange chamber 1521.

An enlarged diameter portion 1572 is formed at a lower portion of the housing main body 1510 so as to be larger in diameter than the other portion of the housing main body 1510 over the entire periphery. The enlarged diameter portion 1572 includes: a peripheral surface portion 1573 constituted by a tubular body; an annular upper surface portion 1574 covering an upper end opening of the peripheral surface portion 1573; and an annular lower surface portion 1575 covering a lower end opening of the peripheral surface portion 1573. The annular upper surface portion 1574 is inclined such that an inner peripheral portion 1576 is located higher than an outer peripheral portion 1577. In other words, the upper surface portion 1574 is formed in a substantially truncated cone shape. Therefore, an inner surface (lower surface) of the upper surface portion 1574 constitutes an inclined surface 1574*a* which approaches a center as it extends upward.

A space is formed between the inner surface of the enlarged diameter portion 1572 and an outer peripheral surface 1541 of the hollow fiber body 1540, and a filter structure 1530 is arranged in the space. The filter structure 1530 is formed in a truncated cone shape including a top portion directed downward. An upper end (large-diameter end) of the filter structure 1530 is located at a connection portion where the peripheral surface portion 1573 and the upper surface portion 1574 in the enlarged diameter portion 1572 are connected to each other. A lower end (small-diameter end) of the filter structure 1530 is located at a contact portion where the lower surface portion 1575 of the enlarged diameter portion 1572 and the hollow fiber body 1540 contact each other. Moreover, a blood outflow port 1517 extending in the radially outward direction is connected to a predetermined position of the peripheral surface portion 1573 of the enlarged diameter portion 1572.

Therefore, the inside of the enlarged diameter portion 1572 is divided by the filter structure 1530 into a space 1591 located adjacent to the hollow fiber body 1540 and a blood outflow space 1522 communicating with the blood outflow port 1517. Then, the blood having flowed through the hollow fiber body 1540 passes through the filter structure 1530 from the space 1591, flows through the blood outflow space 1522, and flows through the blood outflow port 1517 to the outside.

According to the artificial lung device 1001F configured as above, while the blood having flowed into the blood inflow port 1516 flows through the tube bundle 1560 of the heat exchange chamber 1520 to the upper side, the temperature of the blood is adjusted by the medium having flowed into the medium inflow port 1518. The blood having been adjusted in temperature makes a turn at the upper side of the heat exchange chamber 1520 and flows into the gas exchange chamber 1521. While the blood flows through the gaps of the hollow fibers of the hollow fiber body 1540, the blood is subjected to the gas exchange. Then, foreign matters in the blood having flowed out from the hollow fiber body 1540 are removed by the filter structure 1530, and the blood as the arterial blood flows to the outside.

In the artificial lung device 1001F, a bubble guide portion 1590 is constituted by the upper surface portion 1574 of the enlarged diameter portion 1572 and the hollow fiber body 1540. More specifically, as shown in FIG. 12, the inner surface of the upper surface portion 1574 constitutes the inclined surface 1574*a* as described above, and the inclined surface 1574*a* constitutes the opposing wall according to the present invention. To be specific, the inclined surface 1574*a* is located so as to be opposed to the outer peripheral surface 1541 of the hollow fiber body 1540 and forms the space (bubble storing portion) 1591 between the inclined surface 1574*a* and the outer peripheral surface 1541. Moreover, a separation dimension D6 between the inclined surface 1574*a* and the outer peripheral surface 1541 of the hollow fiber body 1540 gradually decreases to become zero toward the vertically upper side.

According to this configuration, even when there are bubbles which flowed through the hollow fiber body 1540 but were not absorbed, such bubbles flows upward in the bubble guide portion 1590 along the inclined surface 1574*a* of the enlarged diameter portion 1572 or the outer peripheral surface 1541 of the hollow fiber body 1540 by buoyancy of the bubbles. Since the space 1591 included in the bubble guide portion 1590 gradually decreases in width toward the upper side, the bubbles flowing upward gradually approach the hollow fiber body 1540. On this account, a larger amount of bubbles can be absorbed by the hollow fiber body 1540, and therefore, the bubbles can be prevented from being excessively accumulated in the housing 1502. In other words, in Embodiment 6 according to the second disclosure, a space is constituted by the inner wall of the housing 1502, the inside surface of the filter structure 1530, and the outer surface of the hollow fiber body 1540 and constitutes the bubble guide portion 1590 or the bubble storing portion 1591.

Embodiment 7 According to Second Disclosure

Figure 13:
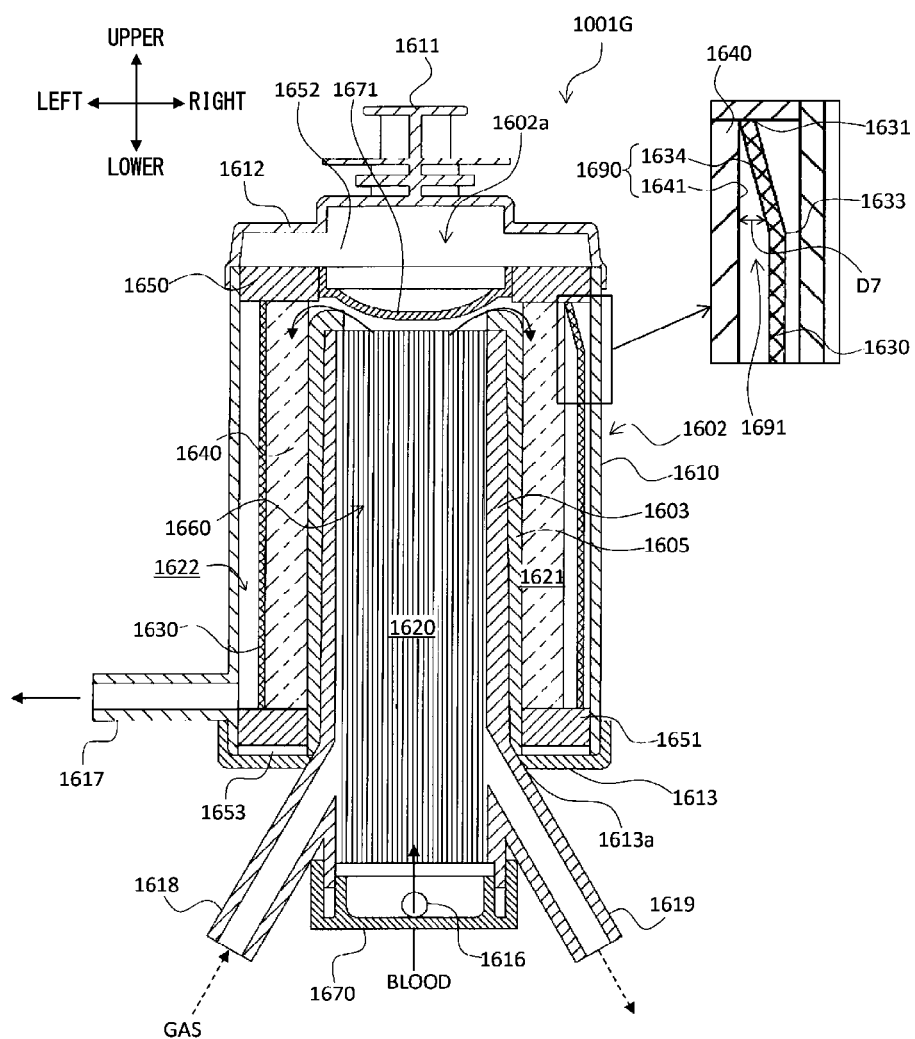
FIG. 13 is a front sectional view showing the artificial lung device according to Embodiment 7 of the second disclosure.

FIG. 13 is a front sectional view showing an artificial lung device 1001G according to Embodiment 7. Hereinafter, portions of the artificial lung device 1001G which portions are different from those of the artificial lung device 1001F will be mainly described. It should be noted that in FIG. 13, reference signs each obtained by replacing "5" that is the third digit (except for the alphabetical letter) in the reference signs used in the explanation of the artificial lung device 1001F with "6" are used for the components of the artificial lung device 1001G which components correspond to the components of the artificial lung device 1001F in terms of at least the functions.

As shown in FIG. 13, in the artificial lung device 1001G, the enlarged diameter portion is not provided at a lower portion of a housing main body 1610. To be specific, the housing main body 1610 is formed in a cylindrical shape having a substantially constant diameter from its upper end to its lower end. A blood outflow port 1617 is connected to a lower end portion of the housing main body 1610. Moreover, an inner peripheral surface of a tubular hollow fiber body 1640 wound around an outer periphery of a tubular core 1605 is in contact with an outer peripheral surface of the tubular core 1605. However, an outer peripheral surface of the hollow fiber body 1640 is located so as to be spaced apart from an inner peripheral surface of the housing main body 1610 by a predetermined distance. Therefore, a cylindrical space is formed between the housing main body 1610 and the hollow fiber body 1640 over the entire periphery, and a cylindrical filter structure 1630 is provided in this space.

The filter structure 1630 has a diameter larger than an outer diameter of the hollow fiber body 1640 and is provided so as to surround an outer periphery of the hollow fiber body 1640. An upper end 1631 of the filter structure 1630 is in contact with a lower surface of a first sealing member 1650, and a lower end 1632 of the filter structure 1630 is in contact with an upper surface of a second sealing member 1651. Moreover, the filter structure 1630 is arranged eccentrically with respect to the hollow fiber body 1640. Therefore, a part of an inner peripheral surface of the filter structure 1630 in a circumferential direction is located so as to be spaced apart from an outer peripheral surface 1641 of the hollow fiber body 1640, and the other part of the inner peripheral surface of the filter structure 1630 in the circumferential direction is in contact with the outer peripheral surface 1641. Then, a space sandwiched between the filter structure 1630 and the housing main body 1610 constitutes a bubble outflow space 1622 communicating with the bubble outflow port 1617.

A bent portion 1633 is provided at a predetermined position of an upper portion of a part of the filter structure 1630, the part being spaced apart from the outer peripheral surface 1641 of the hollow fiber body 1640. An inner surface of a part of the filter structure 1630 which part connects the bent portion 1633 and the upper end 1631 constitutes an inclined surface 1634. In the artificial lung device 1001G, a bubble guide portion 1690 is constituted by the inclined surface 1634 and the outer peripheral surface 1641 of the hollow fiber body 1640. To be specific, the inclined surface 1634 constitutes the opposing wall according to the present invention. The inclined surface 1634 is located so as to be opposed to the outer peripheral surface 1641 of the hollow fiber body 1640 and forms a space (bubble storing portion) 1691 between the inclined surface 1634 and the outer peripheral surface 1641 of the hollow fiber body 1640. Moreover, a separation dimension D7 between the inclined surface 1634 and the outer peripheral surface 1641 of the hollow fiber body 1640 gradually decreases to become zero toward the vertically upper side.

According to this configuration, even when there are bubbles which flowed through the hollow fiber body 1640 but were not absorbed, such bubbles move upward in the bubble guide portion 1690 along the inclined surface 1634 of the filter structure 1630 or the outer peripheral surface 1641 of the hollow fiber body 1640 by buoyancy of the bubbles. Since the space 1691 included in the bubble guide portion 1690 gradually decreases in width toward the upper side, the bubbles flowing upward gradually approach the hollow fiber body 1640. On this account, a larger amount of bubbles can be absorbed by the hollow fiber body 1640, and therefore, the bubbles can be prevented from being excessively accumulated in a housing 1602. In other words, in Embodiment 7 according to the second disclosure, a space is constituted by the inside surface of the filter structure 1630 and the outer surface of the hollow fiber body 1640 and constitutes the bubble guide portion 1690 or the bubble storing portion 1691.

Embodiment 8 According to Second Disclosure

Figure 14:
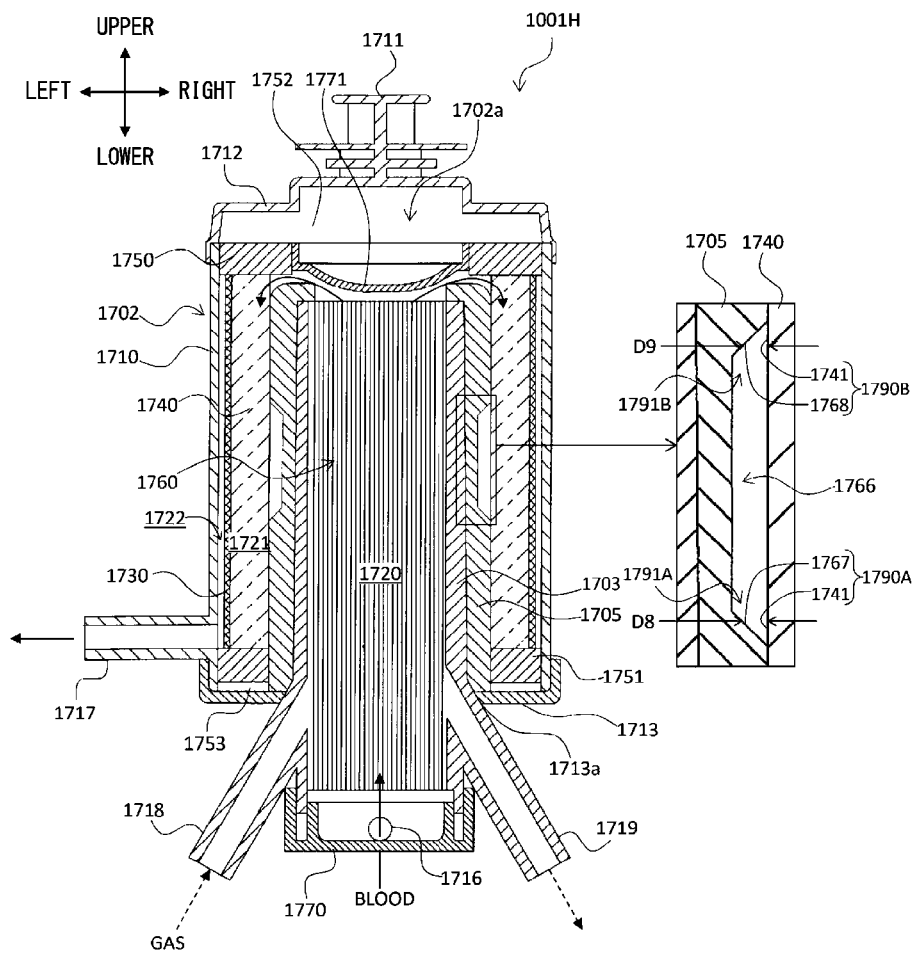
FIG. 14 is a front sectional view showing the artificial lung device according to Embodiment 8 of the second disclosure.

FIG. 14 is a front sectional view showing an artificial lung device 1001H according to Embodiment 8. Hereinafter, portions of the artificial lung device 1001H which portions are different from those of the artificial lung device 1001G will be mainly described. It should be noted that in FIG. 14, reference signs each obtained by replacing "6" that is the third digit (except for the alphabetical letter) in the reference signs used in the explanation of the artificial lung device 1001G with "7" are used for the components of the artificial lung device 1001H which components correspond to the components of the artificial lung device 1001G in terms of at least the functions.

As shown in FIG. 14, in the artificial lung device 1001H, a tubular hollow fiber body 1740 is formed such that a hollow fiber membrane is wound around a tubular core 1705. Moreover, a tubular filter structure 1730 is included so as to be externally fitted to the hollow fiber body 1740. An inner diameter of the filter structure 1730 is substantially equal to an outer diameter of the hollow fiber body 1740. Therefore, an outer peripheral surface of the hollow fiber body 1740 is in contact with an inner peripheral surface of the filter structure 1730 over the substantially entire region.

In the artificial lung device 1001H, a gas guide portion 1790 is constituted by the tubular core 1705 and the hollow fiber body 1740. Specifically, as shown in FIG. 14, a reduced-diameter portion 1766 is formed at an outer surface of a middle portion of the tubular core 1705 which portion is located at a middle position in the upper-lower direction so as to be smaller in diameter than the other portion of the tubular core 1705. The reduced-diameter portion 1766 is provided so as to surround the middle portion of the tubular core 1705. The blood between the reduced-diameter portion 1766 and the hollow fiber body 1740 flows downward as with the blood in the hollow fiber body 1740. Moreover, an upper portion of the reduced-diameter portion 1766 constitutes a tapered surface 1768 which has a tapered sectional contour so as to decrease in diameter toward the lower side, and a lower portion of the reduced-diameter portion 1766 constitutes a tapered surface 1767 which has a tapered sectional contour so as to decrease in diameter toward the upper side. It should be noted that in the present embodiment, the reduced-diameter portion 1766 is provided so as to surround the middle portion of the tubular core 1705. However, the present embodiment is not limited to this. For example, a plurality of reduced-diameter portions may be provided so as to be spaced apart from each other. Moreover, a sectional shape of the reduced-diameter portion 1766 is not limited to the shape shown in FIG. 14 and may be a shape, such as a triangular shape, as long as the reduced-diameter portion 1766 has a section which decreases in diameter toward the upper side or a section which decreases in diameter toward the lower side. Moreover, the reduced-diameter portion 1766 does not have to surround the tubular core 1705 over the entire periphery and may be provided at the tubular core 1705 partially in the circumferential direction.

A bubble guide portion 1790A is constituted by the tapered surface 1767, located at the lower side, of the reduced-diameter portion 1766 and the hollow fiber body 1740. To be specific, the tapered surface 1767 located at the lower side constitutes the opposing wall according to the present invention. The tapered surface 1767 is located so as to be opposed to an inner surface 1741 of the hollow fiber body 1740 and forms a space (bubble storing portion) 1791A between the tapered surface 1767 and the inner surface 1741 of the hollow fiber body 1740. Moreover, a separation dimension D8 between the tapered surface 1767 and the inner surface 1741 of the hollow fiber body 1740 gradually decreases to become zero toward the downstream side (i.e., the lower side) in the flow direction of the blood in the space 1791A. In the artificial lung device 1001H, the bubble guide portion 1790A is formed so as to surround the tubular core 1705.

Moreover, a bubble guide portion 1790B is constituted by the tapered surface 1768, located at the upper side, of the reduced-diameter portion 1766 and the hollow fiber body 1740. To be specific, the tapered surface 1768 located at the upper side constitutes the opposing wall according to the present invention. The tapered surface 1768 is located so as to be opposed to the inner surface 1741 of the hollow fiber body 1740 and forms a space (bubble storing portion) 1791B between the tapered surface 1768 and the inner surface 1741 of the hollow fiber body 1740. Moreover, a separation dimension D9 between the tapered surface 1768 and the inner surface 1741 of the hollow fiber body 1740 gradually decreases to become zero toward the vertically upper side. In the artificial lung device 1001H, the bubble guide portion 1790B is also formed so as to surround the tubular core 1705.

According to this configuration, even when there are bubbles which flowed through the hollow fiber body 1740 but were not absorbed, such bubbles move in the bubble guide portion 1790A to the downstream side along the flow direction of the blood. Since the space 1791A included in the bubble guide portion 1790A gradually decreases in width toward the downstream side, the bubbles moving to the downstream side gradually approach the hollow fiber body 1740. On this account, a larger amount of bubbles can be absorbed by the hollow fiber body 1740, and therefore, the bubbles can be prevented from being excessively accumulated in a housing 1702.

Moreover, the bubbles which flowed through the hollow fiber body 1740 but were not absorbed move in the bubble guide portion 1790B toward the vertically upper side by buoyancy of the bubbles. Since the space 1791B included in the bubble guide portion 1790B gradually decreases in width toward the upper side, the bubbles flowing upward are gradually pressed against the hollow fiber body 1740. On this account, a larger amount of bubbles can be absorbed by the hollow fiber body 1740, and therefore, the bubbles can be prevented from being excessively accumulated in the housing 1702. In other words, in Embodiment 8 according to the second disclosure, a space is constituted by the inner wall of the housing 1702 and the inner surface of the hollow fiber body 1740 and constitutes the bubble guide portions 1790A and 1790B or the bubble storing portion 1791A and 1791B.

In each of the embodiments according to the second disclosure described as above, the separation dimension between the surface of the gas exchanger and the opposing wall gradually decreases to become zero toward the vertically upper side or toward the downstream side in the flow direction. However, the separation dimension between the surface of the gas exchanger and the opposing wall does not have to become zero. To be specific, a gap may exist between the surface of the gas exchanger and the opposing wall.

As Modified Example of Embodiment 1, when the gap is provided between the surface of the gas exchanger and the opposing wall, the gap may constitute the bubble storing portion. To be specific, even when the blood flows through the gas exchanger, the bubbles in the blood are not completely absorbed in the hollow fiber membrane, and the bubbles may remain. In this case, when the gap (bubble storing portion) is provided at the upper portion of the housing, the bubbles which were not absorbed in the hollow fiber membrane are stored in the gap. When the amount of bubbles stored reaches a certain amount, the bubbles are absorbed in the hollow fiber membrane since the gap faces the gas exchanger. As a result, the bubbles can be prevented from flowing into the body of the patient. In other words, in each of Modified Examples 1 and 2 and Reference Example 1 described below, a space is constituted by an inside surface of a filter structure 1030A, 1030B, or 1030C and an outer surface of a hollow fiber body 1021 and constitutes the bubble guide portion or the bubble storing portion.

Modified Example 1 According to Second Disclosure

Figure 15:
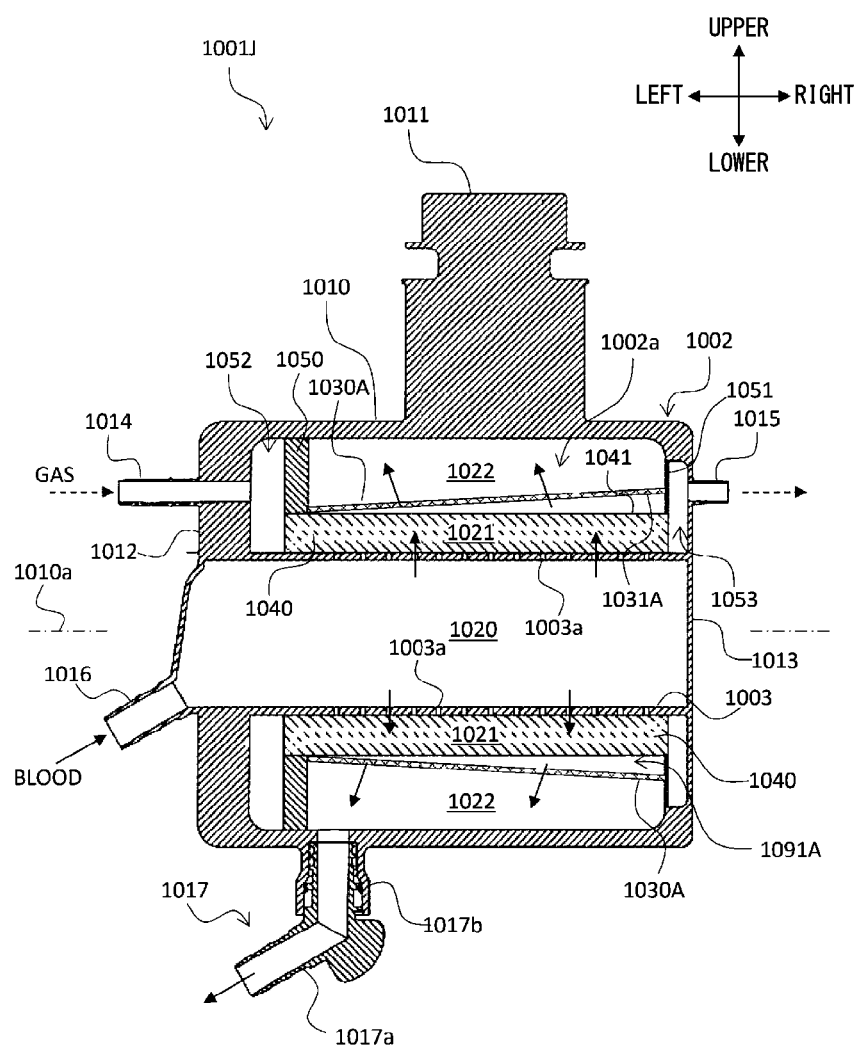
FIG. 15 is a front view showing the artificial lung device according to Modified Example 1 of the second disclosure.

FIG. 15 is a front sectional view showing an artificial lung device 1001J according to Modified Example 1 of Embodiment 1. The artificial lung device 1001) according to Modified Example 1 is the same in configuration as the artificial lung device 1001A according to Embodiment 1 except for the configuration of the filter 1030. Therefore, in FIG. 15, reference signs that are the same as those used in the explanation of the artificial lung device 1001A are used for the components of the artificial lung device 1001J which components are the same as those of the artificial lung device 1001A.

As shown in FIG. 15, the artificial lung device 1001J includes a filter 1030A configured to remove foreign matters in the blood. The filter 1030A is provided so as to cross a passage through which the blood having flowed through the hollow fiber body 1040 flows toward the blood outflow port 1017. More specifically, the filter 1030A is formed in a truncated cone shape including a small-diameter opening end and a large-diameter opening end. A center axis of the filter 1030A extends along the axis 1010a of the housing main body 1010. The filter 1030A is directed such that the small-diameter opening end is located closer to the blood outflow port 1017 than the large-diameter opening end. The filter 1030A is provided so as to surround the outer peripheral surface 1041 of the hollow fiber body 1040.

As a result, a space 1091A is formed between the outer peripheral surface 1041 of the hollow fiber body 1040 and an inner peripheral surface 1031A of the filter 1030A, the inner peripheral surface 1031A constituting the opposing wall opposed to the outer peripheral surface 1041. The blood passes through the filter 1030A while flowing in the space 1091A from the large-diameter opening end of the filter 1030A to the small-diameter opening end of the filter 1030A. Then, a separation dimension between the outer peripheral surface 1041 of the hollow fiber body 1040 and the inner peripheral surface 1031A of the filter 1030A gradually decreases to approach zero toward the downstream side in the flow direction of the blood in the space 1091A. It should be noted that in the example of FIG. 15, a peripheral edge portion of the small-diameter opening end of the filter 1030A is in contact with the outer peripheral surface 1041 of the hollow fiber body 1040 but may be spaced apart from the outer peripheral surface 1041.

Modified Example 2 According to Second Disclosure

Figure 16:
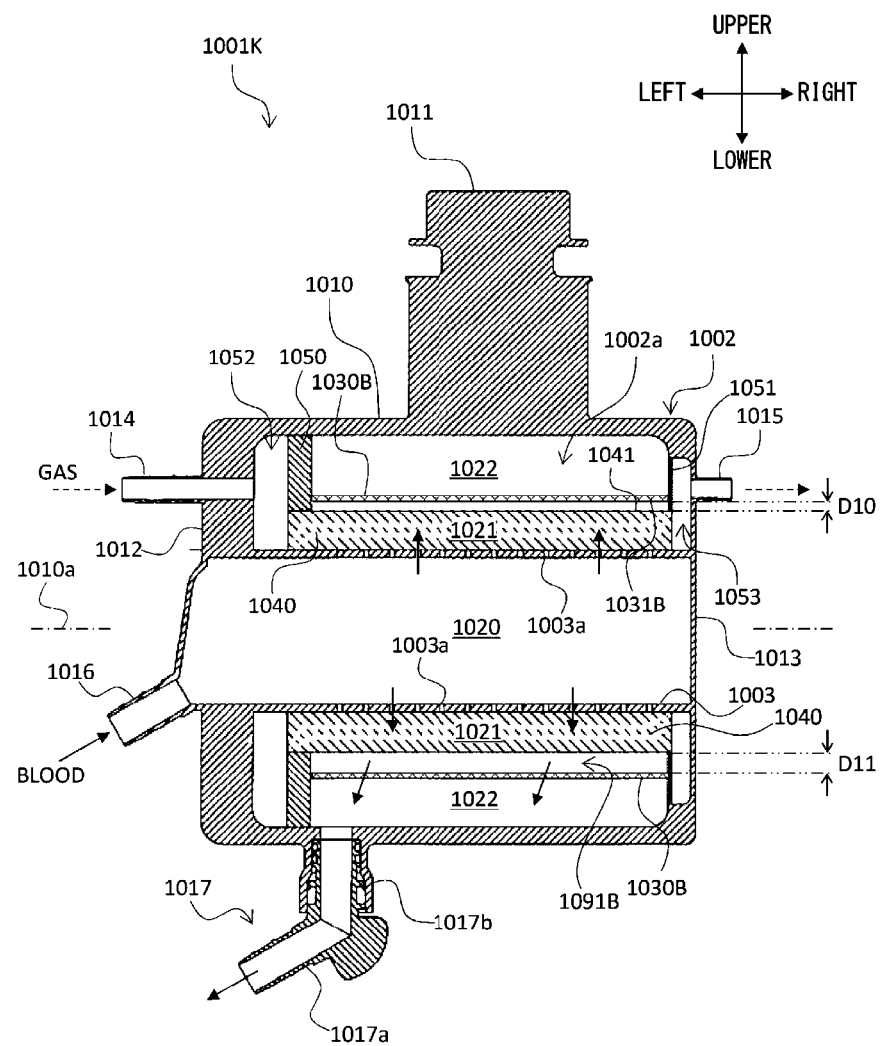
FIG. 16 is a front view showing the artificial lung device according to Modified Example 2 of the second disclosure.

FIG. 16 is a front sectional view showing an artificial lung device 1001K according to Modified Example 2 of Embodiment 1. The artificial lung device 1001K according to Modified Example 2 is the same in configuration as the artificial lung device 1001A according to Embodiment 1 except for the configuration of the filter 1030. Therefore, in FIG. 16, reference signs that are the same as those used in the explanation of the artificial lung device 1001A are used for the components of the artificial lung device 1001K which components are the same as those of the artificial lung device 1001A.

As shown in FIG. 16, the artificial lung device 1001K includes a filter 1030B configured to remove foreign matters in the blood. The filter 1030B is provided so as to cross a passage through which the blood having flowed through the hollow fiber body 1040 flows toward the blood outflow port 1017. Moreover, the filter 1030B is provided as if the filter 1030 of the artificial lung device 1001A of Embodiment 1 is slightly moved upward.

More specifically, the filter 1030B is formed in a cylindrical shape, and an inner diameter of the filter 1030B is larger than an outer diameter of the hollow fiber body 1040. The filter 1030B is arranged eccentrically with respect to the hollow fiber body 1040, similarly formed in a cylindrical shape, in the lower direction, in other words, a center axis of the filter 1030B is located lower than a center axis of the hollow fiber body 1040. Moreover, an inner peripheral surface 1031B of the filter 1030B is arranged so as to be spaced apart from the outer peripheral surface 1041 of the hollow fiber body 1040.

As a result, a space 1091B is formed between the outer peripheral surface 1041 of the hollow fiber body 1040 and the inner peripheral surface 1031B of the filter 1030B, the inner peripheral surface 1031B constituting the opposing wall opposed to the outer peripheral surface 1041. When viewed from the direction along the axis 1010$a$, the space 1091B gradually decreases, i.e., narrows in a direction from a lower portion to an upper portion along the outer peripheral surface 1041 of the hollow fiber body 1040.

The dimension of a gap of the upper portion of the space 1091B is referred to as D10, i.e., a separation dimension between a portion of the inner peripheral surface 1031B of the filter 1030B which portion corresponds to the upper portion of the filter 1030B and the outer peripheral surface 1041 of the hollow fiber body 1040 opposed to the above portion of the inner peripheral surface 1031B is referred to as D10. Moreover, the dimension of a gap of the lower portion of the space 1091B is referred to as D11, i.e., a separation dimension between a portion of the inner peripheral surface 1031B of the filter 1030B which portion corresponds to the lower portion of the filter 1030B and the outer peripheral surface 1041 of the hollow fiber body 1040 opposed to the above portion of the inner peripheral surface 1031B is referred to as D11. In this case, the separation dimension D10 is smaller than the separation dimension D11. For example, the separation dimension D10 is selectable within a range of more than 0 millimeter and 5 millimeters or less, preferably within a range of more than 0 millimeter and 3 millimeters or less, more preferably within a range of 2 millimeters or more and 3 millimeters or less.

As above, since the space 1091B gradually decreases to approach zero toward the vertically upper side, the bubbles in the space 1091B can be absorbed by the hollow fiber body 1040 again. It should be noted that according to the configuration of Modified Example 2, the filter 1030B and the hollow fiber body 1040 are spaced apart from each other over the entire periphery as described above, and the space 1091B does not finally become zero toward the vertically upper side. Even in this configuration, as long as the separation dimension D10 of the upper portion of the space 1091B is set within the above range, the bubbles can be brought into contact with the hollow fiber body 1040 and absorbed by the hollow fiber body 1040 again without any trouble. It should be noted that the separation dimension D10 can be set in accordance with the sizes of the generated bubbles and is not limited to the above ranges.

Reference Example 1 According to Second Disclosure

Figure 17:
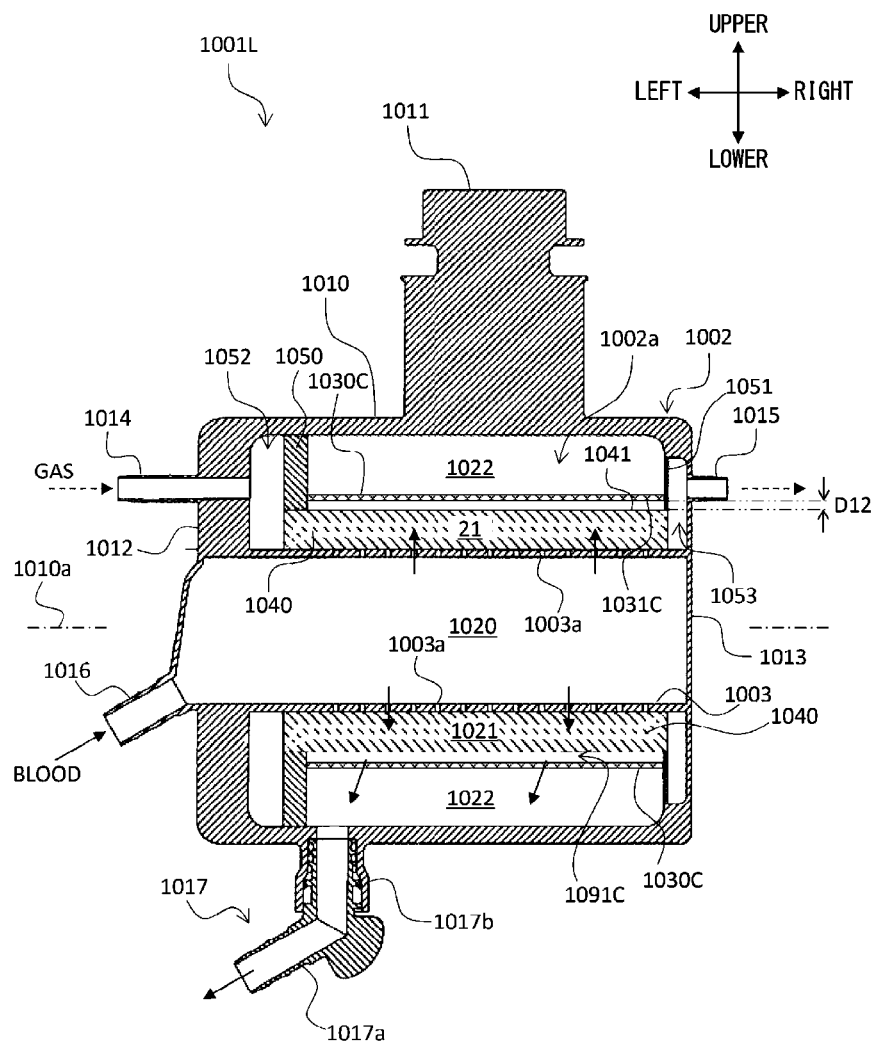
FIG. 17 is a front view showing the artificial lung device according to Reference Example 1 of the second disclosure.

FIG. 17 is a front sectional view showing an artificial lung device 1001L according to Reference Example 1. The artificial lung device 1001L according to Reference Example 1 is the same in configuration as the artificial lung device 1001A according to Embodiment 1 except for the configuration of the filter 1030. Therefore, in FIG. 17, reference signs that are the same as those used in the explanation of the artificial lung device 1001A are used for the components of the artificial lung device 1001L which components are the same as those of the artificial lung device 1001A.

As shown in FIG. 17, the artificial lung device 1001L includes a filter 1030C configured to remove foreign matters in the blood. The filter 1030C is provided so as to cross a passage through which the blood having flowed through the hollow fiber body 1040 flows toward the blood outflow port 1017. More specifically, the filter 1030C is formed in a cylindrical shape, and an inner diameter of the filter 1030C is larger than an outer diameter of the hollow fiber body 1040. The filter 1030C is provided so as to concentrically surround the outside of the hollow fiber body 1040 similarly formed in a cylindrical shape.

As a result, a space 1091C is formed between the outer peripheral surface 1041 of the hollow fiber body 1040 and an inner peripheral surface 1031C of the filter 1030C, the inner peripheral surface 1031C constituting the opposing wall opposed to the outer peripheral surface 1041. When viewed from the direction along the axis 1010$a$, the space 1091C forms a gap having a dimension D12 that is constant over the entire periphery along the outer peripheral surface 1041 of the hollow fiber body 1040. For example, the dimension D12 is selectable within a range of more than 0 millimeter and 5 millimeters or less, preferably within a range of more than 0 millimeter and 3 millimeters or less, more preferably within a range of 2 millimeters or more and 3 millimeters or less.

As above, the artificial lung device 1001L according to Reference Example 1 is configured such that the space 1091C does not gradually decrease. However, as long as the separation dimension D12 between the inner peripheral surface 1031C of the filter 1030C and the outer peripheral surface 1041 of the hollow fiber body 1040 is set within the above ranges, the bubbles in the space 1091C can be brought into contact with the hollow fiber body 1040 and absorbed by the hollow fiber body 1040 again. It should be noted that the dimension D12 of the gap formed by the space 1091C does not have to be completely constant over the entire periphery and may differ at respective portions thereof as long as the dimension D12 falls within the above numerical range. It should be noted that the dimension D12 can be set in accordance with the sizes of the generated bubbles and is not limited to the above ranges.

It should be noted that in all of the embodiments and the modified examples according to the second disclosure, the configuration of achieving the action of being able to make the bubbles approach the surface of the hollow fiber body (gas exchanger) corresponds to the expression "gradually decrease to approach zero." Moreover, only the bubble guide portion configured to achieve the function of "gradually decreasing to approach zero" may be constituted by not a filter material but a (liquid-tight and airtight) plate member through which the blood and the bubbles do not pass. With this, even if high back pressure acts on the blood, the bubbles can be prevented from passing through the filter.

An embodiment according to the third disclosure will be described.

Figure 18:
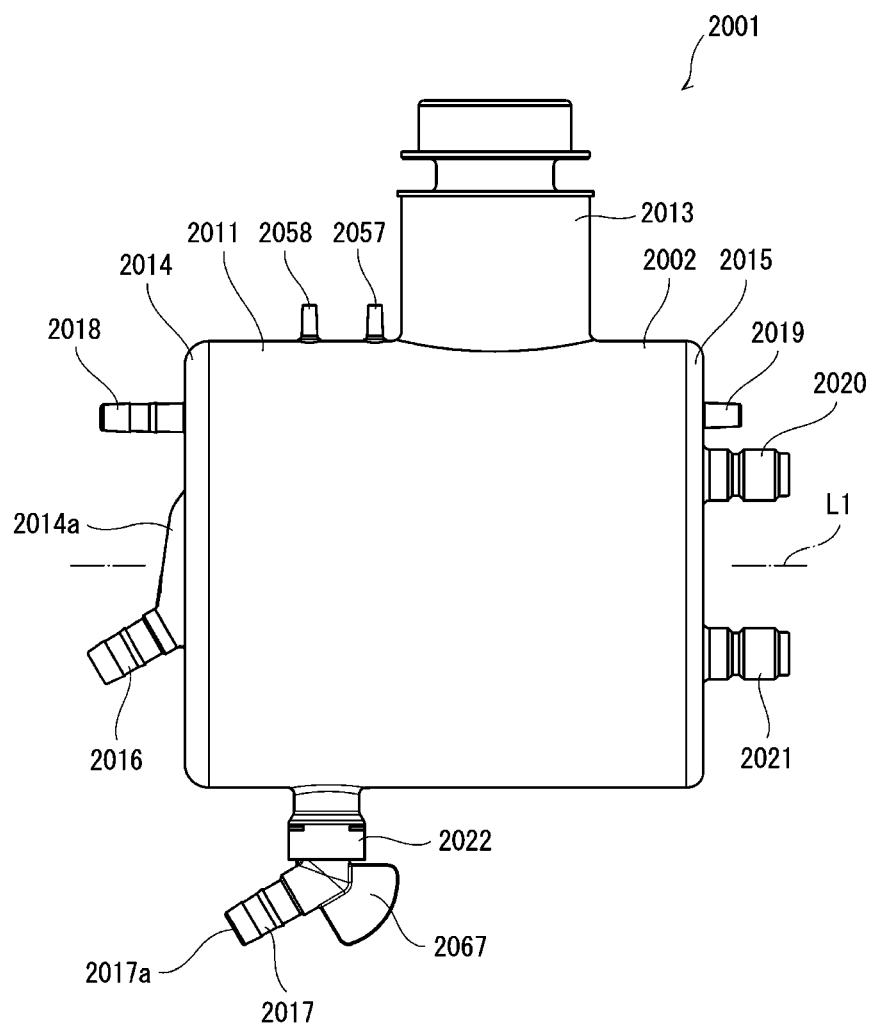
FIG. 18 is a front view showing appearance of the artificial lung device of the present embodiment of the third disclosure.
Figure 19:
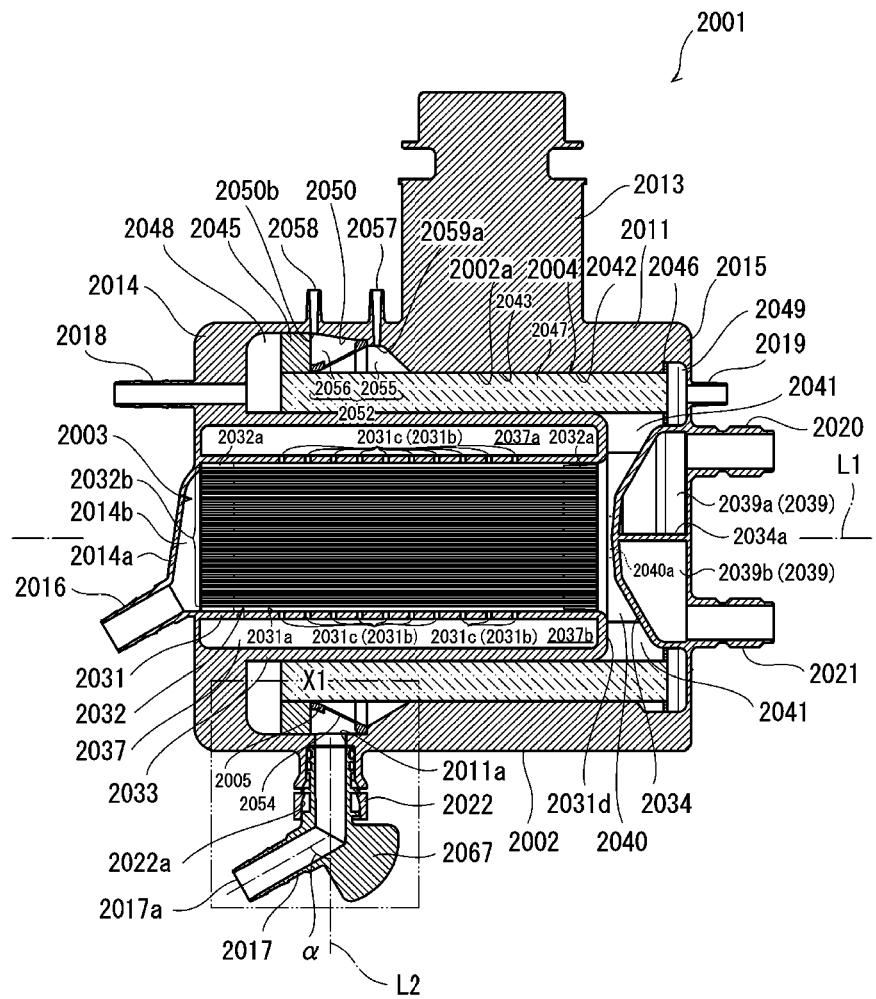
FIG. 19 is a sectional view showing the artificial lung device of FIG. 18 in the third disclosure.

In a surgical operation, such as a heart surgical operation, which is performed after the movement of the heart of a patient is stopped, an artificial lung device 2001 shown in FIG. 18 is used as a substitute for the function of the lung of the patient. The artificial lung device 2001 removes carbon dioxide contained in the blood of the patient and adds oxygen to the blood, i.e., has the gas exchange function. Moreover, the artificial lung device 2001 has the heat exchange function to adjust the temperature of the blood in addition to the gas exchange. The artificial lung device 2001 having such functions is a so-called horizontal type artificial lung device. As shown in FIG. 19, the artificial lung device 2001 includes a housing 2002, a heat exchanger 2003, a gas exchanger 2004, and a filter member 2005.

The housing 2002 is formed in a substantially hollow cylindrical shape and includes an internal space 2002a accommodating two exchangers 2003 and 2004. More specifically, the housing 2002 mainly includes a housing main body 2011, a suspending portion 2013, and two cap portions 2014 and 2015. The housing main body 2011 is formed in a substantially cylindrical shape and accommodates the above-described two exchangers 2003 and 2004. Moreover, the suspending portion 2013 is provided at an outer peripheral surface of the housing main body 2011. The suspending portion 2013 is arranged at an axially middle portion of the housing main body 2011 and extends in the radially outward direction from the outer peripheral surface of the housing main body 2011. Moreover, the suspending portion 2013 is formed in, for example, a substantially columnar shape and is suspended in such a manner that a tip end-side portion thereof is attached to a suspending device (not shown). To be specific, the housing main body 2011 can be suspended through the suspending portion 2013, and an axis L1 of the suspended housing main body 2011 extends in the horizontal direction. The suspending portion 2013 is arranged at the upper portion of the outer peripheral surface of the housing main body 2011 arranged as above, and opening end portions, located at both axial sides, of the housing main body 201 are closed by the two cap portions 2014 and 2015.

Each of the two cap portions 2014 and 2015 is formed in a substantially circular plate shape. The first cap portion 2014 closes one of the opening end portions of the housing main body 2011, and the second cap portion 2015 closes the other opening end portion of the housing main body 2011. To be specific, the first cap portion 2014 constitutes a first end portion of the housing 2002, and the second cap portion 2015 constitutes a second end portion of the housing 2002. Moreover, a blood inflow port 2016 is formed at the first cap portion 2014 in the vicinity of a central axis of the first cap portion 2014 (i.e., in the vicinity of the axis L1). The blood inflow port 2016 is formed in a substantially cylindrical shape and projects in an obliquely downward direction from a position at the lower side of the central axis of the first cap portion 2014. A venous blood tube (not shown) is connected to the blood inflow port 2016 having such shape. The venous blood is introduced through the venous blood tube and the blood inflow port 2016 into the housing main body 2011. Moreover, a blood outflow port 2017 is formed at a lower portion of the outer peripheral surface of the housing main body 2011 (i.e., at an opposite side of the suspending portion 2013). The blood outflow port 2017 is formed in a substantially cylindrical shape. The blood outflow port 2017 projects downward and is bent in an obliquely downward direction at a tip side. An arterial blood tube (not shown) is connected to the blood outflow port 2017 having such shape, and the arterial blood generated by the artificial lung device 2001 is discharged to the arterial blood tube.

Moreover, as shown in FIG. 18, a gas inlet port 2018 is formed at the first cap portion 2014. The gas inlet port 2018 is formed in a substantially cylindrical shape and projects in the axial direction from the vicinity of an outer peripheral edge of the first cap portion 2014. The gas inlet port 2018 having such shape is open to the atmosphere and takes oxygen-containing gas (i.e., air) from the atmosphere into the housing 2002. Moreover, as shown in FIG. 18, a gas discharge port 2019 is formed at the second cap portion 2015. The gas discharge port 2019 is formed in a substantially cylindrical shape and projects in the axial direction from the vicinity of an outer peripheral edge of the second cap portion 2015. The gas discharge port 2019 having such shape discharges the gas, taken into the housing 2 through the gas inlet port 2018, to the atmosphere. It should be noted that a gas concentration measuring device may be connected to the gas discharge port 2019 through a tube or the like and measure a carbon dioxide concentration of the discharged gas.

Moreover, two ports 2020 and 2021 are formed at the second cap portion 2015. The two ports 2020 and 2021 are provided at the second cap portion 2015 in the vicinity of a central axis (i.e., the axis L1) of the second cap portion 2015 so as to sandwich the central axis and be spaced apart from each other in the vertical direction. It should be noted that the two ports 2020 and 2021 do not necessarily have to be spaced apart from each other in the vertical direction and may be spaced apart from each other in the left-right direction (a near side and a deep side on the paper surface) or may be spaced apart from each other in an oblique direction. Each of the two ports 2020 and 2021 is formed in a substantially cylindrical shape and projects in the axial direction from the second cap portion 2015 but may project in a direction intersecting with the axis. The medium inflow port 2021 that is one of the two ports 2020 and 2021 is connected to a medium supply tube (not shown) and can introduce a medium, such as hot water or cold water, into the housing 2002. Moreover, the medium outflow port 2020 that is the other port is connected to a medium discharge tube, and the medium in the housing 2002 is discharged through the medium discharge tube to the outside of the housing 2. As shown in FIG. 19, the heat exchanger 2003 is provided in the housing 2002 at which the plurality of ports 2016 to 2021 are formed as above, to adjust the temperature of the venous blood introduced to the housing 2002.

The heat exchanger 2003 is formed in a substantially cylindrical shape and includes a tubular core 2031, a tube bundle 2032, a casing portion 2033, and a medium inflow-outflow portion 2034. The tubular core 2031 is formed in a substantially cylindrical shape and projects along the axis L1 from an inside surface of the first cap portion 2014 toward the second cap portion 2015. Moreover, the tube bundle 2032 is inserted into and arranged in the tubular core 2031. The tube bundle 2032 is formed in a substantially columnar shape and includes a pair of tube supporting bodies 2032a and a plurality of heat exchanger tubes 2032b. Each of the pair of tube supporting bodies 2032a is formed in a substantially circular plate shape and has an outer diameter which substantially coincides with an inner diameter of the tubular core 2031. The pair of tube supporting bodies 2032a formed as above are respectively inserted into both opening end portions of the tubular core 2031 so as to achieve a sealed state. Moreover, a plurality of through holes are provided at each of the pair of tube supporting bodies 2032a so as to penetrate the tube supporting body 2032a in a direction along the axis L1 and be arranged radially about the axis L1. The through holes formed at one of the tube supporting bodies 2032a and the through holes formed at the other tube supporting body 2032a correspond to each other, and each of the heat exchanger tubes 2032b is inserted into the corresponding through holes.

The heat exchanger tubes 2032b are long and thin cylindrical tubes made of a material, such as stainless steel, having high heat conductivity, and the blood can flow inside the heat exchanger tubes 2032b. Moreover, both end portions of each heat exchanger tube 2032b are inserted into the corresponding through holes of the pair of tube supporting bodies 2032a. With this, the heat exchanger tubes 2032b extend between the pair of tube supporting bodies 2032a. Moreover, the corresponding two through holes are opposed to each other in the axial direction, and the heat exchanger tube 2032b inserted into the corresponding two through holes is arranged so as to extend in the axial direction. With this, in the tube bundle 2032, the plurality of heat exchanger tubes 2032b extend in the axial direction and are arranged, for example, radially. The tube bundle 2032 is formed in a substantially columnar shape. The tube bundle 2032 having such shape is accommodated in the tubular core 2031 in a state where both opening end portions of the tubular core 2031 are sealed by the pair of tube supporting bodies 2032a.

Moreover, the tubular core 2031 is provided at an inside surface of the first cap portion 2014 and around the central axis of the first cap portion 2014 such that an axis of the tubular core 2031 and the axis of the first cap portion 2014 substantially coincide with each other. Furthermore, a portion of the first cap portion 2014 which portion is located around a center of the first cap portion 2014 constitutes a swelling portion 2014a which swells outward in the axial direction relative to the other portion of the first cap portion 2014. The swelling portion 2014a is formed so as to correspond to the opening end portion of the tubular core 2031, and the blood inflow port 2016 is formed at the swelling portion 2014a. A blood inflow space 2014b is formed in the swelling portion 2014a formed as above, and the blood introduced to the blood inflow port 2016 flows into the blood inflow space 2014b. Moreover, a first end of the tube bundle 2032 accommodated in the tubular core 2031 faces the blood inflow space 2014b, and the blood in the blood inflow space 2014b is introduced to a second end side of the tube bundle 2032 through the plurality of heat exchanger tubes 2032b. The blood inflow space 2014b is isolated from the inside of the tubular core 2031 by one of the tube supporting bodies 2032a, and therefore, the blood in the blood inflow space 2014b is not introduced to a space which is located inside the tubular core 2031 and around the tube bundle 2032. Then, instead of the blood, the medium is introduced to the inside of the tubular core 2031, and the temperature of the blood flowing through the plurality of heat exchanger tubes 2032b can be adjusted by the medium. Moreover, the casing portion 2033 is provided at the first cap portion 2014 to introduce the medium to the inside of the tubular core 2031.

The casing portion 2033 is formed in a substantially cylindrical shape, and an inner diameter of the casing portion 2033 is larger than an outer diameter of the tubular core 2031. The casing portion 2033 having such shape is provided at the inner surface of the first cap portion 2014 such that an axis of the casing portion 2033 coincides with the axis L1 of the housing main body 11. Moreover, the casing portion 2033 extends along the axis L1 from the inside surface of the first cap portion 2014 toward the second cap portion 2015. The casing portion 2033 having such shape is substantially the same in length in the axial direction as the tubular core 2031. Moreover, a flange 2031d projecting in the radially outward direction is formed at an opening end portion of the tubular core 2031 which portion is located close to the second cap portion 2015. The flange 2031d is formed at the tubular core 2031 over the entire periphery in the circumferential direction, and an outer peripheral edge of the flange 2031d extends to reach an opening end portion of the casing portion 2033. Moreover, the casing portion 2033 is larger in diameter than the tubular core 2031 as described above, and the casing portion 2033 and the tubular core 2031 are arranged so as to be spaced apart from each other in the radial direction. With this, an inside ring-shaped space 2037 that is closed and has a substantially annular shape is formed between the casing portion 2033 and the tubular core 2031. A pair of dividing walls (not shown) are arranged in the inside ring-shaped space 2037 formed as above.

The pair of dividing walls are arranged in the inside ring-shaped space 2037 so as to be located at even intervals, i.e., separated from each other by 180 degrees in the circumferential direction. The pair of dividing walls are provided in the inside ring-shaped space 2037 so as to extend from the outer peripheral surface of the tubular core 2031 to the inner peripheral surface of the casing portion 2033. The pair of dividing walls divide the inside ring-shaped space 2037 into two passages 2037a and 2037b. To be specific, the two passages 2037a and 2037b (i.e., a medium inflow passage 2037a and a medium outflow passage 2037b) isolated from each other by the pair of dividing walls are formed between the tubular core 2031 and the casing portion 2033. Moreover, a pair of communication portions 2031b are formed at the outer peripheral surface of the tubular core 2031 so as to make the two passages 2037a and 2037b and an internal space 2031a of the tubular core 2031 communicate with each other.

The pair of communication portions 2031b are formed at the outer peripheral surface of the tubular core 2031 so as to respectively correspond to the medium inflow passage 2037*a* and the medium outflow passage 2037*b*. It should be noted that in the present embodiment, as with the pair of dividing walls, the pair of communication portions 2031*b* are arranged at the outer peripheral surface of the tubular core 2031 so as to be located at even intervals in the circumferential direction, i.e., separated from each other by 180 degrees in the circumferential direction. The pair of communication portions 2031*b* respectively face the medium inflow passage 2037*a* and the medium outflow passage 2037*b*. Each of the communication portions 2031*b* arranged as above includes a plurality of communication holes 2031*c*. The plurality of communication holes 2031*c* are formed so as to penetrate the tubular core 2031 in the radial direction. The medium inflow passage 2037*a* and the medium outflow passage 2037*b* communicate with the internal space 2031*a* of the tubular core 2031 through the plurality of communication holes 2031*c*. To be specific, the medium inflow passage 2037*a* and the medium outflow passage 2037*b* are connected to each other through the pair of communication portions 2031*b* and the internal space 2031*a*. Moreover, the medium inflow-outflow portion 2034 through which the medium is supplied to the medium inflow passage 2037*a* and flows out from the medium outflow passage 2037*b* is provided at the second cap portion 2015.

The medium inflow-outflow portion 2034 is provided at the second cap portion 2015 so as to project from the inner surface of the second cap portion 2015 toward the tubular core 2031. More specifically, the medium inflow-outflow portion 2034 is arranged around the central axis of the second cap portion 2015 and is formed in a substantially dome shape. To be specific, a dome internal space 2039 is formed in the medium inflow-outflow portion 2034 and communicates with the medium inflow port 2020 and the medium outflow port 2021 which are formed at the second cap portion 2015. Moreover, a dividing wall plate 2034*a* is arranged in the dome internal space 2039 of the medium inflow-outflow portion 2034. The dividing wall plate 2034*a* is formed in a substantially plate shape and arranged in the dome internal space 2039 to divide the dome internal space 2039 into two spaces that are a medium inflow space 2039*a* and a medium outflow space 2039*b*. Moreover, the dividing wall plate 2034*a* is arranged in the dome internal space 2039 and defines the medium inflow space 2039*a* and the medium outflow space 2039*b* such that the medium inflow space 2039*a* is connected to the medium inflow port 2020, and the medium outflow space 2039*b* is connected to the medium outflow port 2021. Moreover, a pair of extending portions 2040 are provided at the medium inflow-outflow portion 2034 so as to extend between the medium inflow-outflow portion 2034 and the flange 2031*d*. The pair of extending portions 2040 are arranged at positions away from each other by 180 degrees, for example. An inflow passage 2040*a* and an outflow passage (not shown) are respectively formed at the pair of extending portions 2040. The inflow passage 2040*a* connects the medium inflow space 2039*a* and the medium inflow passage 2037*a*, and the outflow passage connects the medium outflow passage 2037*b* and the medium outflow space 2039*b*.

In the heat exchanger 2003 configured as above, the medium is supplied to the medium inflow port 2020 through the medium supply tube. The supplied medium is introduced through the medium inflow space 2039*a* and the inflow passage 2040*a* to the medium inflow passage 2037*a* and is further introduced through one of the communication portions 2031*b* to the internal space 2031*a* of the tubular core 2031. As described above, the plurality of heat exchanger tubes 2032*b* are arranged in the internal space 2031*a*, and the medium flows through the gaps of the plurality of heat exchanger tubes 2032*b* to the other communication portion 2031*b*. At this time, the medium performs the heat exchange with the blood flowing inside the heat exchanger tubes 2032*b* (specifically, hot water as the medium applies heat to the blood, and cold water as the medium removes heat from the blood). With this, the temperature of the blood flowing through the heat exchanger tubes 2032*b* is adjusted to a predetermined temperature. The medium having been subjected to the heat exchange flows out from the internal space 2031*a* through the communication portion 2031*b* to the medium outflow passage 2037*b* and is further introduced through the outflow passage and the medium outflow space 2039*b* to the medium outflow port 2021. After that, the medium is discharged through the medium discharge tube to the outside of the housing 2002, specifically, is returned to a medium supply device, is adjusted in temperature again, and is returned to the medium inflow port 2020 through the medium supply tube. As above, according to the heat exchanger 2003, the medium circulates between the internal space 2031*a* and the medium supply device, and the blood flowing in the heat exchanger tubes 2032*b*, i.e., in the tube bundle 2032 is subjected to the heat exchange with the medium. Thus, the temperature of the blood is adjusted. The blood flows through the tube bundle 2032 while being adjusted in temperature, and is introduced to the other end portion of the tube bundle 2032.

The other end portion of the tube bundle 2032 is arranged away from the medium inflow-outflow portion 2034 in the axial direction, and the pair of extending portions 2040 are arranged away from each other in the circumferential direction. With this, a pair of radial passages 2041 extending from a center in the radially outward direction (upper-lower direction in the present embodiment) are formed between the tube bundle 2032 and the medium inflow-outflow portion 2034. The blood flows out from the other end portion of the tube bundle 2032 through the pair of radial passages 2041 to the outside of the casing portion 2033 in the radial direction. An outer diameter of the casing portion 2033 is smaller than an inner diameter of the housing main body 2011, and an outside ring-shaped space 2042 having a substantially annular shape is formed between the casing portion 2033 and the housing main body 2011. A ring-shaped passage 2043 is formed as part of the outside ring-shaped space 2042. The blood having flowed out from the radial passages 2041 is introduced to the ring-shaped passage 2043. Moreover, the gas exchanger 2004 is accommodated in the outside ring-shaped space 2042.

The gas exchanger 2004 has a function of removing carbon dioxide contained in the blood and adding oxygen to the blood. More specifically, the gas exchanger 2004 is formed in a substantially cylindrical shape and is constituted by two sealing members 2045 and 2046 and a hollow fiber body 2047. Each of the two sealing members 2045 and 2046 is formed in a substantially annular shape. The two sealing members 2045 and 2046 are arranged in the outside ring-shaped space 2042 so as to be spaced apart from each other in the axial direction. To be specific, the first sealing member 2045 is located close to the first cap portion 2014 in the outside ring-shaped space 2042 and seals between the casing portion 2033 and the housing main body 2011 over the entire periphery in the circumferential direction. Moreover, the first sealing member 2045 is arranged away from the inner surface of the first cap portion 2014 in a direction toward the second cap portion 2015, and a gas inflow space 2048 is formed between the first sealing member 2045 and the first cap portion 2014. Moreover, the second sealing member 2046 is located close to the second cap portion 2015 in the outside ring-shaped space 2042 and seals between the casing portion 2033 and the housing main body 2011 over the entire periphery in the circumferential direction. Furthermore, the second sealing member 2046 is arranged away from the inner surface of the second cap portion 2015 in a direction toward the first cap portion 2014, and a gas outflow space 2049 is formed between the second sealing member 2046 and the second cap portion 2015. Moreover, the two sealing members 2045 and 2046 are arranged away from each other in the axial direction, and the ring-shaped passage 2043 isolated from the two spaces 2048 and 2049 is formed between the two sealing members 2045 and 2046 in the outside ring-shaped space 2042. The hollow fiber body 2047 is provided in the ring-shaped passage 2043 formed as above.

The hollow fiber body 2047 is formed in a substantially cylindrical shape and is constituted by a plurality of hollow fibers. More specifically, the hollow fiber body 2047 is configured such that a mat-shaped hollow fiber membrane (bundle) formed by making a plurality of hollow fibers intersect with each other and laminating the plurality of hollow fibers on each other is wound around an outer peripheral surface of the casing portion 2033. The hollow fiber membrane is wound such that the thickness of the hollow fiber body 2047 substantially coincides with an interval between the casing portion 2033 and the housing main body 2011. To be specific, an outer peripheral surface of the hollow fiber body 2047 is in contact with an inner peripheral surface of the housing main body 2011 over the entire periphery, and the hollow fiber body 2047 is formed along the inner peripheral surface of the housing main body 2011. A first end portion of the hollow fiber body 2047 configured as above penetrates the first sealing member 2045, and a second end portion of the hollow fiber body 2047 penetrates the second sealing member 2046. To be specific, the two spaces 2048 and 2049 communicate with each other through the inner holes of the plurality of hollow fibers constituting the hollow fiber body 2047.

Moreover, gaps are formed among the plurality of hollow fibers constituting the hollow fiber body 2047, and the blood flows through the gaps. To be specific, the blood introduced to the ring-shaped passage 2043 flows through the gaps in the hollow fiber body 2047 toward one side in the axial direction (i.e., from the second cap portion 2015 toward the first cap portion 2014). Moreover, since the blood flows through the gaps, the blood can be brought into contact with the hollow fibers. As described above, the inner holes of the hollow fibers are connected to the two spaces 2048 and 2049. The gas inlet port 2018 formed so as to correspond to the gas inflow space 2048 is connected to the gas inflow space 2048, and the gas is introduced through the gas inlet port 2018 to the gas inflow space 2048. The introduced gas flows inside the plurality of hollow fibers to the gas outflow space 2049. Moreover, the gas discharge port 2019 formed so as to correspond to the gas outflow space 2049 is connected to the gas outflow space 2049, and the gas flowing out from the hollow fibers is discharged through the gas discharge port 2019 to the atmosphere.

The gas taken into the gas inlet port 2018 contains a large amount of oxygen. Therefore, when the blood having high carbon dioxide concentration contacts the hollow fibers, the gas exchange is performed between the blood and the hollow fibers. To be specific, carbon dioxide is removed from the blood, and oxygen is added to the blood. With this, the carbon dioxide concentration of the blood decreases, and the oxygen concentration of the blood increases. As above, the blood flows through the ring-shaped passage 2043 toward one side in the axial direction while being subjected to the gas exchange by the gas exchanger 2004. Moreover, a downstream side portion of the ring-shaped passage 2043 is larger in diameter than the other portion of the ring-shaped passage 2043 in the radially outward direction, more specifically, one of axial portions of the outside ring-shaped space 2042 (i.e., a portion close to the first cap portion 2014) is larger in diameter than the other portion of the outside ring-shaped space 2042 in the radially outward direction.

Figure 20:
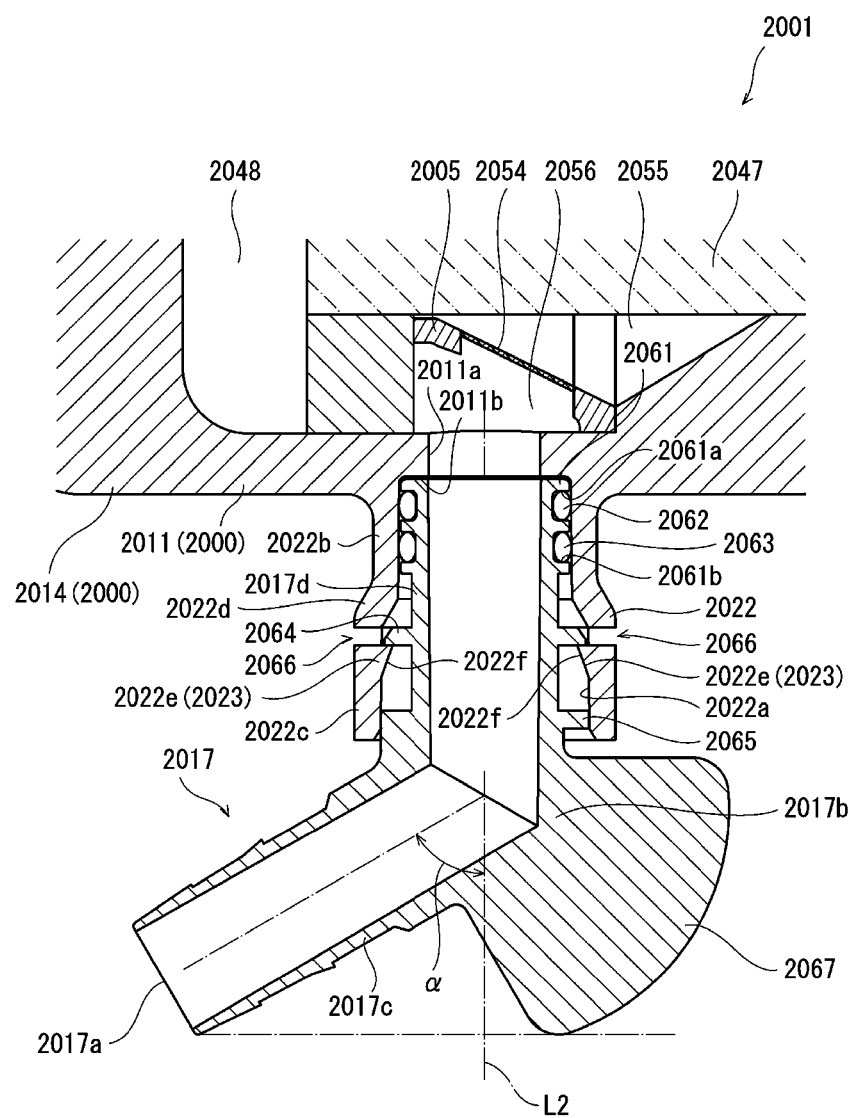
FIG. 20 is an enlarged sectional view showing a region X1 of FIG. 19 in the third disclosure.

More specifically, as shown in FIG. 20, a recess 2050 that is recessed in the radially outward direction is formed at the inner peripheral surface of the housing main body 2011. The recess 2050 is formed at the inner peripheral surface over the entire periphery in the circumferential direction so as to be close to the first cap portion 2014. Moreover, a portion of the recess 2050 which portion is located at the other side in the axial direction is formed in a tapered shape that tapers toward the other side in the axial direction. On the other hand, a portion of the recess 2050 which portion extends from an axially middle portion to a portion at one side is formed in parallel with the axis L1, and the first sealing member 2045 is arranged at the middle portion of the recess 2050. According to the recess 2050 configured as above, an outer peripheral space 2052 having a substantially ring shape is formed between the outer peripheral surface of the hollow fiber body 2047 and the inner peripheral surface of the housing main body 2011, and the blood flowing through the ring-shaped passage 2043 is introduced to the outer peripheral space 2052. Moreover, the hollow fiber body 2047 is not interposed in the outer peripheral space 2052, and the filter member 2005 is arranged to remove foreign matters contained in the blood.

The filter member 2005 is formed in a substantially truncated cone shape and includes a filter 2054. The filter 2054 can transmit the blood and remove foreign matters (such as blood clots) contained in the blood. To be specific, the filter member 2005 removes the foreign matters from the blood which passes through the filter member 2005.

As described above, the filter member 2005 configured as above is arranged in the outer peripheral space 2052. With this, the outer peripheral space 2052 is divided into two regions that are a bubble storing space 2055 and a discharge passage 2056. To be specific, the outer peripheral space 2052 is divided by the filter member 2005 into the bubble storing space 2055 which is a region located upstream of the filter member 2005 and faces the hollow fiber body 2047 and the discharge passage 2056 which is a region located downstream of the filter member 2005 (i.e., a region located at a radially outer side of the bubble storing space 2055). Therefore, the blood introduced from the ring-shaped passage 2043 to the outer peripheral space 2052 first enters into the bubble storing space 2055 and then flows through the filter member 2005 to the discharge passage 2056.

When the blood flowing as above is introduced from the blood inflow port 2016 to the housing 2002, the blood carries bubbles in some cases. Such bubbles are carried by the flow of the blood through the heat exchanger tubes 2032b and the radial passages 2041 to the ring-shaped passage 2043. As described below, the bubbles are basically taken in the hollow fiber body 2047 but are not completely taken in the hollow fiber body 2047. Therefore, the bubbles which were not taken in the hollow fiber body 2047 are carried by the blood to the bubble storing space 2055. Moreover, the blood flows from the bubble storing space 2055 through the filter member 2005 to the discharge passage 2056. However, since the mesh size of the filter member 2005 is small, most of the bubbles carried cannot pass through the filter member 2005 and are blocked by the filter member 2005. To be specific, the bubbles are stopped in front of the filter member 2005 and flow upward along the filter member 2005. The bubbles having flowed upward are gathered and accumulated at and around a highest portion of the bubble storing space 2055, i.e., at and around a top portion 2059a. Thus, the bubbles are captured in the bubble storing space 2055. Moreover, it is difficult for the filter member 2005 to block all the bubbles, and the bubbles unexpectedly pass through the filter member 2005 in some cases. Such bubbles are gathered at and around a top portion 2059a that is a highest portion of the recess 2050. To discharge the bubbles gathered as above, a first air vent port 2057 and a second air vent port 2058 are formed at an upper portion of the housing main body 2011.

The first air vent port 2057 is formed in a substantially cylindrical shape, and an inner hole of the first air vent port 2057 is open in the vicinity of the top portion 2059a. Moreover, a tube (not shown) is connected to the first air vent port 2057, and a pinch or an openable-closable cock is provided at a portion of the tube. By detaching the pinch or opening the cock, the bubbles accumulated at and around the top portion 2059a can be substantially entirely discharged through the first air vent port 2057. The second air vent port 2058 is formed in a substantially cylindrical shape as with the first air vent port 2057, and an inner hole of the second air vent port 2058 is open in the vicinity of the top portion 2050b. Moreover, a tube (not shown) is connected to the second air vent port 2058, and a pinch or an openable-closable cock is provided at a portion of the tube. By detaching the pinch or opening the cock, the bubbles accumulated at and around the top portion 2050b can be substantially entirely discharged through the second air vent port 2058. The blood having been separated from the bubbles as above flows downward along the discharge passage 2056. To discharge the blood, which has been separated as above, to the outside of the housing 2002, the blood outflow port 2017 is provided at a position of a lower portion of the outer peripheral surface of the housing main body 2011 which position corresponds to the discharge passage 2056. With this, the blood flowing downward along the discharge passage 2056 is discharged through the blood outflow port 2017 to a blood discharge tube. Hereinafter, the configuration of the blood outflow port 2017 will be described in more detail with reference to FIG. 20.

As described above, the blood outflow port 2017 is provided at the lower portion of the outer peripheral surface of the housing main body 2011, and a port attaching portion 2022 at which the blood outflow port 2017 is provided is integrally provided at the lower portion of the outer peripheral surface of the housing main body 2011. The port attaching portion 2022 is formed in a substantially cylindrical shape and projects downward from the housing main body 2011. It should be noted that the port attaching portion 2022 does not necessarily have to extend vertically downward and may extend downward and be inclined in any of front, rear, left, and right directions. Moreover, outer and inner peripheral surfaces of a tip end-side portion 2022c of the port attaching portion 2022 are larger in diameter than outer and inner peripheral surfaces of a base end-side portion 2022b of the port attaching portion 2022, and a tapered portion 2022d is formed between the base end-side portion 2022b and the tip end-side portion 2022c. The tapered portion 2022d increases in diameter as it extends from the base end-side portion 2022b toward the tip end-side portion 2022c. The outer and inner peripheral surfaces of the base end-side portion 2022b and the outer and inner peripheral surfaces of the tip end-side portion 2022c are smoothly connected to each other by the tapered portion 2022d. The blood outflow port 2017 is inserted into the port attaching portion 2022 formed as above.

The blood outflow port 2017 has a substantially cylindrical shape and is formed so as to be bent. The blood outflow port 2017 is bent at a bent portion 2017b that is an intermediate portion thereof. To be specific, the blood outflow port 2017 is configured such that a lower portion 2017c that is a portion (i.e., a tip end-side portion) located at a tip end side of the bent portion 2017b forms an angle cc with respect to an upper portion 2017d that is a portion (i.e., a base end-side portion) located at a base end side of the bent portion 2017b. The angle α is, for example, 30 degrees or more and 120 degrees or less. In the present embodiment, the angle α is 60 degrees. It should be noted that the blood outflow port 2017 is configured such that: the angle α is set to 30 degrees or less in order that the tube is prevented from being bent when the artificial lung device 2001 is placed on or provided close to a floor or the like; and the angle α is set to 120 degrees or less to prevent a case where since an outflow opening 2017a at a tip end of the blood outflow port 2017 is located too close to the housing main body 2011, the tube cannot be attached to the outflow opening 2017a.

The upper portion 2017d of the blood outflow port 2017 having such shape is inserted into the port attaching portion 2022, and the blood outflow port 2017 is rotatable about an axis L2 of the upper portion 2017d. To be specific, the blood outflow port 2017 is attached to the port attaching portion 2022 so as to be rotatable. By rotating the blood outflow port 2017, the outflow opening 2017a can be directed in various directions. Moreover, an inner hole 2022a of the port attaching portion 2022 communicates with the outer peripheral space 2052 (more specifically, the discharge passage 2056) through a communication passage 2011a formed at the housing main body 2011. Therefore, the blood flowing downward along the discharge passage 2056 enters into the blood outflow port 2017 through the communication passage 2011a and is then discharged through the outflow opening 2017a to the arterial blood tube.

As described above, the blood outflow port 2017 configured as above is rotatably attached to the port attaching portion 2022 by being inserted into the port attaching portion 2022, i.e., the blood outflow port 2017 is configured separately from the housing main body 2011. Therefore, it is necessary to take measures against a case where the blood leaks from between the blood outflow port 2017 and the port attaching portion 2022 and a case where the blood outflow port 2017 comes off from the port attaching portion 2022. To realize such measures, the blood outflow port 2017 is configured as below.

To prevent the leakage of the blood, the blood outflow port 2017 includes a seal attaching portion 2061 in the vicinity of an upper end of the upper portion 2017d. The seal attaching portion 2061 is formed over the entire periphery of an upper portion 2017d in the circumferential direction and projects in the radially outward direction beyond the other portion of the upper portion 2017d. Two seal grooves 2061a and 2061b are formed at the seal attaching portion 2061 having such shape. The two seal grooves 2061a and 2061b are located away from each other in a direction along the axis L2, i.e., in the upper-lower direction in the present embodiment and extend over the entire periphery of the seal attaching portion 2061 in the circumferential direction. To be specific, each of the two seal grooves 2061a and 2061b is formed in an annular shape, and sealing members 2062 and 2063 are respectively accommodated in the seal grooves 2061a and 2061b. The sealing members 2062 and 2063 are, for example, O rings and are respectively accommodated in the seal grooves 2061a and 2061b in a compressed state. With this, the sealing members 2062 and 2063 are interposed and seal between an outer peripheral surface of the blood outflow port 2017 and an inner peripheral surface of the port attaching portion 2022.

Moreover, the two seal grooves 2061a and 2061b are different in length in the radial direction, i.e., depth from each other. Specifically, the first seal groove 2061a located at the upper side (i.e., a base end side) is formed deeper than the second seal groove 2061b located at the lower side (i.e., a tip end side). On the other hand, the two sealing members 2062 and 2063 are substantially the same in dimensions as each other. Therefore, when the blood outflow port 2017 is attached to the port attaching portion 2022, compressibility of the second sealing member 2063 fitted in the second seal groove 2061b is higher than that of the first sealing member 2062 fitted in the first seal groove 2061a. To be specific, the second sealing member 2063 can realize higher sealing property than the first sealing member 2062 and can be arranged closer to the opening of the port attaching portion 2022. With this, even if the blood leaks from between the first sealing member 2062 and the port attaching portion 2022 toward the opening of the port attaching portion 2022, the second sealing member 2063 can prevent the further leak toward the opening. Moreover, since only one of the two sealing members 2062 and 2063 is made to have high compressibility, an increase in sliding resistance generated by the sealing members when rotating the blood outflow port can be suppressed. It should be noted that the present embodiment is configured such that the compressibility of the sealing member 2062 and the compressibility of the sealing member 2063 are made different from each other by the depths of the two seal grooves 2061a and 2061b, but the present embodiment does not necessarily have to have such configuration. For example, the compressibility of the sealing member 2062 and the compressibility of the sealing member 2063 may be made different from each other in such a manner that the two sealing members 2062 and 2063 are made different in dimensions from each other, or the compressibility of the sealing member 2062 and the compressibility of the sealing member 2063 may be made different from each other in such a manner that the shapes of the two sealing members 2062 and 2063 are made different from each other. Moreover, the two sealing members 2062 and 2063 may be configured such that the compressibility of the sealing member 2062 and the compressibility of the sealing member 2063 are substantially equal to each other.

Moreover, to prevent the blood outflow port 2017 from coming off from the port attaching portion 2022, two flanges 2064 and 2065 are formed at a portion of the upper portion 2017d other than the seal attaching portion 2061. The two flanges 2064 and 2065 are formed at an outer peripheral surface of the upper portion 2017d over the entire periphery in the circumferential direction and project in the radially outward direction from the outer peripheral surface of the upper portion 2017d. Moreover, the two flanges 2064 and 2065 are arranged away from each other in the upper-lower direction. The first flange 2064 arranged at the upper side out of the two flanges 2064 and 2065 is formed at a position slightly away from the seal attaching portion 2061 in the lower direction. Moreover, the first flange 2064 is arranged so as to be located lower than the tapered portion 2022d of the port attaching portion 2022 when the blood outflow port 2017 is attached to the port attaching portion 2022. Moreover, an engaging portion 2023 is formed at a position of the inner peripheral surface of the port attaching portion 2022 which position corresponds to the first flange 2064.

The engaging portion 2023 is engaged with the first flange 2064 to prevent the blood outflow port 2017 from coming off from the port attaching portion 2022. In the present embodiment, the engaging portion 2023 is constituted by a pair of engagement pieces 2022e. The pair of engagement pieces 2022e are arranged so as to be spaced apart from each other in the circumferential direction at even intervals, i.e., separated from each other by about 180 degrees in the circumferential direction. The pair of engagement pieces 2022e extend at the inner peripheral surface of the port attaching portion 2022 in the circumferential direction. The pair of engagement pieces 2022e project inward in the radial direction from the inner peripheral surface of the port attaching portion 2022. Each of the pair of engagement pieces 2022e is formed in a tapered shape such that a projection amount thereof increases in a direction from the lower side to the upper side. To be specific, a portion of the inner peripheral surface of the port attaching portion 2022 at which portion the pair of engagement pieces 2022e realize engagement decreases in diameter in the direction from the lower side to the upper side. Therefore, by inserting the blood outflow port 2017 into the opening of the port attaching portion 2022 to attach the blood outflow port 2017 to the port attaching portion 2022, the first flange 2064 is brought into contact with the inner surfaces of the pair of engagement pieces 2022e, i.e., tapered surfaces 2022f of the pair of engagement pieces 2022e. By further pushing the blood outflow port 2017 upward to attach the blood outflow port 2017 to the port attaching portion 2022, the first flange 2064 slides on the tapered surfaces 2022f while pushing the pair of engagement pieces 2022e outward. Therefore, the blood outflow port 2017 can be further inserted toward the base end side of the port attaching portion 2022. It should be noted that an upper outer peripheral edge of the first flange 2064 is largely chamfered such that the first flange 2064 easily slides on the tapered surfaces 2022f. With this, the first flange 2064 is bent downward and slides on the tapered surfaces 2022f, and thus, the blood outflow port 2017 can be pushed into the base end side of the port attaching portion 2022.

Moreover, by pushing the blood outflow port 2017, the entire first flange 2064 reaches the base end side beyond the upper surfaces of the pair of engagement pieces 2022e, i.e., the entire first flange 2064 gets over the pair of engagement pieces 2022e. With this, the first flange 2064 elastically returns and spreads, and thus, gets on and is engaged with the upper surfaces of the pair of engagement pieces 2022e. Since the first flange 2064 and the pair of engagement pieces 2022e are engaged with each other, the first flange 2064 is supported by the pair of engagement pieces 2022e. Even when downward force acts on the blood outflow port 2017, the blood outflow port 2017 can be prevented from coming off from the port attaching portion 2022. It should be noted that the blood outflow port 2017 receives downward force from the blood introduced through the discharge passage 2056, and therefore, is pushed downward at all times while being used. As described above, since the first flange 2064 is supported by the pair of engagement pieces 2022e, the blood outflow port 2017 can be prevented from coming off from the port attaching portion 2022 while being used. A pair of windows 2066 are formed at an outer peripheral surface of the port attaching portion 2022 configured as above, i.e., at an inner peripheral surface of the tip end-side portion 2022c.

The pair of windows 2066 are formed so as to penetrate the tip end-side portion 2022c in the radial direction and are arranged so as to respectively correspond to the pair of engagement pieces 2022e. To be specific, lower end edges of the pair of windows 2066 are substantially flush with upper surfaces of the pair of engagement pieces 2022e, and heights of the pair of windows 2066 substantially coincide with a height of the first flange 2064. Moreover, the pair of windows 2066 extend in the circumferential direction, and the positions of both end edges of each of the pair of windows 2066 in the circumferential direction substantially coincide with the positions of both end edges of the corresponding engagement piece 2022e. The pair of windows 2066 formed as above can promote the deformation of the pair of engagement pieces 2022e and its periphery in the port attaching portion 2022. With this, when the blood outflow port 2017 is pushed into the port attaching portion 2022, the pair of engagement pieces 2022e can be made to spread by the first flange 2064 of the blood outflow port 2017 to some extent, and therefore, the blood outflow port 2017 can be easily pushed into the port attaching portion 2022. Moreover, since the first flange 2064 supported by the pair of engagement pieces 2022e can be seen from the outside through the pair of windows 2066, the engaging state of the first flange 2064 can be visually confirmed from the outside. The blood outflow port 2017 engaged as above is configured such that the first flange 2064 is placed on and engaged with the pair of engagement pieces 2022e. Therefore, when the blood outflow port 2017 swings with respect to the port attaching portion 2022 in the front, rear, left, or right direction, the first flange 2064 comes off from one of the pair of engagement pieces 2022e in some cases. To prevent such case, the second flange 2065 is formed at the upper portion 2017d in addition to the first flange 2064.

The second flange 2065 is formed in the vicinity of the bent portion 2017b of the upper portion 2017d. With the first flange 2064 engaged with the pair of engagement pieces 2022e, the second flange 2065 is located inside the port attaching portion 2022. Moreover, an outer diameter of the second flange 2065 is substantially equal to or slightly smaller than a diameter of the inner peripheral surface of the tip end-side portion 2022c of the port attaching portion 2022. Therefore, when the blood outflow port 2017 swings with respect to the port attaching portion 2022 in the front, rear, left, or right direction, the second flange 2065 contacts the inner peripheral surface of the port attaching portion 2022, and therefore, the swinging of the blood outflow port 2017 is restricted. With this, it is possible to prevent a case where the blood outflow port 2017 swings relative to the port attaching portion 2022 in the front, rear, left, or right directions, and therefore, the first flange 2064 comes off from one of the pair of engagement pieces 2022e.

It should be noted that the inner hole 2022a of the port attaching portion 2022 is formed larger in diameter than the communication passage 2011a, and therefore, a ring-shaped surface 2011b having a substantially annular shape is formed around the communication passage 2011a. Moreover, an inner diameter of the blood outflow port 2017 is substantially equal to that of the communication passage 2011a. Therefore, the blood outflow port 2017 is attached to the port attaching portion 2022 such that an upper end of the blood outflow port 2017 is opposed to the ring-shaped surface 2011b. Upward movement of the blood outflow port 2017 is restricted by the ring-shaped surface 2011b. As above, the blood outflow port 2017 is rotatably attached to the port attaching portion 2022 such that the movement thereof in the upper, lower, left, right, front, and rear directions is restricted. Moreover, a holding portion 2067 is integrally provided at the bent portion 2017b of the blood outflow port 2017 so as to rotate the blood outflow port 2017 about the axis L2.

The holding portion 2067 is configured to be holdable by a user with, for example, fingers. The holding portion 2067 configured as above is integrally provided at an outside portion (in FIG. 20, a portion having a larger curvature radius) of an outer peripheral surface of the bent portion 2017b and projects in an obliquely downward direction (in FIG. 20, a right and obliquely downward direction) so as to be away from the outside portion of the outer peripheral surface of the bent portion 2017b. Moreover, the holding portion 2067 is provided at the bent portion 2017b, and in addition, both end portions of the holding portion 2067 respectively extend to the lower portion 2017c and the upper portion 2017d. The holding portion 2067 is formed in a substantially fan shape. Moreover, the holding portion 2067 is formed in a plate shape, and as described above, is holdable by a user with, for example, fingers. By holding the holding portion 2067 and rotating the holding portion 2067 about the axis L2, the blood outflow port 2017 can be rotated about the axis L2.

Since the holding portion 2067 configured as above is formed so as to project from the bent portion 2017b, the holding portion 2067 serves as a rib and improves the rigidity of the blood outflow port 2017. Moreover, the holding portion 2067 projects downward and extends to a level that is the same in height as a lower end of the outflow opening 2017a of the blood outflow port 2017. Therefore, if the artificial lung device 2001 falls from, for example, the suspending device, the holding portion 2067 can land first. The holding portion 2067 is a plate-shaped member extending in an obliquely downward direction and has high rigidity with respect to load generated at the time of the landing. Therefore, even when the holding portion 2067 lands first at the time of falling, the holding portion 2067 hardly breaks. Moreover, when the holding portion 2067 lands first at the time of the falling, a lowermost position of the holding portion 2067 lands first, and impact acts on the holding portion 2067 in the upper direction. To be specific, the impact at the time of the falling acts on the blood outflow port 2017 in a direction along the axis L2. Since the upper portion 2017d of the blood outflow port 2017 is formed along the axis L2, the blood outflow port 2017 has high rigidity with respect to the load acting in the direction along the axis L2. Therefore, since the holding portion 2067 lands first at the time of the falling, the blood outflow port 2017 can be prevented from breaking.

In the artificial lung device 2001 configured as above, the venous blood taken out from the vein flows through the blood inflow port 2016 into the blood inflow space 2014b in the housing 2002. The blood in the blood inflow space 2014b flows into the heat exchanger tubes 2032b of the tube bundle 2032 and advances through the heat exchanger tubes 2032b to the pair of radial passages 2041. When the blood flows through the heat exchanger tubes 2032b, the blood is subjected to the heat exchange with the medium in the internal space 2031a, and thus, the temperature of the blood is adjusted. The blood having been adjusted in temperature advances through the pair of radial passages 2041 to the ring-shaped passage 2043, flows through the gaps in the hollow fiber body 2047 arranged in the ring-shaped passage 2043, and further advances toward the discharge passage 2056 located at one side in the axial direction. Gas containing a large amount of oxygen flows inside the hollow fibers of the hollow fiber body 2047. When the blood contacts the hollow fibers of the hollow fiber body 2047 while flowing through the gaps, carbon dioxide is removed from the blood, and oxygen is added to the blood. With this, the oxygen concentration of the blood can be increased. Then, the blood flows from the bubble storing space 2055 through the filter member 2005 to the discharge passage 2056. The blood flowing as above carries foreign matters, such as clots, in some cases. However, since the blood passes through the filter member 2005, such foreign matters are captured before entering into the discharge passage 2056. Then, the blood from which the foreign matters are removed advances downward along the discharge passage 2056, is discharged through the blood outflow port 2017 to the blood discharge tube, and returns to the artery through the blood discharge tube.

Figure 21:
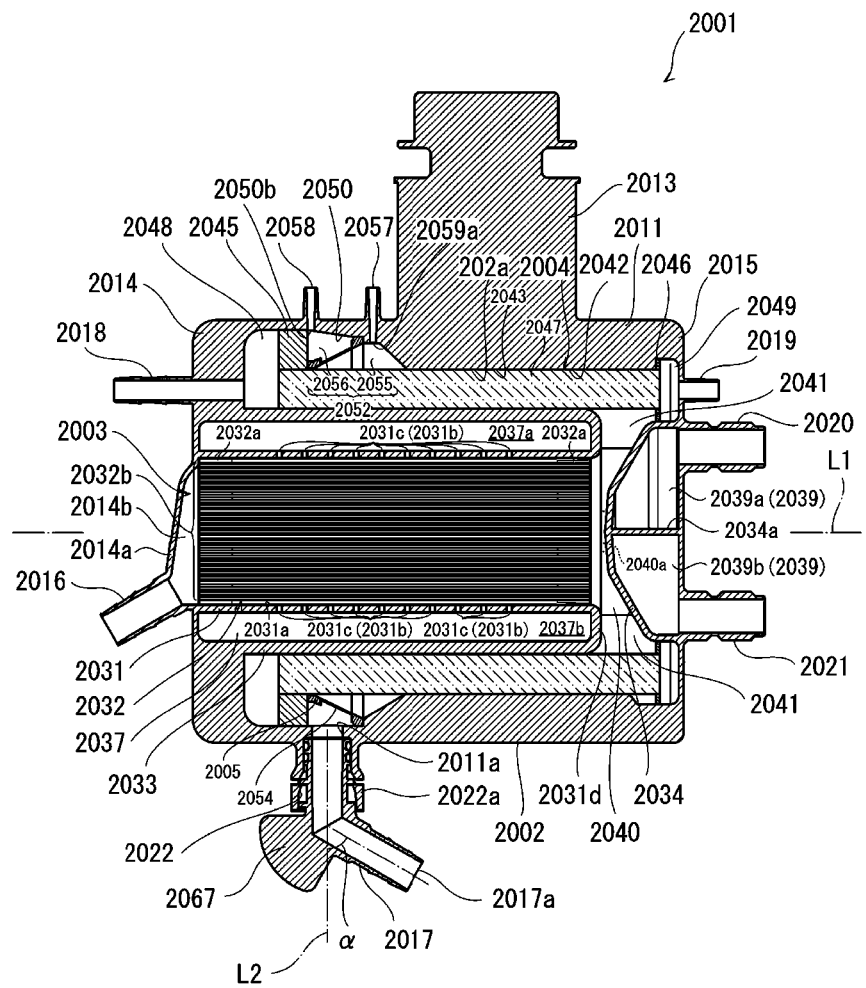
FIG. 21 is a sectional view showing that a tip end of the blood outflow port is directed toward a right side on the paper surface in the artificial lung device of FIG. 19 in the third disclosure.
Figure 22A:
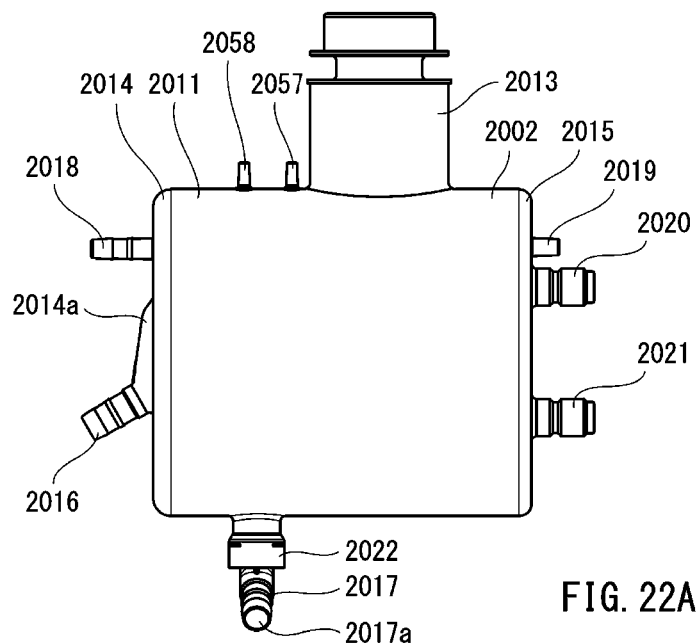
FIGS. 22A and 22B are front views showing that the blood outflow port of the artificial lung device of FIG. 18 in the third disclosure is directed in various directions.
Figure 22B:
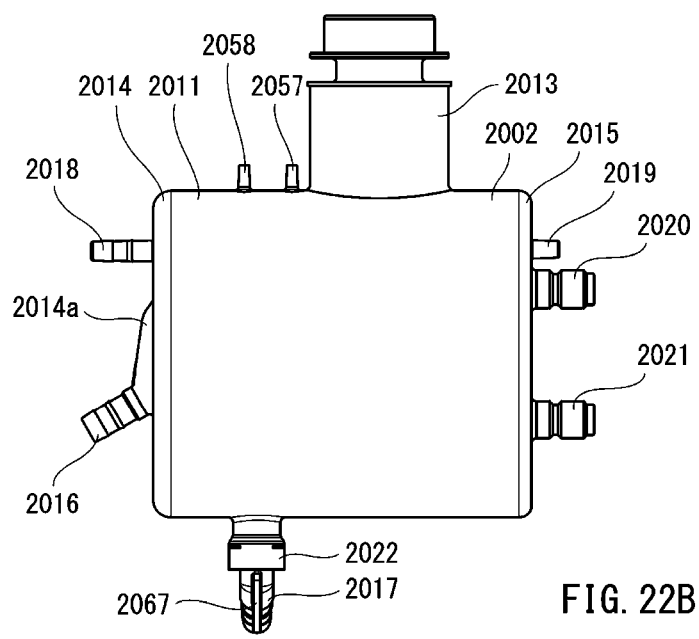

As described above, in the artificial lung device 2001 having such functions, the blood outflow port 2017 is attached to the port attaching portion 2022 so as to be rotatable. Therefore, by rotating the blood outflow port 2017, the direction of the blood outflow port 2017 (i.e., the direction of the outflow opening 2017a) can be changed regardless of the directions of the housing main body 2011 and the blood inflow port 2016. For example, as shown in FIG. 21, the outflow opening 2017a can be directed to a side (i.e., the right side) opposite to the blood inflow port 2016. Moreover, by rotating the blood outflow port 2017, the outflow opening 2017a can be directed to a paper surface near side with respect to the blood inflow port 2016 directed to the left side as shown in FIG. 22A, or the outflow opening 2017a can be directed to a paper surface deep side with respect to the blood inflow port 2016 directed to the left side as shown in FIG. 22B. Since the direction of the outflow opening 2017a can be changed by 360 degrees as above, the degree of freedom regarding the arrangement position, direction, and the like of the artificial lung device 2001 and the degree of freedom regarding the arrangement positions, directions, and the like of apparatuses to which the artificial lung device 2001 is attached improve. To be specific, the routing of the tubes connecting the blood inflow port 2016, the blood outflow port 2017, and the apparatuses can be facilitated.

Moreover, according to the artificial lung device 2001, typically, the pressure of the blood flowing through the blood outflow port 2017 is lower than the pressure of the blood flowing through the blood inflow port 2016. Therefore, when the blood outflow port 2017 is configured to be rotatable, the leakage of the blood can be prevented more surely than when the blood inflow port 2016 is configured to be rotatable. Furthermore, when the blood outflow port 2017 is configured to be rotatable, the leakage of the blood can be prevented by a seal structure having low pressure resistance performance. Therefore, the cost for the artificial lung device 2001 can be reduced.

Other Embodiments

Figure 23:
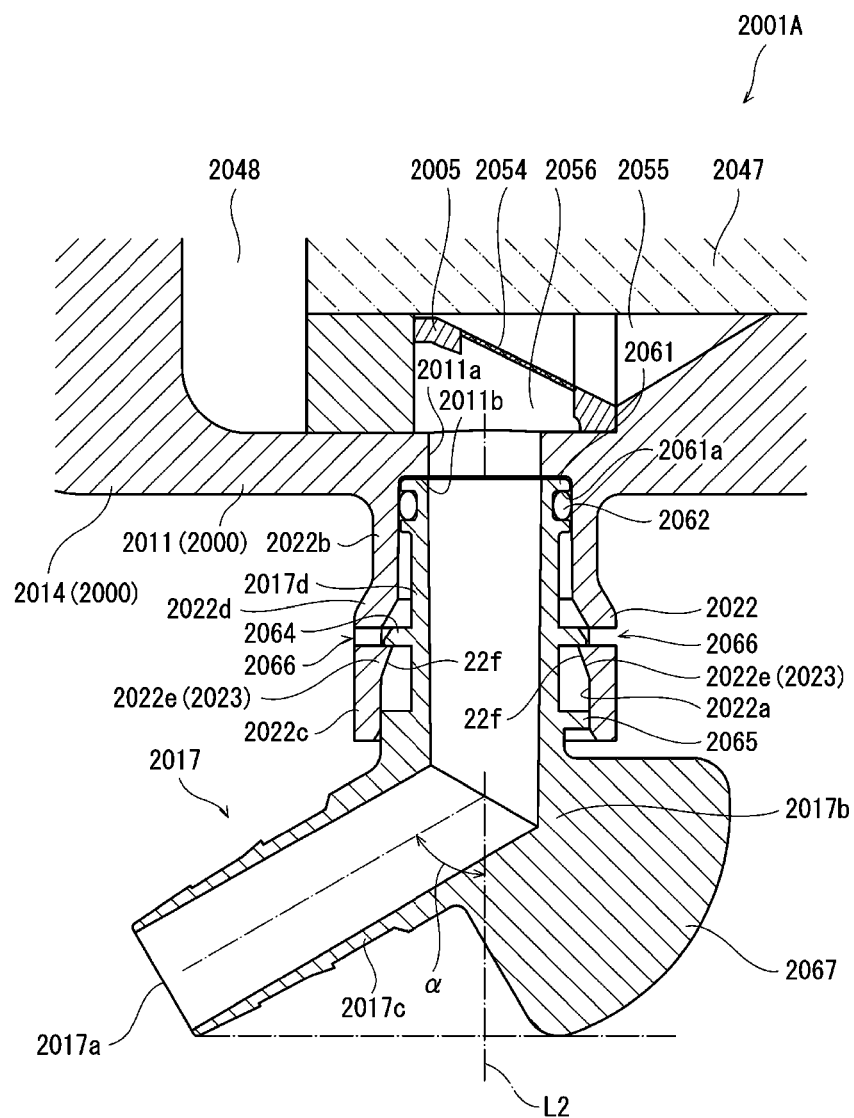
FIG. 23 is an enlarged sectional view showing the blood outflow port and its vicinity in the artificial lung device according to another embodiment of the third disclosure.

In the artificial lung device 2001 of the present embodiment, the two sealing members 2062 and 2063 are provided at the blood outflow port 2017. However, the number of sealing members does not necessarily have to be two. For example, only the first sealing member 2062 may be provided as in an artificial lung device 2001A shown in FIG. 23, or a third sealing member may be additionally provided. Moreover, the second flange 2065 does not necessarily have to be provided at the blood outflow port 2017, or a third flange may be newly formed in addition to the two flanges 2064 and 2065. The engaging portion 2023 does not necessarily have to be constituted by the pair of engagement pieces 2022e. The engaging portion 2023 may be formed in a tapered shape as with the pair of engagement pieces 2022e at the inner peripheral surface of the port attaching portion 2022 over the entire periphery in the circumferential direction.

Moreover, in the artificial lung device 2001 of the present embodiment, the housing main body 2011 is formed in a substantially cylindrical shape. However, the shape of the housing main body 2011 does not necessarily have to be such shape. For example, the housing main body 2011 may be formed in a substantially square tube shape or is only required to be tubular and arranged such that an axis thereof is substantially parallel to the horizontal direction while the housing main body 2011 is used. Moreover, the artificial lung device 2001 to which the blood outflow port 2017 is applied is not limited to the horizontal type artificial lung device according to the present embodiment. For example, the blood outflow port 2017 is applicable to a vertical type artificial lung device in which both end portions of the housing 2002 are arranged in the upper-lower direction.

Moreover, in the artificial lung device 2001 of the present embodiment, the blood outflow port 2017 is inserted into the inner hole 2022a of the port attaching portion 2022. However, the blood outflow port 2017 does not necessarily have to have this configuration. To be specific, the base end-side portion of the blood outflow port 2017 may include an inner hole into which the port attaching portion 2022 can be inserted, and the port attaching portion 2022 may be inserted into the inner hole. Furthermore, in the artificial lung device 2001 of the present embodiment, the port attaching portion 2022 is provided at the housing main body 2011 so as to extend in the upper-lower direction. However, the port attaching portion 2022 does not necessarily have to have this configuration. For example, the port attaching portion 2022 may be integrally provided at the first cap member 2014 so as to extend in parallel with the axis L1 of the housing main body 2011. With this, the blood outflow port 2017 is arranged such that the base end-side portion thereof extends in parallel with the axis L1, and the tip end-side portion thereof is inclined in any of the upper, lower, left, and right directions so as to form a predetermined angle with respect to the base end-side portion thereof. Therefore, by rotating the blood outflow port 2017 about the axis of the base end-side portion thereof, the outflow opening 2017a can be directed in any direction, such as the upper, lower, left, or right direction.

Moreover, in the artificial lung device 1 of the present embodiment, the port attaching portion 2022 is provided at the lower portion of the housing main body 2011. However, the present embodiment does not necessarily have to have this structure. For example, the port attaching portion 2022 is formed in a substantially tubular shape and is externally attached to one of opening end portions of the housing main body 2011. The port attaching portion 2022 includes an insertion hole or an insertion portion, and the blood outflow port 2017 is attached to the insertion hole or the insertion portion so as to be rotatable. Moreover, in the artificial lung device 2001 of the present embodiment, the blood outflow port 2017 is configured to be rotatable. However, the blood inflow port 2016 may be configured to be rotatable.

Moreover, in the artificial lung device 2001 of the present embodiment, the holding portion 2067 projects downward and extends to a level that is the same in height as the lower end of the outflow opening 2017a of the blood outflow port 2017. However, the present embodiment is not limited to this. The holding portion 2067 may project downward but does not have to reach the lower end of the outflow opening 2017a of the blood outflow port 2017. When the holding portion 2067 is configured to project downward, the blood outflow port 2017 can be configured such that the rigidity thereof is high, and the resistance thereof to the impact at the time of the falling is high.

An embodiment according to the fourth disclosure will be described.

Figure 24:
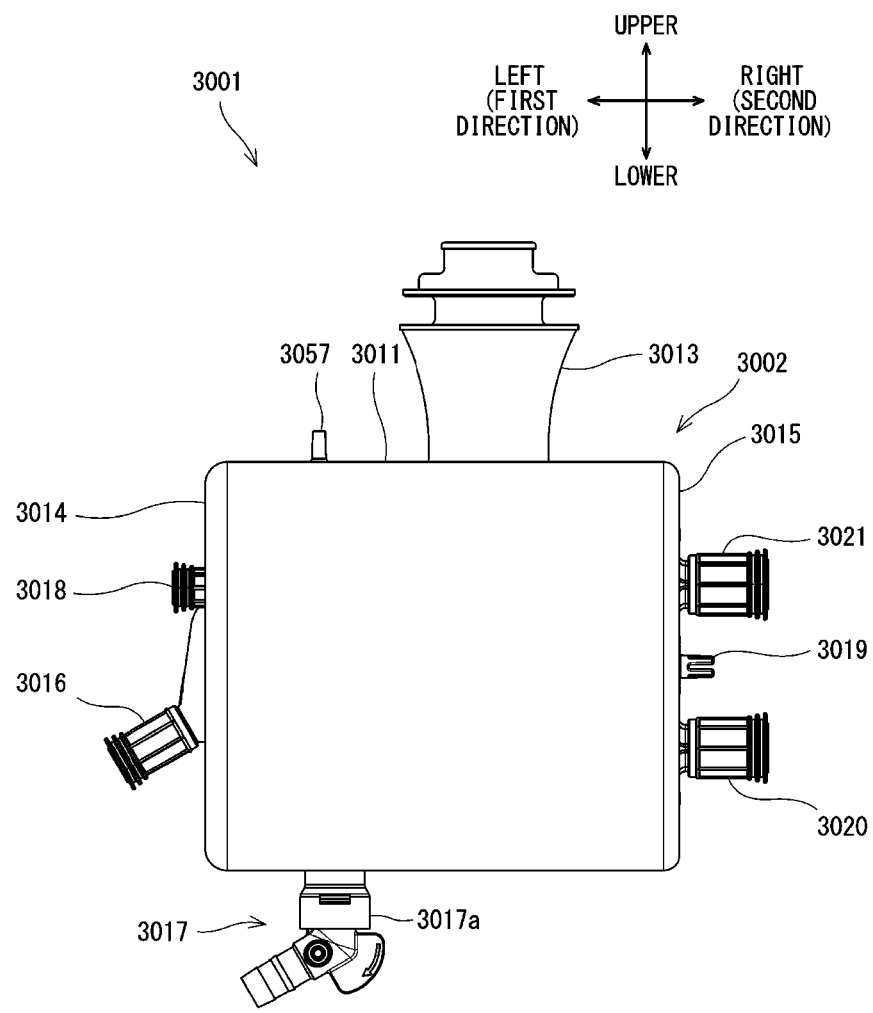
FIG. 24 is a front view showing appearance of the artificial lung device according to one embodiment of the fourth disclosure of the present invention.

In a surgical operation, such as a heart surgical operation, which is performed after the movement of the heart of a patient is stopped, an artificial lung device 3001 shown in FIG. 24 is used as a substitute for the function of the lung of the patient. The artificial lung device 3001 removes carbon dioxide contained in the blood of the patient and adds oxygen to the blood, i.e., has the gas exchange function. Moreover, the artificial lung device 3001 has the heat exchange function to adjust the temperature of the blood in addition to the gas exchange. The artificial lung device 3001 having such functions includes a housing 3002, an inner tube 3003 (see FIG. 25), and a middle tube 3004 (see FIG. 25). A component including the housing 3002, the middle tube 3004, and a below-described hollow fiber body 3043 is a gas exchanger 3060.

Housing and Exterior Member

As shown in FIG. 24, the housing 3002 is formed in a substantially cylindrical shape including both end portions that are closed. The housing 3002 includes an internal space 3002a (see FIG. 25) accommodating the inner tube 3003 and the middle tube 3004. Specifically, the housing 3002 includes a housing main body 3011, a suspending portion 3013, and two cap portions 3014 and 3015.

The housing main body 3011 is formed in a substantially cylindrical shape, and the suspending portion 3013 is provided at an outer peripheral surface of an upper portion of the housing main body 3011. The suspending portion 3013 is arranged at a middle portion of the housing main body 3011 which portion is located at a middle position in a direction along an axis 3011a of the housing main body 3011. The suspending portion 3013 extends in a radially outward direction from the outer peripheral surface of the upper portion of the housing main body 3011. The suspending portion 3013 is formed in, for example, a substantially columnar shape and is suspended in such a manner that a tip end-side portion thereof is attached to an external suspending device (not shown). Therefore, the housing main body 3011 can be suspended through the suspending portion 3013, and the axis 3011a of the suspended housing main body 3011 extends in a horizontal direction.

The housing main body 3011 includes opening end portions at both sides in the direction along the axis 3011a. The opening end portion at one side (left side in FIG. 25) is closed by the cap portion 3014, and the opening end portion at the other side (right side in FIG. 25) is closed by the cap portion 3015. Each of the cap portions 3014 and 3015 is formed in a substantially circular plate shape. It should be noted that in the following description, for convenience of explanation, regarding the direction along the axis 3011a of the housing main body 3011, a side where the cap portion 3014 is located is referred to as a left side, and a side where the cap portion 3015 is located is referred to as a right side.

As shown in FIG. 24, a gas supply port 3018 is formed at the cap portion 3014. The gas supply port 3018 is formed in a substantially cylindrical shape and projects to the left side in the direction along the axis 3011a from the vicinity of an outer peripheral edge of the cap portion 3014. The gas supply port 3018 is connected to an external gas supply device (not shown) through a gas supply tube. Oxygen-containing gas supplied from the gas supply device is introduced through the gas supply port 3018 to the housing 3002.

A gas discharge port 3019 is formed at the cap portion 3015. The gas discharge port 3019 is formed in a substantially cylindrical shape and projects to the right side in the direction along the axis 3011a from the vicinity of an outer peripheral edge of the cap portion 3015. The gas discharge port 3019 is connected to the external gas supply device through a gas discharge tube. The gas discharge port 3019 is provided with a slit extending in the direction along the axis 3011a and is configured such that even when the gas discharge tube is clogged due to kink or the like, the gas flows out. It should be noted that the present embodiment is not limited to the slit as long as the gas can be discharged, and the gas discharge port 3019 may include a circular or polygonal hole.

Moreover, a gas discharge hole (not shown) is provided at a lower portion of the cap portion 3015, and the gas supplied through the gas supply port is discharged through the gas discharge hole.

A blood inflow port 3016 is formed in the vicinity of a central axis (axis which substantially coincides with the axis 3011a of the housing main body 3011) of the cap portion 3014. The blood inflow port 3016 is formed in a substantially cylindrical shape and projects from a lower side of the central axis of the cap portion 3014 in a left and obliquely downward direction. A venous blood tube (not shown) is connected to the blood inflow port 3016, and venous blood is introduced through the venous blood tube and the blood inflow port 3016 into the housing main body 3011.

A blood outflow port 3017 is formed at a position of a lower portion (portion opposite to the suspending portion 3013) of the outer peripheral surface of the housing main body 3011 which position is located at the left side of a center of the artificial lung device 3001 in the direction along the axis 3011a. More specifically, the blood outflow port 3017 includes a port attaching portion 3017a and a port main body portion 3017b (see FIG. 25). The port attaching portion 3017a is formed in a substantially cylindrical shape. The port attaching portion 3017a is provided at the lower portion of the outer peripheral surface of the housing main body 3011 and projects downward. The port main body portion 3017b is inserted into the port attaching portion 3017a from a lower side. The port main body portion 3017b is formed in a substantially cylindrical shape. The port main body portion 3017b projects downward from a lower end of the port attaching portion 3017a and is bent in an obliquely downward direction at a tip side of the lower end of the port attaching portion 3017a. An arterial blood tube (not shown) is connected to the blood outflow port 3017 (port main body portion 3017b). The arterial blood generated in the artificial lung device 3001 is delivered through the arterial blood tube to an outside.

A medium inflow port 3020 and a medium outflow port 3021 are provided at the cap portion 3015. The medium inflow port 3020 and the medium outflow port 3021 are arranged so as to sandwich a central axis of the cap portion 3015 and be spaced apart from each other in an upper-lower direction. The two ports 3020 and 3021 do not necessarily have to be spaced apart from each other in the upper-lower direction and may be arranged so as to be spaced apart from each other in a left-right direction. Each of the two ports 3020 and 3021 is formed in a substantially cylindrical shape and projects from the cap portion 3015 toward the right side in the direction along the axis 3011a. The medium inflow port 3020 is connected to a medium supply tube (not shown), and a heat medium, such as hot water or cold water, from the medium supply tube is introduced through the medium inflow port 3020 into the housing 3002. The medium outflow port 3021 is connected to a medium discharge tube (not shown), and the heat medium in the housing 3002 is discharged through the medium outflow port 3021 and the medium discharge tube to the outside of the housing 3002.

The inner tube 3003 and the middle tube 3004 are accommodated in the internal space 3002*a* of the housing 3002 so as to be coaxial with each other. A blood chamber 3003*c*, a heat medium partial chamber 3035 (3033 and 3034), and a gas exchange chamber 3045 are formed by the housing 3002, the middle tube 3004, and the inner tube 3003.

An outer diameter of the middle tube 3004 is smaller than an inner diameter of the housing main body 3011. The middle tube 3004 is arranged at the housing main body 3011 such that a center axis of the middle tube 3004 and a center axis of the housing main body 3011 coincide with each other. With this, a ring-shaped space is formed between an outer peripheral surface of the middle tube 3004 and an inner peripheral surface of the housing main body 3011, and this ring-shaped space constitutes the gas exchange chamber 3045. The hollow fiber body 3043 is provided in the gas exchange chamber 3045. The gas exchange with the blood is performed in the gas exchange chamber 3045.

The hollow fiber body 3043 is formed in a substantially cylindrical shape (or a columnar shape including an internal space) and is constituted by a plurality of hollow fibers. Specifically, the hollow fiber body 3043 is configured in such a manner that a mat-shaped hollow fiber membrane formed by making the plurality of hollow fibers intersect with each other and laminating the plurality of hollow fibers on each other is wound around the outer peripheral surface of the middle tube 3004. The hollow fiber membrane is wound such that the thickness of the hollow fiber body 3043 substantially coincides with an interval between the middle tube 3004 and the housing main body 3011. To be specific, the hollow fiber body 3043 is formed along the inner peripheral surface of the housing main body 3011 such that an outer peripheral surface of the hollow fiber body 3043 contacts the inner peripheral surface of the housing main body 3011 over the substantially entire periphery. Moreover, the hollow fiber body 3043 may be formed such that the thickness thereof is substantially equal to or larger than the interval between the middle tube 3004 and the housing main body 3011. Since the hollow fiber body 3043 has elasticity, the thickness of a portion (second-direction portion of the hollow fiber body 3043) of the hollow fiber body 3043 which portion is fitted between the middle tube 3004 and the inner peripheral surface of the housing main body 3011 when the hollow fiber body 3043 is attached between the middle tube 3004 and the housing main body 3011 substantially coincides with the interval between the middle tube 3004 and the housing main body 3011.

Moreover, since the hollow fiber body 3043 has elasticity, a portion (first-direction portion of the hollow fiber body 3043) of the hollow fiber body 3043 which portion is not fitted between the middle tube 3004 and the inner peripheral surface of the housing main body 3011 is larger in diameter than the portion (second-direction portion of the hollow fiber body 3043) of the hollow fiber body 3043 which portion is fitted between the middle tube 3004 and the inner peripheral surface of the housing main body 3011.

An annular sealing member 3050 is provided in a region located at the left side of the gas exchange chamber 3045. The sealing member 3050 forms a gas inflow space 3052 together with an inner peripheral surface of the cap portion 3014, and the gas supply port 3018 communicates with the gas inflow space 3052. Moreover, an annular sealing member 3051 is provided in a region located at the right side of the gas exchange chamber 3045. The sealing member 3051 forms a gas outflow space 3053 together with an inner peripheral surface of the cap portion 3015, and the gas discharge port 3019 communicates with the gas outflow space 3053.

The hollow fiber body 3043 is provided so as to be sandwiched between the sealing member 3050 and the sealing member 3051 from the left and right sides. The sealing member 3050 is made of a known material, such as urethane resin. The sealing member 3050 seals between the middle tube 3004 and the housing 3002 at the left side of the gas exchange chamber 3045 in an entire circumferential direction. Moreover, the sealing member 3051 seals between the middle tube 3004 and the housing 3002 at the right side of the gas exchange chamber 3045 in the entire circumferential direction. According to this configuration, the gas inflow space 3052 communicating with the gas supply port 3018 and the gas outflow space 3053 communicating with the gas discharge port 3019 communicate with each other through inner holes of the plurality of hollow fibers constituting the hollow fiber body 3043.

In the hollow fiber body 3043, gaps are provided among the plurality of hollow fibers constituting the hollow fiber body 3043. In the gas exchange chamber 3045, the blood flows through the gaps. Specifically, the blood introduced to the gas exchange chamber 3045 flows through the gaps in the hollow fiber body 3043 and flows from the right side to the left side in the direction along the axis 3011*a* while contacting the hollow fibers. Oxygen-rich gas flows from an external gas supply device through the gas supply port 3018 and the gas inflow space 3052 into the inner holes of the hollow fibers. Therefore, when the blood having high carbon dioxide concentration contacts the hollow fibers, gas exchange is performed between the blood and the gas in the hollow fibers. With this, carbon dioxide is removed from the blood, and oxygen is added to the blood. As above, the blood flows to the left side in the direction along the axis 3011*a* in the gas exchange chamber 3045 while being subjected to the gas exchange. On the other hand, the gas flowing through the inner holes of the hollow fibers flows to the right side while being subjected to the gas exchange, and returns to the external gas supply device through the gas outflow space 3053 and the gas discharge port 3019.

Figure 25:
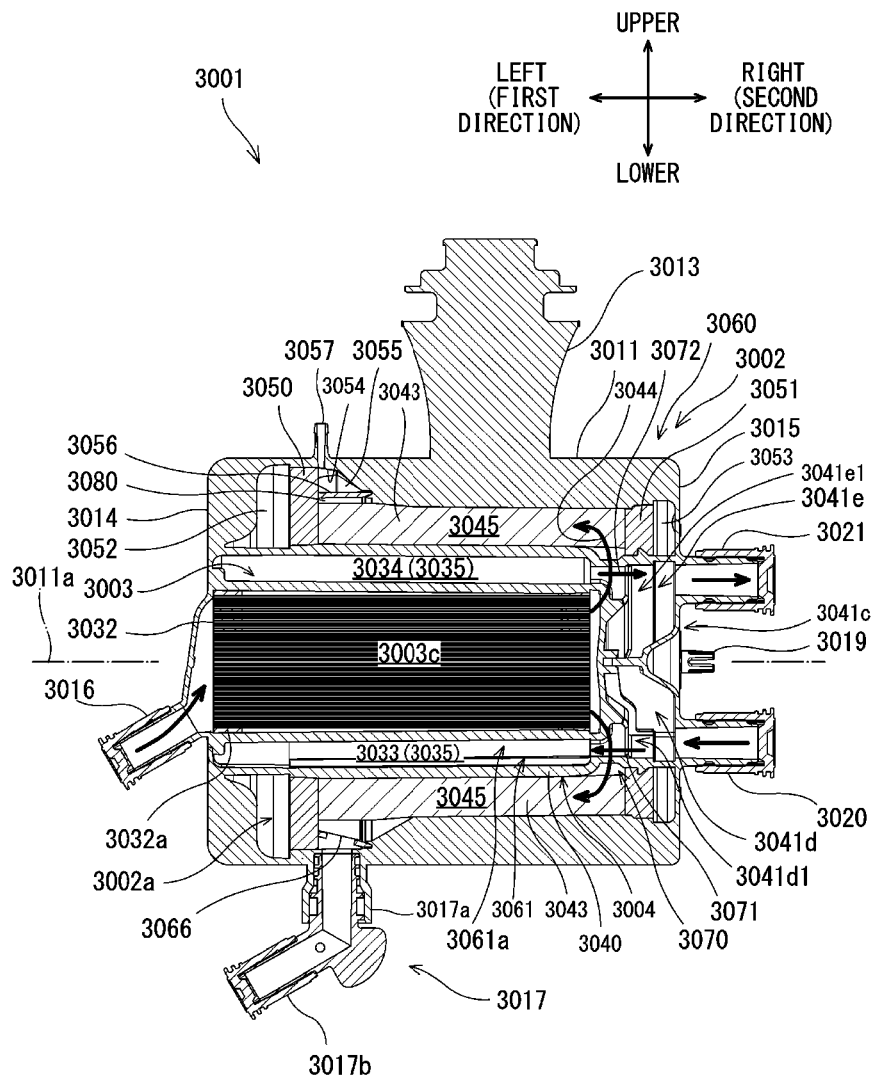
FIG. 25 is a front sectional view showing the artificial lung device of FIG. 24 in the fourth disclosure.

A downstream (left) portion of the gas exchange chamber 3045 is larger in diameter in the radially outward direction than the other portion of the gas exchange chamber 3045. Specifically, as shown in FIG. 25, a ring-shaped recess 3054 that is recessed in the radially outward direction is formed on an inner peripheral surface of a left portion of the housing main body 3011. The diameter of a left portion of the recess 3054 is substantially constant. On the other hand, a right portion of the recess 3054 tapers toward the right side, i.e., the right portion of the recess 3054 is formed in a tapered shape. The sealing member 3050 is arranged at a middle portion of the recess 3054. A portion of the recess 3054 which portion is located at the right side of the sealing member 3050 is formed in a tapered shape as described above. An outer peripheral space 3055 formed between the recess 3054 and the hollow fiber body 3043 is formed so as to surround the hollow fiber body 3043, and a lower portion of the outer peripheral space 3055 communicates with the blood outflow port 3017. According to this configuration, the blood having been subjected to the gas exchange in the gas exchange chamber 3045 is introduced to the outer peripheral space 3055 and then flows into the blood outflow port 3017.

A straightening frame 3056 having an annular shape along the outer peripheral space 3055 is provided in the outer peripheral space 3055. The straightening frame 3056 guides bubbles, carried together with the blood flowing through the gas exchange chamber 3045 while being subjected to the gas exchange, toward the hollow fiber body 3043 again and makes the bubbles be taken in the hollow fibers.

An air vent port 3057 through which the outer peripheral space 3055 communicates with the outside is provided at an upper portion of the housing main body 3011. The air vent port 3057 discharges, to the outside, the bubbles accumulated in an upper portion (bubble trap portion) of the outer peripheral space 3055. An outside opening end of the air vent port 3057 is basically covered with a cap member (not shown) Therefore, the bubbles and the blood are not discharged from the air vent port 3057 except for when the bubbles are discharged.

Middle Tube

The middle tube 3004 is arranged in the housing 3002 while forming the gas exchange chamber 3045 together with the inner peripheral surface of the housing 3002. The middle tube 3004 is arranged at a predetermined position in the internal space 3002a of the housing 3002. An outer diameter of the middle tube 3004 is smaller than an inner diameter of the housing 3002. In the present embodiment, a component including the middle tube 3004, the inner tube 3003, and a below-described tube bundle 3032 arranged in the inner tube 3003 is a heat exchanger 3061, and a region between the middle tube 3004 and the tube bundle 3032 is a heat exchange portion 3061a.

Figure 27:
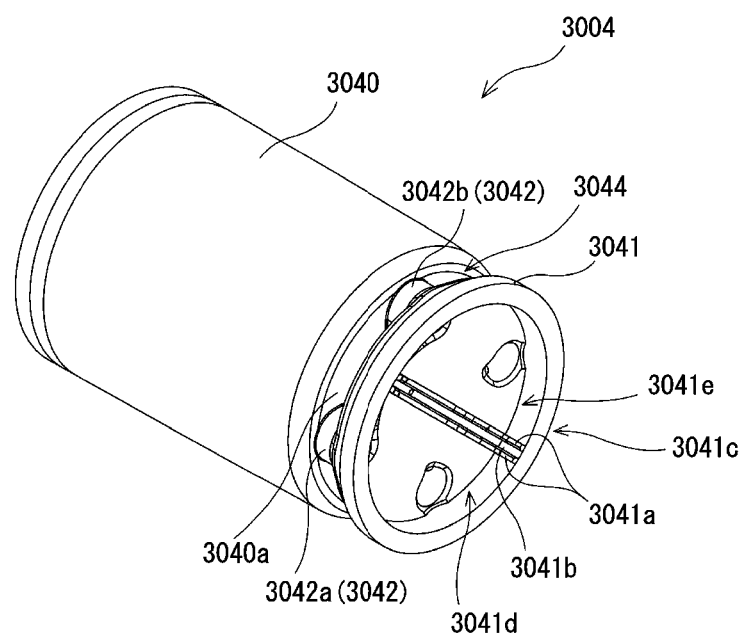
FIG. 27 is a perspective view showing a middle tube of FIG. 25 in the fourth disclosure.
Figure 28:
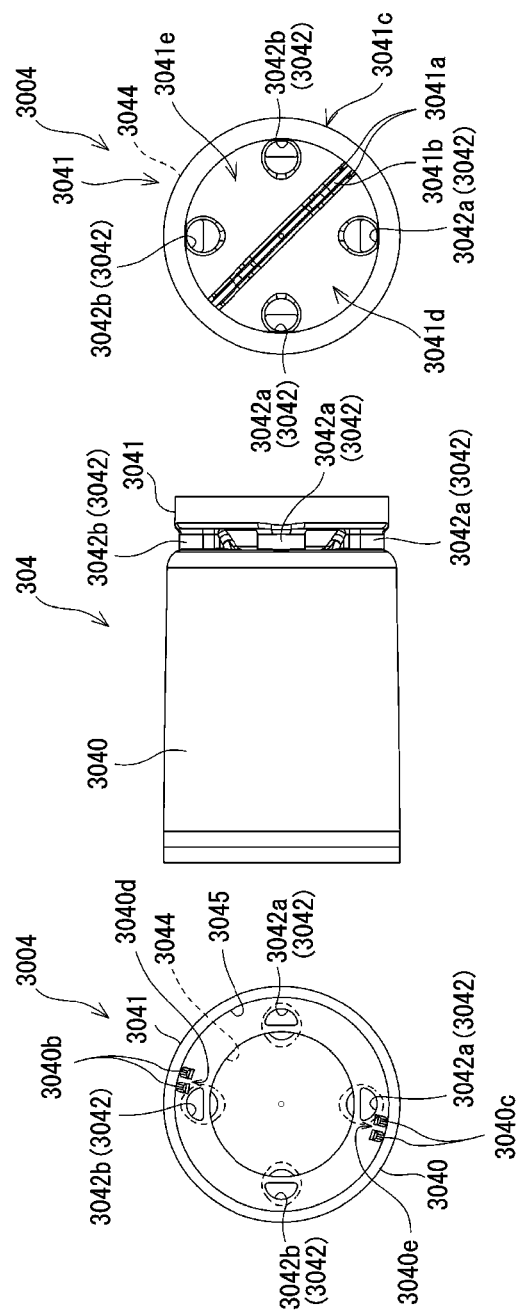
FIG. 28A is a front view showing the middle tube of FIG. 27 in the fourth disclosure.
FIG. 28B is a side view showing one side of the middle tube of FIG. 28A.
FIG. 28C is a side view showing the other side of the middle tube of FIG. 28A.

As shown in FIGS. 27 and 28A, the middle tube 3004 includes: a middle tube main body portion 3040 formed in a cylindrical shape; a dividing wall portion 3041 having a circular shape in plan view and arranged so as to be spaced apart from an end portion (end portion close to the medium outflow port 3021) of the middle tube main body portion 3040; and a plurality of hollow tubular supporting portions 3042 provided so as to extend between the dividing wall portion 3041 and the above end portion of the middle tube main body portion 3040. The tubular supporting portions 3042 are provided so as to stand on the middle tube main body portion 3040 along an axial direction of the middle tube main body portion 3040 and support the dividing wall portion 3041.

Figure 26:
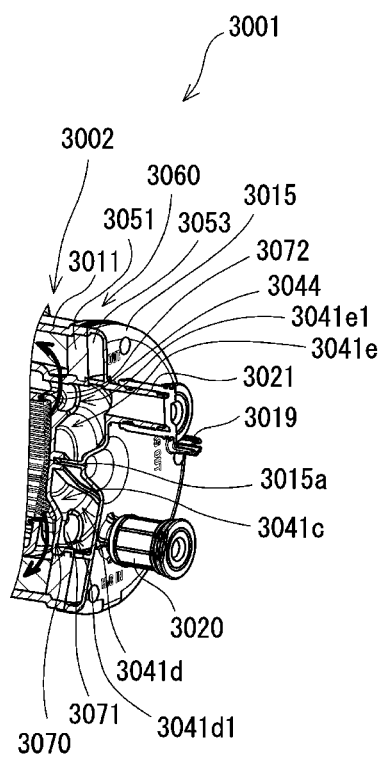
FIG. 26 is a perspective sectional view showing part of the artificial lung device of FIG. 24 in the fourth disclosure.

As shown in FIG. 26, an engaging portion 3015a is provided on the inner surface of the cap portion 3015 so as to project in an axial direction of the housing 3002 and extend in the radial direction of the cap portion 3015. As shown in FIGS. 27 and 28C, a pair of wall portions 3041a are formed on an outer surface of the dividing wall portion 3041 of the middle tube 3004. The pair of wall portions 3041a extend in the radial direction of the dividing wall portion 3041. A groove portion 3041b extending in the radial direction of the dividing wall portion 3041 is formed by the wall portions 3041a.

According to this configuration, when the middle tube 3004 is inserted into the housing 3002, and the engaging portion 3015a of the cap portion 3015 is engaged with the groove portion 3041b of the dividing wall portion 3041, the position of the middle tube 3004 relative to the cap portion 3015 can be fixed at a predetermined position. With this, the position of the middle tube 3004 relative to the housing 3002 can be fixed at a predetermined position. In this case, the middle tube 3004 is positioned relative to the housing 3002 such that the axis of the middle tube 3004 and an axis of the housing 3002 coincide with each other. Moreover, a first chamber 3041d and a second chamber 3041e are liquid-tightly isolated from each other by the engagement between the groove portion 3041b of the dividing wall portion 3041 and the engaging portion 3015a of the cap portion 3015. In the present embodiment, the middle tube 3004 and the cap portion 3015 are formed separately but may be formed integrally.

Moreover, as shown in FIG. 28B, a pair of wall portions 3040b and a pair of wall portions 3040c are provided at an inner peripheral surface of the middle tube main body portion 3040 of the middle tube 3004. The pair of wall portions 3040b extend in an axial direction of the middle tube 3004, are arranged so as to be spaced apart from each other, and project in the radial direction. The pair of wall portions 3040c are the same in shape as the pair of wall portions 3040b and are located at an opposite side of the pair of wall portions 3040b in the radial direction. A first engaged portion 3040d having a groove shape is formed between the pair of wall portions 3040b, and a second engaged portion 3040e having a groove shape is formed between the pair of wall portions 3040c. It should be noted that the first engaged portion 3040d and the second engaged portion 3040e will be described later.

The middle tube main body portion 3040 of the middle tube 3004 is formed such that both end portions thereof are open. A ring-shaped edge portion 3040a extending inward in the radial direction of the middle tube main body portion 3040 is formed at the end portion, located close to the dividing wall portion 3041, of the middle tube main body portion 3040. It should be noted that the area of an opening portion, located close to the dividing wall portion 3041, of each tubular supporting portion 3042 is smaller than the area of an opening portion, located at the opposite side, of the tubular supporting portion 3042.

As shown in FIG. 27, the dividing wall portion 3041 is formed in a mortar shape that is recessed in a direction opposite to a direction in which the cap portion 3015 is provided. The dividing wall portion 3041 forms part of an extending portion 3041c together with the inner surface of the cap portion 3015. The extending portion 3041c is a pressure adjusting space for the heat medium. The heat exchange portion 3061a includes such extending portion 3041c. To be specific, the extending portion 3041c is arranged so as to extend beyond an end portion (right end in FIG. 25) of the blood chamber 3003c outward in the axial direction of the housing 3002. To be specific, the extending portion 3041c is provided between the heat medium partial chamber 3035 and the medium inflow port 3020 (medium outflow port 3021).

The tubular supporting portions 3042 are arranged at the edge portion 3040a of the middle tube main body portion 3040 at even intervals in the circumferential direction. In the present embodiment, for example, four tubular supporting portions 3042 are provided. End portions, located close to the middle tube main body portion 3040, of the tubular supporting portions 3042 communicate with the inside of the middle tube main body portion 3040. Moreover, end portions, located close to the dividing wall portion 3041, of the tubular supporting portions 3042 communicate with the extending portion 3041c. With this, the extending portion 3041c communicates with the inside of the middle tube main body portion 3040 through the tubular supporting portions 3042.

When the middle tube 3004 is assembled to the housing 3002, i.e., when the engaging portion 3015a of the cap portion 3015 is engaged with the groove portion 3041*b* of the dividing wall portion 3041, the extending portion 3041*c* is divided into two spaces by the pair of wall portions 3041*a* and the engaging portion 3015*a*. With this, the extending portion 3041*c* is divided into the first chamber 3041*d* as a medium inflow chamber and the second chamber 3041*e* as a medium outflow chamber. The first chamber 3041*d* and the second chamber 3041*e* do not communicate with each other and are independent from each other. The first chamber 3041*d* and the second chamber 3041*e* are provided at the dividing wall portion 3041.

The first chamber 3041*d* serves as a buffer through which the heat medium flows from the medium inflow port 3020 to a below-described first heat medium partial chamber 3033. The first chamber 3041*d* includes a first chamber outlet 3041*d*1 which is in fluid communication with the first heat medium partial chamber 3033. The first chamber 3041*d* has a larger passage sectional area than the medium inflow port 3020. Moreover, a passage sectional area of the first chamber outlet 3041*d*1 is smaller than the passage sectional area of the medium inflow port 3020.

The second chamber 3041*e* serves as a buffer through which the heat medium flows from a below-described second heat medium partial chamber to the medium outflow port 3021. The second chamber 3041*e* includes a second chamber inlet 3041*e*1 which is in fluid communication with the second heat medium partial chamber 3034. The second chamber 3041*e* has a larger passage sectional area than the medium outflow port 3021. Moreover, a passage sectional area of the second chamber inlet 3041*e*1 is smaller than the passage sectional area of the medium outflow port 3021.

According to this configuration, as shown in FIG. 28C, the heat medium from the medium inflow port 3020 flows through the first chamber 3041*d* into first supporting portions 3042*a* that are two adjacent tubular supporting portions among the four tubular supporting portions 3042. The heat medium having flowed into the first supporting portions 3042*a* flows into the first heat medium partial chamber 3033 in the middle tube 3004. As above, the first supporting portions 3042*a* constitute a first medium passage 3071 through which the medium inflow port 3020 and the first heat medium partial chamber 3033 are in fluid communication with each other. A passage sectional area of the first medium passage 3071 is smaller than the passage sectional area of the medium inflow port 3020. Moreover, the total of the passage sectional areas of the two first supporting portions 3042*a* is equal to the passage sectional area of the medium inflow port 3020.

Moreover, although details will be described later, the heat medium from the second heat medium partial chamber 3034 in the middle tube 3004 flows into second supporting portions 3042*b* that are the other two adjacent tubular supporting portions among the four tubular supporting portions 3042. Then, the heat medium is introduced through the second chamber 3041*e* to the medium outflow port 3021. As above, the second supporting portions 3042*b* constitute a second medium passage 3072 through which the second heat medium partial chamber 3034 and the medium outflow port 3021 are in fluid communication with each other. A passage sectional area of the second medium passage 3072 is smaller than the passage sectional area of the medium outflow port 3021. Moreover, the total of the passage sectional areas of the two second supporting portions 3042*b* is equal to the passage sectional area of the medium outflow port 3021.

According to the above configuration, the heat medium flows into the artificial lung device 3001 from the right side, flows to the left side, performs the heat exchange with the blood, and flows out from the left side of the artificial lung device 3001 to the right side (heat medium flow configuration). This flow of the heat medium is one example, and the present embodiment is not limited to this.

A blood passage 3044 is formed in a region between the inner tube 3003 and the middle tube 3004, i.e., between the end portion of the middle tube main body portion 3040 and the dividing wall portion 3041, more specifically, between the right end portion of the middle tube main body portion 3040 and the dividing wall portion 3041, the region being a region except for the four tubular supporting portions 3042. The blood passage 3044 communicates with a downstream end (right end in FIG. 25) of the below-described tube bundle 3032, an opening portion, located close to the dividing wall portion 3041, of the middle tube main body portion 3040, and an inlet provided at one side (right side in FIG. 25) of the gas exchange chamber 3045 extending in the axial direction of the housing 3002. To be specific, the blood flows through the blood inflow port 3016 into the artificial lung device 1 from the left side, flows to the right side, turns back through the blood passage 3044, and flows out through the blood outflow port 3017 arranged at the left side of the artificial lung device 3001 (blood flow configuration).

According to this configuration, since the blood is made to flow in the artificial lung device 3001 from the left side to the right side, a passage length of the blood is secured, and this realizes the adequate heat exchange. In addition, since the blood inflow port 3016 and the medium outflow port 3021 are arranged at positions opposite to each other at the artificial lung device 3001, sanitary risks are reduced.

Configurations which achieve the above two effects are the above heat medium flow configuration and the above blood flow configuration. To realize these configurations, as shown in FIGS. 25 and 26, the blood passage 3044 needs to be formed so as to intersect with the tubular supporting portions 3042. Therefore, the tubular supporting portions 3042 constituting the first medium passage 3071 and the second medium passage 3072 are arranged so as to extend across the blood passage 3044, i.e., intersect with the blood passage 3044. As above, the artificial lung device 3001 includes a bridge structure 3070 which forms the blood passage 3044 and the first and second medium passages 3071 and 3072 arranged so as to intersect with the blood passage 3044.

Inner Tube

Figure 29:
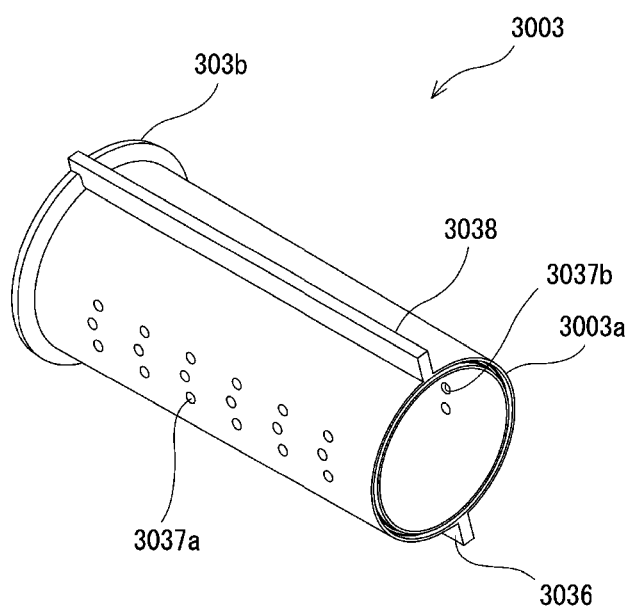
FIG. 29 is a perspective view showing an inner tube of FIG. 25 in the fourth disclosure.

As shown in FIG. 29, the inner tube 3003 adjusts the temperature of the venous blood introduced into the housing 3002 and is formed so as to extend in a direction that is the same as the axial direction of the housing 3002 and the axial direction of the middle tube 3004. In the present embodiment, a length (axial length) of the inner tube 3003 is larger than a length (axial length) of the middle tube 3004.

As shown in FIG. 25, the blood chamber 3003*c* including a first end and a second end is provided in the inner tube 3003 forming part of the heat exchange portion 3061*a*. The tube bundle 3032 in which the blood flows is arranged so as to be inserted into the blood chamber 3003*c* such that an axial direction of the tube bundle 3032 coincides with an axial direction of the inner tube 3003. The tube bundle 3032 is an assembly of a plurality of heat exchange pipes. The heat exchange pipes are long and small-diameter tubes made of a material, such as stainless steel, having high heat conductivity, and the blood from the blood inflow port 3016 flows into the heat exchange pipes. A second end of the inner tube 3 communicates with an opening portion, located close to the dividing wall portion 3041 (located at the right side in FIG. 25), of the middle tube main body portion 3040.

An outer diameter of the inner tube 3003 is smaller than an inner diameter of the middle tube 3004. Moreover, the inner tube 3003 is positioned relative to the middle tube 3004 such that an axis of the inner tube 3003 and the axis of the middle tube 3004 coincides with each other. According to this configuration, the annular heat medium partial chamber 3035 through which the heat medium flows is formed between an outer peripheral surface of the inner tube 3003 and an inner peripheral surface of the middle tube 3004. It should be noted that the heat medium partial chamber 3035 is included in the heat exchange portion 3061a.

As shown in FIG. 25, a pair of tube supporting bodies 3032a each having a circular plate shape are provided in the inner tube 3003. An outer diameter of each tube supporting body 3032a substantially coincides with an inner diameter of the inner tube 3003. One of the tube supporting bodies 3032a is inserted into one of ends of the inner tube 3003, and the other tube supporting body 3032a is inserted into the other end of the inner tube 3003. Then, the heat exchange pipes constituting the tube bundle 3032 are arranged in the inner tube 3003 such that: one ends of the heat exchange pipes are inserted into holes (not shown) radially provided at one of the tube supporting bodies 3032a; and the other ends of the heat exchange pipes are inserted into holes (not shown) radially provided at the other tube supporting body 3032a. With this, both opening end portions of the inner tube 3003 are sealed by the pair of tube supporting bodies 3032a. It should be noted that a known material, such as urethane resin, is used for the tube supporting bodies 3032a.

As shown in FIG. 29, a ring-shaped engaging portion 3003b that is larger in diameter than the other portion of the inner tube 3003 is provided at an end portion of the inner tube 3003 which portion is located opposite to an end portion 3003a located close to the cap portion 3015. In a state where the inner tube 3003 is positioned relative to the middle tube 3004 such that the axis of the inner tube 3003 coincides with the axis of the middle tube 3004, the ring-shaped engaging portion 3003b and the end portion, located close to the ring-shaped engaging portion 3003b, of the inner tube 3003 project from the middle tube 3004. Then, in a state where the middle tube 3004 is arranged in the housing 3002, the ring-shaped engaging portion 3003b is engaged with the inner surface of the cap portion 3014. With this, the inner tube 3003 is fixed to the cap portion 3014 of the housing 3002.

Moreover, as shown in FIG. 29, a first engaging portion 3038 and a second engaging portion 3036 are provided at the outer peripheral surface of the inner tube 3003. The first engaging portion 3038 extends in the axial direction of the inner tube 3003 and projects in the radially outward direction from the outer peripheral surface of the inner tube 3003. As with the first engaging portion 3038, the second engaging portion 3036 extends in the axial direction of the inner tube 3003, projects in the radially outward direction from the outer peripheral surface of the inner tube 3003, and is located at an opposite side of the first engaging portion 3038 in the radial direction.

According to this configuration, when positioning the inner tube 3003 in the middle tube 3004, the inner tube 3003 is made to slide to be inserted into the middle tube 3004 in a state where the first engaging portion 3038 of the inner tube 3003 is engaged with the first engaged portion 3040d of the middle tube 3004, and the second engaging portion 3036 of the inner tube 3003 is engaged with the second engaged portion 3040e of the middle tube 3004. In a state where the inner tube 3003 is assembled in the middle tube 3004 as above, the end portion 3003a of the inner tube 3003 contacts the inner surface of the edge portion 3040a of the middle tube main body portion 3040. With this, the blood chamber 3003c and the heat medium partial chamber 3035 are liquid-tightly isolated from each other. Moreover, the ring-shaped engaging portion 3003b of the inner tube 3003 projects outward from the middle tube main body portion 3040 and is engaged with the inner surface of the cap portion 3014.

As above, when the inner tube 3003 is positioned in the middle tube 3004, as shown in FIG. 25, the annular heat medium partial chamber 3035 is divided into the first heat medium partial chamber 3033 and the second heat medium partial chamber 3034 by two walls formed by the engagement between the first engaging portion 3038 and the first engaged portion 3040d and the engagement between the second engaging portion 3036 and the second engaged portion 3040e. The first heat medium partial chamber 3033 and the second heat medium partial chamber 3034 are liquid-tightly isolated from each other by the first engaging portion 3038, the first engaged portion 3040d, the second engaging portion 3036, and the second engaged portion 3040e. The first heat medium partial chamber 3033 communicates with the medium inflow port 3020, and the second heat medium partial chamber 3034 communicates with the medium outflow port 3021.

As shown in FIG. 29, the inner tube 3003 includes: a plurality of first heat medium holes 3037a which are in fluid communication with the blood chamber 3003c and the first heat medium partial chamber 3033 and provided so as to be lined up in the axial direction of the inner tube 3003; and a plurality of second heat medium holes 3037b which are in fluid communication with the blood chamber 3003c and the second heat medium partial chamber 3034 and provided so as to be lined up in the axial direction of the inner tube 3003. The first and second heat medium holes 3037a and 3037b are formed so as to penetrate the thickness of the inner tube 3003. The first heat medium holes 3037a are arranged symmetrically with respect to the second heat medium holes 3037b across the blood chamber 3003c (see FIG. 25). The first and second heat medium holes 3037a and 3037b are the same in diameter as each other and are, for example, holes each having a diameter of 3 mm. For example, each of the number of first heat medium holes 3037a and the number of second heat medium holes 3037b may be set to 18. For example, the first heat medium holes 3037a (second heat medium holes 3037b) are arranged in six rows lined up in the axial direction of the inner tube 3003, and each row includes three first heat medium holes 3037a (three second heat medium holes 3037b) along a direction orthogonal to the axial direction. A pair of recesses may be provided at the outer surface of the inner tube 3003 so as to extend in the axial direction of the inner tube 3003 such that when the inner tube 3003 is positioned in the middle tube 3004, and the first heat medium partial chamber 3033 and the second heat medium partial chamber 3034 are separately formed, the volumes of the first heat medium partial chamber 3033 and the second heat medium partial chamber 3034 become large. In this case, the first heat medium holes 3037a may be arranged at one of the recesses, and the second heat medium holes 3037b may be arranged at the other recess.

In the artificial lung device 3001 configured as above, after the venous blood taken out from the vein flows through the blood inflow port 3016 into the housing 3002, the blood flows into the heat exchange pipes of the tube bundle 3032. After the blood flows through the heat exchange pipes, the blood flows through the blood passage 3044 into the gas exchange chamber 3045. To be specific, the blood having flowed out from an outlet of the blood chamber 3003c flows in a direction intersecting with the axis of the housing 3002. More specifically, the blood having flowed out from the outlet of the blood chamber 3003c flows so as to cross the extending portion 3041c by the blood passage 3044. Since the blood flows so as to spread in the radial direction of the housing 3002 by the blood passage 3044 as above, blood stagnation hardly occurs.

The heat medium having flowed through the medium inflow port 3020 into the housing 3002 flows through the extending portion 3041c (first chamber 3041d) into the two first supporting portions 3042a communicating with the first chamber 3041d in a state where an increase in pressure loss is suppressed. Then, the heat medium flows from the first heat medium partial chamber 3033 through the first heat medium holes 3037a into the blood chamber 3003c. With this, the heat medium flows on the surfaces of the heat exchange pipes of the tube bundle 3032 provided in the blood chamber 3003c.

Then, when the blood flows inside the heat exchange pipes of the tube bundle 3032, the heat exchange is performed between the blood and the heat medium in the blood chamber 3003c, and thus, the temperature of the blood is adjusted. As described above, the blood having been adjusted in temperature flows through the blood passage 3044 into the gas exchange chamber 3045. Then, the blood flows through the gaps in the hollow fiber body 3043 provided in the gas exchange chamber 3045 and contacts the hollow fibers of the hollow fiber body 3043. With this, carbon dioxide is removed from the blood, and oxygen is added to the blood. Thus, the oxygen concentration of the blood increases, and the blood is discharged from the blood outflow port 3017 as the arterial blood.

The heat medium having been subjected to the heat exchange flows from the blood chamber 3003c through the second heat medium holes 3037b into the second heat medium partial chamber 3034. Then, after the heat medium flows through the two second supporting portions 3042b communicating with the second chamber 3041e, the heat medium flows through the second chamber 3041e (extending portion 3041c) an is discharged through the medium outflow port 3021.

As described above, according to the artificial lung device 3001 of the present embodiment, the blood flows into the blood inflow port 3016 provided at a first end side of the housing 3002, flows through the heat exchanger 3061 and a second end side of the heat medium partial chamber 3035, and flows through the blood passage 3044 to the gas exchange chamber 3045. With this, the heat exchange with respect to the blood is adequately performed. Moreover, since the blood inflow port 3016 is provided at the first end side of the housing 3002, and the medium outflow port 3021 is provided at a second end side of the housing 3002, sanitation is improved.

Specifically, the blood passage 3044 is formed so as to intersect with the four tubular supporting portions 3042. To be specific, the four tubular supporting portions 3042 that are passages for the heat medium are configured as bridge passages which extend across the blood passage 3044. According to this configuration, since the blood flows in the artificial lung device 3001 from the left side to the right side, the passage length of the blood can be secured, and this can realize the adequate heat exchange. In addition, since the blood inflow port 3016 and the medium outflow port 3021 can be arranged at positions opposite to each other at the artificial lung device 1, sanitary risks can be avoided.

Moreover, in the present embodiment, the passage sectional area of the first medium passage 3071 is smaller than the passage sectional area of the medium inflow port 3020, and the passage sectional area of the second medium passage 3072 is smaller than the passage sectional area of the medium outflow port 3021. According to this configuration, the artificial lung device 1 can be prevented from increasing in size in the radial direction. With this, priming volume decreases. As a result, a burden on a patient is small.

Moreover, when the passage sectional areas of the first medium passage 3071 and the second medium passage 3072 are made small to reduce the priming volume as above, passage constriction occurs, and the pressure loss of the heat medium increases. However, in the present embodiment, the extending portion 3041c having the heat exchange function is provided between the group of the first heat medium partial chamber 3033 and the second heat medium partial chamber 3034 and the group of the medium inflow port 3020 and the medium outflow port 3021. The increase in pressure loss of the heat medium can be suppressed by the existence of the extending portion 3041c. Moreover, since the housing 3002 does not have to be increased in size in the radial direction by the existence of the extending portion 3041c, the priming volume can be reduced.

Moreover, in the present embodiment, the first chamber 3041d has a passage sectional area larger than the passage sectional area of the medium inflow port 3020, and the second chamber 3041e has a passage sectional area larger than the passage sectional area of the medium outflow port 3021. With this, the increase in pressure loss can be further suppressed.

Moreover, in the present embodiment, the passage sectional area of the first chamber outlet 3041d1 is smaller than the passage sectional area of the medium inflow port 3020, and the passage sectional area of the second chamber inlet 3041e1 is smaller than the passage sectional area of the medium outflow port 3021. With this, the increase in diameter of the housing 3002 can be suppressed, and the priming volume can be further reduced.

Moreover, in the present embodiment, the heat medium partial chamber 3035 (the first heat medium partial chamber 3033 and the second heat medium partial chamber 3034) communicating with the blood chamber 3003c is formed between the outer peripheral surface of the inner tube 3003 and the inner peripheral surface of the middle tube 3004. To be specific, the heat medium partial chamber 3035 is formed in the inner tube 3003 so as to extend along an axial direction of the blood chamber 3003c in which the blood flows through the tube bundle 3032. With this, the heat medium can be supplied uniformly with respect to the flow direction of the blood. Thus, the heat exchange with the blood can be uniformly and adequately performed.

Moreover, in the present embodiment, when positioning the inner tube 3003 in the middle tube 3004, the inner tube 3003 is made to slide to be inserted into the middle tube 3004 in a state where the first engaging portion 3038 of the inner tube 3003 is engaged with the first engaged portion 3040d of the middle tube 3004, and the second engaging portion 3036 of the inner tube 3003 is engaged with the second engaged portion 3040e of the middle tube 3004. According to this configuration, the inner tube 3003 is easily positioned relative to the middle tube 3004. Moreover, when the inner tube 3003 is positioned and arranged in the middle tube 3004, the heat medium partial chamber 3035 is divided into the first heat medium partial chamber 3033 and the second heat medium partial chamber 3034. Therefore, it is unnecessary to additionally provide a dividing wall which divides the heat medium partial chamber 3035 into a chamber in which the heat medium having not yet been subjected to the heat exchange flows and a chamber in which the heat medium having been subjected to the heat exchange flows.

Moreover, the present embodiment includes the blood passage 3044 through which the blood flowing out from the outlet of the blood chamber 3003c flows in the direction intersecting with the axis of the housing 3002. If the blood flowing out from the outlet of the blood chamber 3003c is made to flow in the direction along the axis 3011a of the housing 3002, the flow of the blood extends in the direction along the axis 3011a of the housing 3002, and therefore, the housing 3002 further increases in size in the direction along the axis 3011a. On this account, the priming volume increases. On the other hand, when the blood passage 3044 through which the blood flows in the direction intersecting with the axis is adopted, the housing 3002 can be prevented from increasing in size in the direction along the axis 3011a. With this, the priming volume can be further reduced.

Moreover, in the present embodiment, since the middle tube 3004 is arranged in the housing 3002 while forming the gas exchange chamber 3045 together with the inner peripheral surface of the housing 3002, the gas exchange chamber 3045 can be arranged inside the housing 3002. Therefore, the artificial lung device 3001 can be prevented from increasing in diameter as compared to when the gas exchange chamber is provided outside the housing. As a result, the priming volume can be reduced.

Moreover, in the present embodiment, the total of the passage sectional areas of the first supporting portions 3042a is equal to the passage sectional area of the medium inflow port 3020, and the total of the passage sectional areas of the second supporting portions 3042b is equal to the passage sectional area of the medium outflow port 3021. With this, the increase in pressure loss of the heat medium can be suppressed.

Moreover, in the present embodiment, since the dividing wall portion 3041 is formed in a mortar shape that is recessed in a direction opposite to a direction in which the cap portion 3015 is provided, the volumes of the first chamber 3041d and the second chamber 3041e can be easily secured. As a result, the pressure loss of the heat medium from the medium inflow port 3020 hardly increases.

Moreover, in the present embodiment, the inner tube 3003 includes the plurality of first and second heat medium holes 3037a and 3037b provided so as to be lined up in the axial direction of the inner tube 3003. The first and second heat medium holes 3037a and 3037b are, for example, holes each having a diameter of 3 mm. The first heat medium holes 3037a (second heat medium holes 3037b) are arranged in six rows lined up in the axial direction of the inner tube 3003, and each row includes three first heat medium holes 3037a (three second heat medium holes 3037b) along a direction orthogonal to the axial direction. With this, the efficiency of the heat exchange between the blood and the heat medium can be improved, and the increase in pressure loss of the heat medium due to the heat medium passage can be suppressed.

Furthermore, in the present embodiment, the first heat medium holes 3037a are arranged symmetrically with respect to the second heat medium holes 3037b across the blood chamber 3003c. With this, the flow of the heat medium can be made orthogonal to the flow direction of the blood in the blood chamber 3003c, and therefore, the stirring efficiency of the heat medium with respect to the blood improves. Thus, the efficiency of the heat exchange improves.

Other Embodiment

The present invention is not limited to the above embodiments, and various modifications may be made within the scope of the present invention. Examples are as below.

In the above embodiment, the blood outflow port 3017 is provided at the outer peripheral surface of the housing 3002. However, the above embodiment is not limited to this. As with the blood inflow port 3016, the blood outflow port 3017 may be provided at the cap portion 3014.

Moreover, in the above embodiment, the blood flows inside the heat exchange pipes of the tube bundle 3032, and the heat medium flows around the heat exchange pipes of the tube bundle 3032. However, the above embodiment is not limited to this. The heat medium may flow inside the heat exchange pipes of the tube bundle 3032, and the blood may flow around the heat exchange pipes.

Moreover, in the above embodiment, the middle tube 3004 is arranged so as to be inserted into the housing 3002. However, the above embodiment is not limited to this. The middle tube 3004 and the housing 3002 may be formed integrally.

Moreover, in the above embodiment, the inner tube 3003 is arranged so as to be inserted into the middle tube 3004. However, the above embodiment is not limited to this. The inner tube 3003 and the middle tube 3004 are formed integrally.

Moreover, in the above embodiment, the number of tubular supporting portions 3042 is four. However, the number of tubular supporting portions 3042 may be, for example, two or eight. To be specific, a passage through which the heat medium flows into the middle tube 3004 and a passage through which the heat medium flows out from the middle tube 3004 are only required to be constituted by the tubular supporting portions 3042.

Moreover, a projection which extends in the axial direction to the vicinity of a middle portion of the middle tube 3004 may be formed at the outer peripheral surface of the middle tube 3004. With this, a space in which the blood flows is formed between the hollow fiber membrane and the middle tube 3004, and the heat exchange can be more efficiently performed.

Moreover, the extending portion 3041c may include the cap portion 3015.

Furthermore, the outlet of the blood chamber 3003c may be provided as one or a plurality of holes provided on the surface of the middle tube 3004.

INDUSTRIAL APPLICABILITY

The present invention is applicable to an artificial lung device which removes carbon dioxide contained in blood and adds oxygen to the blood.

REFERENCE CHARACTERS LIST 1 artificial lung device
2 housing
20 blood inflow port
21 blood outflow port
43 hollow fiber body (gas exchanger)
54 recess (bubble trap portion)
56 straightening frame (bubble guide portion)
62 straightening surface
63 first straightening surface
64 second straightening surface
66 filter 66A filter
66B filter
70 bubble storing portion

The invention claimed is:
1. An artificial lung device comprising:
a housing including a blood inflow port and a blood outflow port and arranged such that a center axis of the housing is directed in a lateral direction;
a gas exchanger arranged in the housing and configured to perform gas exchange with respect to blood while the blood flows from the blood inflow port to the blood outflow port;
a filter structure arranged around the gas exchanger;
an opposing wall arranged so as to be opposed to a surface of the gas exchanger; and
a space constituted by the opposing wall and/or the filter structure, wherein
the opposing wall includes an inclined surface inclined toward the gas exchanger, and/or the filter structure includes an inclined surface inclined toward the gas exchanger,
the gas exchanger is formed in a columnar shape such that a center axis of the gas exchanger is directed in the lateral direction in the housing,
the space constitutes a bubble guide portion by which bubbles having flowed through the gas exchanger by flow of the blood are guided to the gas exchanger again in the housing,
the bubble guide portion includes a straightening surface provided so as to cross a passage extending from the gas exchanger to the blood outflow port,
the straightening surface is provided so as to be opposed to an outer peripheral surface of the gas exchanger and surround the gas exchanger,
the straightening surface includes:
a first straightening surface provided at a relatively lower side and inclined such that a downstream portion of the first straightening surface in a flow direction of the blood is located closer to the outer peripheral surface of the gas exchanger than an upstream portion of the first straightening surface in the flow direction of the blood; and
a second straightening surface provided at a relatively upper side and located closer to the outer peripheral surface of the gas exchanger than the upstream portion of the first straightening surface, and
when the straightening surface is divided into a lower portion and an upper portion by a predetermined horizontal plane, the lower portion is the first straightening surface, and the upper portion is the second straightening surface.
2. The artificial lung device according to claim 1, wherein, a filter is provided at the straightening surface.
3. The artificial lung device according to claim 1, wherein: an opening is formed at the first straightening surface; and a filter is provided at the opening.
4. The artificial lung device according to claim 1, wherein:
the second straightening surface is located so as to be spaced apart from the outer peripheral surface of the gas exchanger by a predetermined distance; and
a bubble storing portion is formed between the second straightening surface and the outer peripheral surface of the gas exchanger.
5. The artificial lung device according to claim 4, further comprising a bubble trap portion provided downstream of the bubble storing portion.
6. The artificial lung device according to claim 5, wherein the bubble trap portion includes an air vent port.
7. The artificial lung device according to claim 1, wherein at least the second straightening surface of the straightening surface is constituted by an inner wall surface of the housing.
8. The artificial lung device according to claim 1, wherein a filter is provided at the blood outflow port.
9. The artificial lung device according to claim 8, wherein the filter is formed in a columnar shape such that a dimension of the filter in the flow direction of the blood in the blood outflow port is larger than an inner diameter of the blood outflow port.
10. The artificial lung device according to claim 1, wherein:
the housing includes an attaching portion to which the blood outflow port is attached; and
a base end-side portion of the blood outflow port is attached to the attaching portion such that the blood outflow port is rotatable about an axis of the base end-side portion.
11. The artificial lung device according to claim 10, wherein the blood outflow port is bent such that a tip end-side portion of the blood outflow port forms a predetermined angle with respect to the axis of the base end-side portion.
12. The artificial lung device according to claim 10, wherein:
the attaching portion is formed in a substantially cylindrical shape;
an inner peripheral surface of the attaching portion includes an engaging portion;
the base end-side portion of the blood outflow port is attached to the attaching portion; and
the base end-side portion of the blood outflow port includes an engaged portion which is engaged with the engaging portion when the base end-side portion of the blood outflow port is attached to the attaching portion.
13. The artificial lung device according to claim 12, wherein:
one of the engaging portion and the engaged portion is constituted by a plurality of engagement pieces arranged so as to be spaced apart from each other in a circumferential direction;
each of the engagement pieces is formed in a tapered shape that projects inward in a radial direction as the engagement piece extends upward; and
the other of the engaging portion and the engaged portion is arranged so as to correspond to the engagement pieces, is formed so as to project outward in the radial direction, and is engaged with the plurality of engagement pieces so as to be located higher than the plurality of engagement pieces.
14. The artificial lung device according to claim 10, further comprising first and second sealing O-rings configured to seal between an outer peripheral surface of the base end-side portion and an inner peripheral surface of the attaching portion, wherein:
the first sealing O-ring is arranged at a portion of an outer peripheral surface of the base end-side portion of the blood outflow port which portion is closer to a base end of the blood outflow port than the second sealing O-ring; and
compressibility of the second sealing O-ring is higher than compressibility of the first sealing O-ring.
15. The artificial lung device according to claim 10, wherein:

the base end-side portion of the blood outflow port projects from the housing toward one side in an upper-lower direction;

a tip end-side portion of the blood outflow port is connected to the base end-side portion through a bent portion and is inclined outward in a radial direction so as to be directed toward one side in the upper-lower direction relative to the base end-side portion; and the blood outflow port includes a holding portion formed at the bent portion so as to project from the bent portion toward one side in the upper-lower direction.

16. An artificial lung device comprising:

a housing including a blood inflow port and a blood outflow port and arranged such that a center axis of the housing is directed in a lateral direction;

a gas exchanger arranged in the housing and configured to perform gas exchange with respect to blood while the blood flows from the blood inflow port to the blood outflow port;

a filter structure arranged around the gas exchanger;

an opposing wall arranged so as to be opposed to a surface of the gas exchanger; and a space constituted by the opposing wall and/or the filter structure, wherein the opposing wall includes an inclined surface inclined toward the gas exchanger, and/or the filter structure includes an inclined surface inclined toward the gas exchanger; and a separation dimension between the surface of the gas exchanger and the opposing wall gradually decreases to approach zero toward a vertically upper side.

17. The artificial lung device according to claim 16, wherein:

the filter structure configured to remove foreign matters in the blood is provided so as to cross a passage such that at least part of an inside surface of the filter structure contacts the surface of the gas exchanger, the passage being a passage through which the blood having flowed through the gas exchanger flows toward the blood outflow port; and the filter structure constitutes the opposing wall.

18. The artificial lung device according to claim 17, wherein:

the gas exchanger is provided such that part of the surface of the gas exchanger contacts an inner wall surface of the housing; and the inner wall surface of the housing constitutes the opposing wall.

19. The artificial lung device according to claim 18, further comprising a heat exchanger arranged in the housing and configured to adjust a temperature of the blood having flowed into the heat exchanger through the blood inflow port and deliver to the gas exchanger the blood having been adjusted in temperature, wherein:

the gas exchanger is formed in a tubular shape surrounding the heat exchanger;

a tubular wall is provided between the heat exchanger and the gas exchanger so as to separate the heat exchanger and the gas exchanger from each other; and a bubble guide portion is formed by an inner peripheral surface of the gas exchanger and a portion of the tubular wall which portion is opposed to the inner peripheral surface of the gas exchanger.

* * * * *